(12) United States Patent
Medlock et al.

(10) Patent No.: US 7,094,566 B2
(45) Date of Patent: Aug. 22, 2006

(54) IL-17 RECEPTOR LIKE MOLECULES AND USES THEREOF

(75) Inventors: Eugene Medlock, Westlake Village, CA (US); Richard Yeh, Ithaca, NY (US); Scott M. Silbiger, Woodland Hills, CA (US); Gary S. Elliott, Thousand Oaks, CA (US); Hung Q. Nguyen, Thousand Oaks, CA (US); Shuqian Jing, Thousand Oaks, CA (US)

(73) Assignee: Amgen Inc.,, Thousand Oaks, CA (US)

( * ) Notice: Subject to any disclaimer, the term of this patent is extended or adjusted under 35 U.S.C. 154(b) by 0 days.

(21) Appl. No.: 09/810,927

(22) Filed: Mar. 16, 2001

(65) Prior Publication Data

US 2005/0234221 A1    Oct. 20, 2005

Related U.S. Application Data

(63) Continuation-in-part of application No. 09/723,232, filed on Nov. 27, 2000, now abandoned.

(60) Provisional application No. 60/266,159, filed on Feb. 2, 2001, provisional application No. 60/213,125, filed on Jun. 22, 2000, provisional application No. 60/204,208, filed on May 12, 2000, provisional application No. 60/189,923, filed on Mar. 16, 2000.

(51) Int. Cl.
| | |
|---|---|
| *C12N 15/12* | (2006.01) |
| *C12N 5/10* | (2006.01) |
| *C12N 15/63* | (2006.01) |
| *C12P 21/02* | (2006.01) |
| *C07K 14/47* | (2006.01) |

(52) U.S. Cl. ............... 435/69.1; 435/320.1; 435/325; 435/235; 424/9.1; 424/85.2; 530/350; 530/351

(58) Field of Classification Search ............... 435/69.1, 435/320.1, 325; 536/23.5; 424/9.1, 85.2; 530/350, 351
See application file for complete search history.

(56) References Cited

U.S. PATENT DOCUMENTS

| | | | |
|---|---|---|---|
| 6,482,923 B1 | 11/2002 | Shi et al. | |
| 6,548,633 B1 | 4/2003 | Edwards et al. | |
| 6,635,443 B1 | 10/2003 | Shi et al. | |
| 2002/0102639 A1* | 8/2002 | Shaughnessy | 435/69.1 |

FOREIGN PATENT DOCUMENTS

| | | | |
|---|---|---|---|
| WO | WO 99/14240 | * | 3/1999 |
| WO | WO 99/35263 | | 7/1999 |
| WO | WO 99/61617 | | 12/1999 |
| WO | WO/0015759 | | 3/2000 |
| WO | WO 00/20593 | | 4/2000 |
| WO | WO 00/37491 | | 6/2000 |
| WO | WO 00/55204 | | 9/2000 |
| WO | WO 00/60080 | | 10/2000 |
| WO | WO 01/00806 | | 1/2001 |
| WO | WO 01/16318 | | 3/2001 |
| WO | WO 01/49728 | | 7/2001 |
| WO | WO 01/57202 | | 8/2001 |
| WO | WO 01/59120 | | 8/2001 |
| WO | WO 01/68848 | | 9/2001 |
| WO | WO 01/90358 | | 11/2001 |

OTHER PUBLICATIONS

Matsudaira et al., "Sequence from Picomole Quantities of Proteins Electroblotted onto Polyvinyl Difluoride Membranes," *J. Biol. Chem.*, 262:10035-10038 (1987).
Tian, et al., "Evi27 Encodes a Novel Membrane Protein with Homology to the IL-17 Receptor," *Oncogene* 19:2098-2109 (2000).
Yao, et al., "Molecular Characterization of the Human Interleukin (IL)-17 Receptor," *Cytokine* 9:794-800 (1997).

* cited by examiner

*Primary Examiner*—Janet Andres
*Assistant Examiner*—Fozia Hamud

(57) ABSTRACT

The present invention provides for IL-17 receptor like polypeptides and nucleic acid molecules encoding the same. The invention also provides vectors, host cells, agonists and antagonists (including selective binding agents), and methods for producing IL-17 receptor like polypeptides. Also provided for are methods for treatment, diagnosis, amelioration, or prevention of diseases with IL-17 receptor like polypeptides.

26 Claims, 26 Drawing Sheets
(5 of 26 Drawing Sheet(s) Filed in Color)

FIGURE 1A
Map of a First IL-17 Receptor Like cDNA (SEQ ID No: 1) and Amino Acid (SEQ ID NO: 2)

```
  1 ATAAAAGCGCAGCGTGCGGGTGGCCTGGATCCCGCGCAGTGGCCCGGCGATGTCGCTCGT  60
                                                         M  S  L  V  -

61 GCTGCTAAGCCTGGCCGCGCTGTGCAGGAGCGCCGTACCCCGAGAGCCGACCGTTCAATG 120
     L  L  S  L  A  A  L  C  R  S  A  V  P  R  E  P  T  V  Q  C  -

121 TGGCTCTGAAACTGGGCCATCTCCAGAGTGGATGCTACAACATGATCTAATCCCCGGAGA 180
     G  S  E  T  G  P  S  P  E  W  M  L  Q  H  D  L  I  P  G  D  -

181 CTTGAGGGACCTCCGAGTAGAACCTGTTACAACTAGTGTTGCAACAGGGGACTATTCAAT 240
     L  R  D  L  R  V  E  P  V  T  T  S  V  A  T  G  D  Y  S  I  -

241 TTTGATGAATGTAAGCTGGGTACTCCGGGCAGATGCCAGCATCCGCTTGTTGAAGGCCAC 300
     L  M  N  V  S  W  V  L  R  A  D  A  S  I  R  L  L  K  A  T  -

301 CAAGATTTGTGTGACGGGCAAAAGCAACTTCCAGTCCTACAGCTGTGTGAGGTGCAATTA 360
     K  I  C  V  T  G  K  S  N  F  Q  S  Y  S  C  V  R  C  N  Y  -

361 CACAGAGGCCTTCCAGACTCAGACCAGACCCTCTGGTGGTAAATGGACATTTTCCTACAT 420
     T  E  A  F  Q  T  Q  T  R  P  S  G  G  K  W  T  F  S  Y  I  -

421 CGGCTTCCCTGTAGAGCTGAACACAGTCTATTTCATTGGGGCCCATAATATTCCTAATGC 480
     G  F  P  V  E  L  N  T  V  Y  F  I  G  A  H  N  I  P  N  A  -

481 AAATATGAATGAAGATGGCCCTTCCATGTCTGTGAATTTCACCTCACCAGGCTGCCTAGA 540
     N  M  N  E  D  G  P  S  M  S  V  N  F  T  S  P  G  C  L  D  -

541 CCACATAATGAAATATAAAAAAAAGTGTGTCAAGGCCGGAAGCCTGTGGGATCCGAACAT 600
     H  I  M  K  Y  K  K  K  C  V  K  A  G  S  L  W  D  P  N  I  -

601 CACTGCTTGTAAGAAGAATGAGGAGACAGTAGAAGTGAACTTCACAACCACTCCCCTGGG 660
     T  A  C  K  K  N  E  E  T  V  E  V  N  F  T  T  T  P  L  G  -

661 AAACAGATACATGGCTCTTATCCAACACAGCACTATCATCGGGTTTTCTCAGGTGTTTGA 720
     N  R  Y  M  A  L  I  Q  H  S  T  I  I  G  F  S  Q  V  F  E  -

721 GCCACACCAGAAGAAACAAACGCGAGCTTCAGTGGTGATTCCAGTGACTGGGGATAGTGA 780
     P  H  Q  K  K  Q  T  R  A  S  V  V  I  P  V  T  G  D  S  E  -

781 AGGTGCTACGGTGCAGCTGACTCCATATTTTCCTACTTGTGGCAGCGACTGCATCCGACA 840
     G  A  T  V  Q  L  T  P  Y  F  P  T  C  G  S  D  C  I  R  H  -

841 TAAAGGAACAGTTGTGCTCTGCCCACAAACAGGCGTCCCTTTCCCTCTGGATAACAACAA 900
     K  G  T  V  V  L  C  P  Q  T  G  V  P  F  P  L  D  N  N  K  -

901 AAGCAAGCCGGGAGGCTGGCTGCCTCTCCTCCTGCTGTCTCTGCTGGTGGCCACATGGGT 960
     S  K  P  G  G  W  L  P  L  L  L  L  S  L  L  V  A  T  W  V  -
```

Figure 1B

```
 961 GCTGGTGGCAGGGATCTATCTAATGTGGAGGCACGAAAGGATCAAGAAGACTTCCTTTTC 1020
      L  V  A  G  I  Y  L  M  W  R  H  E  R  I  K  K  T  S  F  S  -

1021 TACCACCACACTACTGCCCCCCATTAAGGTTCTTGTGGTTTACCCATCTGAAATATGTTT 1080
      T  T  T  L  L  P  P  I  K  V  L  V  V  Y  P  S  E  I  C  F  -

1081 CCATCACACAATTTGTTACTTCACTGAATTTCTTCAAAACCATTGCAGAAGTGAGGTCAT 1140
      H  H  T  I  C  Y  F  T  E  F  L  Q  N  H  C  R  S  E  V  I  -

1141 CCTCGAAAAGTGGCAGAAAAAGAAAATAGCAGAGATGGGTCCAGTGCAGTGGCTTGCCAC 1200
      L  E  K  W  Q  K  K  K  I  A  E  M  G  P  V  Q  W  L  A  T  -

1201 TCAAAAGAAGGCAGCAGACAAAGTCGTCTTCCTTCTTTCCAATGACGTCAACAGTGTGTG 1260
      Q  K  K  A  A  D  K  V  V  F  L  L  S  N  D  V  N  S  V  C  -

1261 CGATGGTACCTGTGGCAAGAGCGAGGGCAGTCCCAGTGAGAACTCTCAAGACCTCTTCCC 1320
      D  G  T  C  G  K  S  E  G  S  P  S  E  N  S  Q  D  L  F  P  -

1321 CCTTGCCTTTAACCTTTTCTGCAGTGATCTAAGAAGCCAGATTCATCTGCACAAATACGT 1440
      L  A  F  N  L  F  C  S  D  L  R  S  Q  I  H  L  H  K  Y  V  -

1441 GGTGGTCTACTTTAGAGAGATTGATACAAAAGACGATTACAATGCTCTCAGTGTCTGCCC 1500
      V  V  Y  F  R  E  I  D  T  K  D  D  Y  N  A  L  S  V  C  P  -

1501 CAAGTACCACCTCATGAAGGATGCCACTGCTTTCTGTGCAGAACTTCTCCATGTCAAGCA 1560
      K  Y  H  L  M  K  D  A  T  A  F  C  A  E  L  L  H  V  K  Q  -

1561 GCAGGTGTCAGCAGGAAAAAGATCACAAGCCTGCCACGATGGCTGCTGCTCCTTGTAGCC 1620
      Q  V  S  A  G  K  R  S  Q  A  C  H  D  G  C  C  S  L  *

1621 CACCCATGAGAAGCAAGAGACCTTAAAGGCTTCCTATCCCACCAATTACAGGGAAAAAAC 1680

1681 GTGTGATGATCCTGAAGCTTACTATGCAGCCTACAAACAGCCTTAGTAATTAAAACATTT 1740

1741 TATACCAATAAAATTTTCAAATATTGCTAACTAATGTAGCATTAACTAACGATTGGAAAC 1800

1801 TACATTTACAACTTCAAAGCTGTTTTATACATAGAAATCAATTACAGCTTTAATTGAAAA 1860

1861 CTGTAACCATTTTGATAATGCAACAATAAAGCATCTTCAGC                    1901
```

FIGURE 2
Homology of a First IL-17 human Receptor Like Polypeptide
Amino Acid Seqeunce (SEQ ID NO: 2) and Known Human IL-17
Receptor Family Member (SEQ ID NO: 3)

```
  1 ............................MSLVLLSLAALCRSAVPREP  20
                              || ||    || |
  1 MGAARSPPSAVPGPLLGLLLLLLGVLAPGGASLRLLDHRALVCSQPGLNC  50

21 TVQCGSETGPSPEWMLQHDLIPGDLRDLRVEPVTTSVATGDYSILMNVSW  70
    ||.  .|     |.  .| |   :||.::        ||   ..: |
 51 TVK..NSTCLDDSWIHPRNLTPSSPKDLQIQLHFAHTQQGDLFPVAHIEW  98

71 VLRADASIRLLKATKICVTGKSNFQSYSCVRCNYTEAFQTQTRPSGGKWT 120
    |. ||||  |.  .: |  . |    |||      | ..|        :|
 99 TLQTDASILYLEGAELSVL.QLNTNERLCVRFE....FLSKLRHHHRRWR 143

121 FSYIGFPVELNTVYFIGAHNIPNANMNEDGPSMSVNFTSPGCLDHIMKYK 170
    |.:  ||:  .|  : |.:|    .|       |  ||  ||    ||
144 FTFSHFVVDPDQEYEVTVHHLPKPIPDGDPNHQSKNFLVPDCEHARMKVT 193

171 KKCVKAGSLWDPNITACKKNEETVEVNFTTTPLGNRYMALI.......QH 213
    |. .||||||||||     .|.||      | |:           |
194 TPCMSSGSLWDPNITVETLEAHQLRVSFTLWNESTHYQILLTSFPHMENH 243

214 STIIGFSQVFEPHQKKQTRASVVIPVTGDSEGA...TVQLTPYFPTCGSD 260
    |     :  |  .. .||    ..|      ||:  |: .| .|
244 SCFEHMHHIPAPRPEEFHQRSNVTLTLRNLKGCCRHQVQIQPFFSSCLND 293

261 CIRHKGTVVLCPQ.TGVPFPLDNNKSKPGGWLPLLLLLSLLVATWVLVAGI 309
    |:||   |  ||:   ||:  .        |  : :|:|.    |:.  :
294 CLRHSAT.VSCPEMPDTPEPIPDYMPLWVYWF.ITGISILLVGSVILLIV 341

310 YLMWRHERIKKTSFSTTT..........LLP....PIKVLVVYPSE.ICF 344
    : ||       :|  |           |:|    | ||  ::|  .:   :
342 CMTWRLAGPGSEKYSDDTKYTDGLPAADLIPPPLKPRKVWIIYSADHPLY 391

345 HHTICYFTEFLQNHCRSEVILEKWQKKKIAEMGPVQWLATQK....KAAD 390
    :  | :||     | .|| |:   :.. |.| | . |.   ||   ..
392 VDVVLKFAQFLLTACGTEVALDLLEEQAISEAGVMTWVGRQKQEMVESNS 441

391 KVVFLLSNDVNSVCDGTCGKSEGSP.......SENSQDLFPLAFNLFCSD 433
    |:: ||    .    |:  |.|     .  ||| | |:   |
442 KIIVLCSRGTRAKWQALLGR..GAPVRLRCDHGKPVGDLFTAAMNMILPD 489

434 LRSQIHLHKYVVVYFREIDTKDDY.NALSVCPKYHLMK..DATAFCAELL 480
    :     ||| || |:     |  .    |:|·||  :    |   : |
490 FKRPACFGTYVVCYFSEVSCDGDVPDLFGAAPRYPLMDRFEEVYFRIQDL 539

481 HVKQQVSAGKRSQACHDGCCSL*............................ 503
     |     : |
540 EMFQPGRMHRVGELSGDNYLRSPGGRQLRAALDRFRDWQVRCPDWFECEN 589
```

FIGURE 3A
Map of a Second Human IL-17 Receptor Like cDNA (SEQ ID NO: 4)
And Amino Acid (SEQ ID NO: 5) Sequences

```
  1 ATAAAAGCGC AGCGTGCGGGTG GCCTGGATCCCG CGCAGTGGCCCG GCGATGTCGCTC GT  60
                                                             M  S  L  V  -

61 GCTGCTAAG CCTGGCCGCGCT GTGCAGGAGCGC CGTACCCCGAGA GCCGACCGTTCA ATG 120
    L  L  S  L  A  A  L  C  R  S  A  V  P  R  E  P  T  V  Q  C  -

121 TGGCTCTGA AACTGGGCCATC TCCAGAGTGGAT GCTACAACATGA TCTAATCCCCGG AGA 180
    G  S  E  T  G  P  S  P  E  W  M  L  Q  H  D  L  I  P  G  D  -

181 CTTGAGGGA CCTCCGAGTAGA ACCTGTTACAAC TAGTGTTGCAAC AGGGGACTATTC AAT 240
    L  R  D  L  R  V  E  P  ·V  T  T  S  V  A  T  G  D  Y  S  I  -

241 TTTGATGAA TGTAAGCTGGGT ACTCCGGGCAGA TGCCAGCATCCG CTTGTTGAAGGC CAC 300
    L  M  N  V  S  W  V  L  R  A  D  A  S  I  R  L  L  K  A  T  -

301 CAAGATTTG TGTGACGGGCAA AAGCAACTTCCA GTCCTACAGCTG TGTGAGGCTGGA GTG 360
    K  I  C  V  T  G  K  S  N  F  Q  S  Y  S  C  V  R  L  E  C  -

361 CAGTGGTGC GATCATGGCTCG CTGCGACCTCAA TCTTCTGGGCTC AAGCGATCGTTC TGC 420
    S  G  A  I  M  A  R  C  D  L  N  L  L  G  S  S  D  R  S  A  -

421 TTCAGCCTC CCGAGCGGCTGG GACTGCAGGCGT GGGCCACCAGAC CTGGCTAATTTT TGT 480
    S  A  S  R  A  A  G  T  A  G  V  G  H  Q  T  W  L  I  F  V  -

481 AGTTTTTGT AGAGGGGGGTTT CACCGTGTTGCT GGTCTTGAATTC CAGTGCTCAGGC GAT 540
    V  F  V  E  G  G  F  T  V  L  L  V  L  N  S  S  A  Q  A  I  -

541 CTGCCTGCC TCGGCTTCCCAA AGTGCTGGGATT ACAGTGGACATT TTCCTACATCGG CTT 600
    C  L  P  R  L  P  K  V  L  G  L  Q  W  T  F  S  Y  I  G  F  -

601 CCCTGTAGA GCTGAACACAGT CTATTTCATTGG GGCCCATAATAT TCCTAATGCAAA TAT 660
    P  V  E  L  N  T  V  Y  F  I  G  A  H  N  I  P  N  A  N  M  -

661 GAATGAAGA TGGCCCTTCCAT GTCTGTGAATTT CACCTCACCAGG CTGCCTAGACCA CAT 720
    N  E  D  G  P  S  M  S  V  N  F  T  S  P  G  C  L  D  H  I  -

721 AATGAAATA TAAAAAAAAGTG TGTCAAGGCCGG AAGCCTGTGGGA TCCGAACATCAC TGC 780
    M  K  Y  K  K  K  C  V  K  A  G  S  L  W  D  P  N  I  T  A  -

781 TTGTAAGAA GAATGAGGAGAC AGTAGAAGTGAA CTTCACAACCAC TCCCCTGGGAAA CAG 840
    C  K  K  N  E  E  T  V  E  V  N  F  T  T  T  P  L  G  N  R  -

841 ATACATGGC TCTTATCCAACA CAGCACTATCAT CGGGTTTTCTCA GGTGTTTGAGCC ACA 900
    Y  M  A  L  I  Q  H  S  T  I  I  G  F  S  Q  V  F  E  P  H  -

901 CCAGAAGAA ACAAACGCGAGC TTCAGTGGTGAT TCCAGTGACTGG GGATAGTGAAGG TGC 960
    Q  K  K  Q  T  R  A  S  V  V  I  P  V  T  G  D  S  E  G  A  -

961 TACGGTGCA GCTGACTCCATA TTTTCCTACTTG TGGCAGCGACTG CATCCGACATAA AGG 1020
    T  V  Q  L  T  P  Y  F  P  T  C  G  S  D  C  I  R  H  K  G  -
```

Figure 3B

```
1021 AACAGTTGT GCTCTGCCCACA AACAGGCGTCCC TTTCCCTCTGGA TAACAACAAAAG CAA 1080
       T   V   V   L   C   P   Q   T   G   V   P   F   P   L   D   N   N   K   S   K   -

1081 GCCGGGAGG CTGGCTGCCTCT CCTCCTGCTGTC TCTGCTGGTGGC CACATGGGTGCT GGT 1140
       P   G   G   W   L   P   L   L   L   S   L   L   V   A   T   W   V   L   V   -

1141 GGCAGGGAT CTATCTAATGTG GAGGCACGAAAG GATCAAGAAGAC TTCCTTTTCTAC CAC 1200
       A   G   I   Y   L   M   W   R   H   E   R   I   K   K   T   S   F   S   T   T   -

1201 CACACTACT GCCCCCCATTAA GGTTCTTGTGGT TTACCCATCTGA AATATGTTTCCA TCA 1260
       T   L   L   P   P   I   K   V   L   V   V   Y   P   S   E   I   C   F   H   H   -

1261 CACAATTTG TTACTTCACTGA ATTTCTTCAAAA CCATTGCAGAAG TGAGGTCATCCT CGA 1320
       T   I   C   Y   F   T   E   F   L   Q   N   H   C   R   S   E   V   I   L   E   -

1321 AAAGTGGCA GAAAAAGAAAAT AGCAGAGATGGG TCCAGTGCAGTG GCTTGCCACTCA AAA 1380
       K   W   Q   K   K   K   I   A   E   M   G   P   V   Q   W   L   A   T   Q   K   -

1381 GAAGGCAGC AGACAAAGTCGT CTTCCTTCTTTC CAATGACGTCAA CAGTGTGTGCGA TGG 1440
       K   A   A   D   K   V   V   F   L   L   S   N   D   V   N   S   V   C   D   G   -

1441 TACCTGTGG CAAGAGCGAGGG CAGTCCCAGTGA GAACTCTCAAGA CCTCTTCCCCCT TGC 1500
       T   C   G   K   S   E   G   S   P   S   E   N   S   Q   D   L   F   P   L   A   -

1501 CTTTAACCT TTTCTGCAGTGA TCTAAGAAGCCA GATTCATCTGCA CAAATACGTGGT GGT 1560
       F   N   L   F   C   S   D   L   R   S   Q   I   H   L   H   K   Y   V   V   V   -

1561 CTACTTTAG AGAGATTGATAC AAAAGACGATTA CAATGCTCTCAG TGTCTGCCCCAA GTA 1620
       Y   F   R   E   I   D   T   K   D   D   Y   N   A   L   S   V   C   P   K   Y   -

1621 CCACCTCAT GAAGGATGCCAC TGCTTTCTGTGC AGAACTTCTCCA TGTCAAGCAGCA GGT 1680
       H   L   M   K   D   A   T   A   F   C   A   E   L   L   H   V   K   Q   Q   V   -

1681 GTCAGCAGG AAAAAGATCACA AGCCTGCCACGA TGGCTGCTGCTC CTTGTAGCCCAC CCA 1740
       S   A   G   K   R   S   Q   A   C   H   D   G   C   C   S   L   *

1741 TGAGAAGCA AGAGACCTTAAA GGCTTCCTATCC CACCAATTACAG GGAAAAAACGTG TGA 1800

1801 TGATCCTGA AGCTTACTATGC AGCCTACAAACA GCCTTAGTAATT AAAACATTTTAT ACC 1860

1861 AATAAAATT TTCAAATATTGC TAACTAATGTAG CATTAACTAACG ATTGGAAACTAC ATT 1920

1921 TACAACTTC AAAGCTGTTTTA TACATAGAAATC AATTACAGCTTT AATTGAAAACTG TAA 1980

1981 CCATTTTGA TAATGCAACAAT AAAGCATCTTCA GC                                  2015
```

FIGURE 4
Homology of a Second IL-17 Human Receptor Like Polypeptide
AMino Acid Sequence (SEQ ID No: 5) and KNown Human IL 17
Receptor Family Member (SEQ ID NO: 3)

```
  1 MSLVLLSLAALCRSAVPREPTVQCGSETGPSPEWMLQHDLIPGDLRDLRV  50
                                                   :  |
  1 ..............................................MGAARS   6

51 EPVTTSVATGDYSILMNVSWVLR.ADASIRLL.KATKICVTGKSNFQSYS  98
       ..|       :|:  . ||     ||:|||        :|       |  .
  7 PP..SAVPGPLLGLLLLLLGVLAPGGASLRLLDHRALVCSQPGLNCTVKN  54

99 CVRLECSGAIMARCDLNLLGSSDRSA......SASRAAGTAGVGHQNWLI 142
     |: |  |  |     ||  ||   :      ...        | | |  :
 55 STCLDDSW.IHPR...NLTPSSPKDLQIQLHFAHTQQGDLFPVAHIEWTL 100

143 ....FVVFVEGGFTVLLVLNSSAQAICL..PRLPKVL..GLQWTFSYIGF 184
        :.:.||     .|  ||..  :  :|.    ||  |.       .| |.:    |
101 QTDASILYLEGAELSVLQLNTN.ERLCVRFEFLSKLRHHHRRWRFTFSHF 149

185 PVELNTVYFIGAHNIPNANMNEDGPSMSVNFTSPGCLDHIMKYKKKCVKA 234
     |:   .   |  :  |:|        .|        |  ||  | |    ||       |.  .
150 VVDPDQEYEVTVHHLPKPIPDGDPNHQSKNFLVPDCEHARMKVTTPCMSS 199

235 GSLWDPNITACKKNEETVEVNFTTTPLGNRYMALI.......QHSTIIGF 277
    |||||||       .|.||         |   |:              ||
200 GSLWDPNITVETLEAHQLRVSFTLWNESTHYQILLTSFPHMENHSCFEHM 249

278 SQVFEPHQKKQTRASVVIPVTGDSEGA...TVQLTPYFPTCGSDCIRHKG 324
     :  |  ..  .||    ..|        ||: |:|  .|  .||:||
250 HHIPAPRPEEFHQRSNVTLTLRNLKGCCRHQVQIQPFFSSCLNDCLRHSA 299

325 TVVLCPQ.TGVPFPLDNNKSKPGGWLPLLLLSLLVATWVLVAGIYLMWRH 373
    | | ||:     | |: .      |   :  :|:|.     |:.   :  : ||
300 T.VSCPEMPDTPEPIPDYMPLWVYWF.ITGISILLVGSVILLIVCMTWRL 347

374 ERIKKTSFSTTT..........LLP....PIKVLVVYPSE.ICFHHTICY 408
      :|   |             |:|     | ||  ::|   .:      :        :
348 AGPGSEKYSDDTKYTDGLPAADLIPPPLKPRKVWIIYSADHPLYVDVVLK 397

409 FTEFLQNHCRSEVILEKWQKKKIAEMGPVQWLATQK....KAADKVVFLL 454
    |  :||     .||    |:    :..  |.|  ||      ..   |::  |
398 FAQFLLTACGTEVALDLLEEQAISEAGVMTWVGRQKQEMVESNSKIIVLC 447

455 SNDVNSVCDGTCGKSEGSP.......SENSQDLFPLAFNLFCSDLRSQIH 497
     |     .    |:  |.|       .    |||  | |:      |  :
448 SRGTRAKWQALLGR..GAPVRLRCDHGKPVGDLFTAAMNMILPDFKRPAC 495

498 LHKYVVVYFREIDTKDDY.NALSVCPKYHLMK..DATAFCAELLHVKQQV 544
    ||| || |:    |  .         |:|  ||    :    |  :  | .  |
496 FGTYVVCYFSEVSCDGDVPDLFGAAPRYPLMDRFEEVYFRIQDLEMFQPG 545

545 SAGKRSQACHDGCCSL*................................ 561
     :     :    |
546 RMHRVGELSGDNYLRSPGGRQLRAALDRFRDWQVRCPDWFECENLYSADD 595
```

FIGURE 5A
Map of a Third IL-17 Receptor Like cDNA (SEQ ID NO: 6) and Amino Acid (SEQ ID NO: 7) Sequence

```
  1 ATAAAAGCGCAGCGTGCGGGTGGCCTGGATCCCGCGCAGTGGCCCGGCGATGTCGCTCGT  60

61 GCTGCTAAGCCTGGCCGCGCTGTGCAGGAGCGCCGTACCCCGAGAGCCGACCGTTCAATG 120

121 TGGCTCTGAAACTGGGCCATCTCCAGAGTGGATGCTACAACATGATCTAATCCCGGGAGA 180

181 CTTGAGGGACCTCCGAGTAGAACCTGTTACAACTAGTGTTGCAACAGGGGACTATTCAAT 240

241 TTTGATGAATGTAAGCTGGGTACTCCGGGCAGATGTGGACATTTTCCTACATCGGCTTCC 300
                                            M  W  T  F  S  Y  I  G  F  P -

301 CTGTAGAGCTGAACACAGTCTATTTCATTGGGGCCCATAATATTCCTAATGCAAATATGA 360
     V  E  L  N  T  V  Y  F  I  G  A  H  N  I  P  N  A  N  M  N -

361 ATGAAGATGGCCCTTCCATGTCTGTGAATTTCACCTCACCAGGCTGCCTAGACCACATAA 420
     E  D  G  P  S  M  S  V  N  F  T  S  P  G  C  L  D  H  I  M -

421 TGAAATATAAAAAAAAGTGTGTCAAGGCCGGAAGCCTGTGGGATCCGAACATCACTGCTT 480
     K  Y  K  K  K  C  V  K  A  G  S  L  W  D  P  N  I  T  A  C -

481 GTAAGAAGAATGAGGAGACAGTAGAAGTGAACTTCACAACCACTCCCCTGGGAAACAGAT 540
     K  K  N  E  E  T  V  E  V  N  F  T  T  T  P  L  G  N  R  Y -

541 ACATGGCTCTTATCCAACACAGCACTATCATCGGGTTTTCTCAGGTGTTTGAGCCACACC 600
     M  A  L  I  Q  H  S  T  I  I  G  F  S  Q  V  F  E  P  H  Q -

601 AGAAGAAACAAACGCGAGCTTCAGTGGTGATTCCAGTGACTGGGGATAGTGAAGGTGCTA 660
     K  K  Q  T  R  A  S  V  V  I  P  V  T  G  D  S  E  G  A  T -

661 CGGTGCAGCTGACTCCATATTTTCCTACTTGTGGCAGCGACTGCATCCGACATAAAGGAA 720
     V  Q  L  T  P  Y  F  P  T  C  G  S  D  C  I  R  H  K  G  T -

721 CAGTTGTGCTCTGCCCACAAACAGGCGTCCCTTTCCCTCTGGATAACAACAAAAGCAAGC 780
     V  V  L  C  P  Q  T  G  V  P  F  P  L  D  N  N  K  S  K  P -

781 CGGGAGGCTGGCTGCCTCTCCTCCTGCTGTCTCTGCTGGTGGCCACATGGGTGCTGGTGG 840
     G  G  W  L  P  L  L  L  L  S  L  L  V  A  T  W  V  L  V  A -

841 CAGGGATCTATCTAATGTGGAGGCACGAAAGGATCAAGAAGACTTCCTTTTCTACCACCA 900
     G  I  Y  L  M  W  R  H  E  R  I  K  K  T  S  F  S  T  T  T -

901 CACTACTGCCCCCCATTAAGGTTCTTGTGGTTTACCCATCTGAAATATGTTTCCATCACA 960
     L  L  P  P  I  K  V  L  V  V  Y  P  S  E  I  C  F  H  H  T -

961 CAATTTGTTACTTCACTGAATTTCTTCAAAACCATTGCAGAAGTGAGGTCATCCTCGAAA 1020
     I  C  Y  F  T  E  F  L  Q  N  H  C  R  S  E  V  I  L  E  K -

1021 AGTGGCAGAAAAAGAAAATAGCAGAGATGGGTCCAGTGCAGTGGCTTGCCACTCAAAAGA 1080
      W  Q  K  K  K  I  A  E  M  G  P  V  Q  W  L  A  T  Q  K  K -

1081 AGGCAGCAGACAAAGTCGTCTTCCTTCTTTCCAATGACGTCAACAGTGTGTGCGATGGTA 1140
      A  A  D  K  V  V  F  L  L  S  N  D  V  N  S  V  C  D  G  T -

1141 CCTGTGGCAAGAGCGAGGGCAGTCCCAGTGAGAACTCTCAAGACCTCTTCCCCCTTGCCT 1200
      C  G  K  S  E  G  S  P  S  E  N  S  Q  D  L  F  P  L  A  F -
```

Figure 5B

```
1201 TTAACCTTTTCTGCAGTGATCTAAGAAGCCAGATTCATCTGCACAAATACGTGGTGGTCT 1260
      N  L  F  C  S  D  L  R  S  Q  I  H  L  H  K  Y  V  V  V  Y -

1261 ACTTTAGAGAGATTGATACAAAAGACGATTACAATGCTCTCAGTGTCTGCCCCAAGTACC 1320
      F  R  E  I  D  T  K  D  D  Y  N  A  L  S  V  C  P  K  Y  H -

1321 ACCTCATGAAGGATGCCACTGCTTTCTGTGCAGAACTTCTCCATGTCAAGCAGCAGGTGT 1380
      L  M  K  D  A  T  A  F  C  A  E  L  L  H  V  K  Q  Q  V  S -

1381 CAGCAGGAAAAAGATCACAAGCCTGCCACGATGGCTGCTGCTCCTTGTAGCCCACCCATG 1440
      A  G  K  R  S  Q  A  C  H  D  G  C  C  S  L  *

1441 AGAAGCAAGAGACCTTAAAGGCTTCCTATCCCACCAATTACAGGGAAAAAACGTGTGATG 1500

1501 ATCCTGAAGCTTACTATGCAGCCTACAAACAGCCTTAGTAATTAAAACATTTTATACCAA 1560

1561 TAAAATTTTCAAATATTGCTAACTAATGTAGCATTAACTAACGATTGGAAACTACATTTA 1620

1621 CAACTTCAAAGCTGTTTTATACATAGAAATCAATTACAGCTTTAATTGAAAACTGTAACC 1680

1681 ATTTTGATAATGCAACAATAAAGCATCTTCAGC                            1713
```

FIGURE 6
Homology of a Third Human IL-17 Receptor Like Polypeptide Amino Acid Sequence (SEQ ID NO: 7) and Known Human IL-17 Receptor Family Member (SEQ ID NO: 3)

```
  1 ........................................MWTFSYIGFP  10
                                            | |.: |
101 QTDASILYLEGAELSVLQLNTNERLCVRFEFLSKLRHHHRRWRFTFSHFV 150

11 VELNTVYFIGAHNIPNANMNEDGPSMSVNFTSPGCLDHIMKYKKKCVKAG  60
    |:. | : |.:|  . |   ||| | |   ||   |..|
151 VDPDQEYEVTVHHLPKPIPDGDPNHQSKNFLVPDCEHARMKVTTPCMSSG 200

61 SLWDPNITACKKNEETVEVNFTTTPLGNRYMALI.......QHSTIIGFS 103
    |||||||     .|.||       | |:         ||
201 SLWDPNITVETLEAHQLRVSFTLWNESTHYQILLTSFPHMENHSCFEHMH 250

104 QVFEPHQKKQTRASVVIPVTGDSEGA...TVQLTPYFPTCGSDCIRHKGT 150
    :  |  .. . | |      . |   ||: |:| .| .||:|| |
251 HIPAPRPEEFHQRSNVTLTLRNLKGCCRHQVQIQPFFSSCLNDCLRHSAT 300

151 VVLCPQ.TGVPFPLDNNKSKPGGWLPLLLLSLLVATWVLVAGIYLMWRHE 199
    | ||:  | |: .   |  : :|:|.   |:.  : : ||
301 .VSCPEMPDTPEPIPDYMPLWVYWF.ITGISILLVGSVILLIVCMTWRLA 348

200 RIKKTSFSTTT..........LLP....PIKVLVVYPSE.ICFHHTICYF 234
    :| |          |:|    | ||  ::| .:   :   : |
349 GPGSEKYSDDTKYTDGLPAADLIPPPLKPRKVWIIYSADHPLYVDVVLKF 398

235 TEFLQNHCRSEVILEKWQKKKIAEMGPVQWLATQK....KAADKVVFLLS 280
    :||  | .||  |: :.. |.| | .|. ||    .. |::  |  |
399 AQFLLTACGTEVALDLLEEQAISEAGVMTWVGRQKQEMVESNSKIIVLCS 448

281 NDVNSVCDGTCGKSEGSP.......SENSQDLFPLAFNLFCSDLRSQIHL 323
    .    |:  |.|  .    ||| | |:   | :
449 RGTRAKWQALLGR..GAPVRLRCDHGKPVGDLFTAAMNMILPDFKRPACF 496

324 HKYVVVYFREIDTKDDY.NALSVCPKYHLMK..DATAFCAELLHVKQQVS 370
    ||| || |:  | .     |:| ||   :   |  :| . |
497 GTYVVCYFSEVSCDGDVPDLFGAAPRYPLMDRFEEVYFRIQDLEMFQPGR 546

371 AGKRSQACHDGCCSL*.................................. 386
    :  : |
547 MHRVGELSGDNYLRSPGGRQLRAALDRFRDWQVRCPDWFECENLYSADDQ 596
```

FIGURE 7
Overlap of Amino Acid Sequences of the First (SEQ ID NO: 2),
Second (SEQ ID NO: 5), and Third (SEQ ID NO: 7) Human IL-17
Receptor Like Polypeptides

```
  1   MSLVLLSLAA  LCRSAVPREP  TVQCGSETGP  SPEWMLQHDL  IPGDLRDLRV
  1   MSLVLLSLAA  LCRSAVPREP  TVQCGSETGP  SPEWMLQHDL  IPGDLRDLRV

51   EPVTTSVATG  DYSILMNVSW  VLRADASIRL  LKATKICVTG  KSNFQSYSCV
 51   EPVTTSVATG  DYSILMNVSW  VLRADASIRL  LKATKICVTG  KSNFQSYSCV

101   RCNYTEAFQT  QTRPSGGK--  ----------  ----------  ----------
101   RLECSGAIMA  RCDLNLLGSS  DRSASASRAA  GTAGVGHQNW  LIFVVFVEGG

119   ----------  ----------  ------WTFS  YIGFPVELNT  VYFIGAHNIP
151   FTVLLVLNSS  AQAICLPRLP  KVLGLQWTFS  YIGFPVELNT  VYFIGAHNIP
  1                                MWTFS  YIGFPVELNT  VYFIGAHNIP

143   NANMNEDGPS  MSVNFTSPGC  LDHIMKYKKK  CVKAGSLWDP  NITACKKNEE
201   NANMNEDGPS  MSVNFTSPGC  LDHIMKYKKK  CVKAGSLWDP  NITACKKNEE
 26   NANMNEDGPS  MSVNFTSPGC  LDHIMKYKKK  CVKAGSLWDP  NITACKKNEE

193   TVEVNFTTTP  LGNRYMALIQ  HSTIIGFSQV  FEPHQKKQTR  ASVVIPVTGD
251   TVEVNFTTTP  LGNRYMALIQ  HSTIIGFSQV  FEPHQKKQTR  ASVVIPVTGD
 76   TVEVNFTTTP  LGNRYMALIQ  HSTIIGFSQV  FEPHQKKQTR  ASVVIPVTGD

243   SEGATVQLTP  YFPTCGSDCI  RHKGTVVLCP  QTGVPFPLDN  NKSKPGGWLP
301   SEGATVQLTP  YFPTCGSDCI  RHKGTVVLCP  QTGVPFPLDN  NKSKPGGWLP
126   SEGATVQLTP  YFPTCGSDCI  RHKGTVVLCP  QTGVPFPLDN  NKSKPGGWLP

293   LLLLSLLVAT  WVLVAGIYLM  WRHERIKKTS  FSTTTLLPPI  KVLVVYPSEI
351   LLLLSLLVAT  WVLVAGIYLM  WRHERIKKTS  FSTTTLLPPI  KVLVVYPSEI
176   LLLLSLLVAT  WVLVAGIYLM  WRHERIKKTS  FSTTTLLPPI  KVLVVYPSEI

343   CFHHTICYFT  EFLQNHCRSE  VILEKWQKKK  IAEMGPVQWL  ATQKKAADKV
401   CFHHTICYFT  EFLQNHCRSE  VILEKWQKKK  IAEMGPVQWL  ATQKKAADKV
226   CFHHTICYFT  EFLQNHCRSE  VILEKWQKKK  IAEMGPVQWL  ATQKKAADKV

393   VFLLSNDVNS  VCDGTCGKSE  GSPSENSQDL  FPLAFNLFCS  DLRSQIHLHK
451   VFLLSNDVNS  VCDGTCGKSE  GSPSENSQDL  FPLAFNLFCS  DLRSQIHLHK
276   VFLLSNDVNS  VCDGTCGKSE  GSPSENSQDL  FPLAFNLFCS  DLRSQIHLHK

443   YVVVYFREID  TKDDYNALSV  CPKYHLMKDA  TAFCAELLHV  KQQVSAGKRS
501   YVVVYFREID  TKDDYNALSV  CPKYHLMKDA  TAFCAELLHV  KQQVSAGKRS
326   YVVVYFREID  TKDDYNALSV  CPKYHLMKDA  TAFCAELLHV  KQQVSAGKRS

493   QACHDGCCSL  *
551   QACHDGCCSL  *
376   QACHDGCCSL  *
```

Northern Blot Expression Analysis of TH00-018
Necropsied Transgenic Founders

Figure 11
Non-Transgenics    IL-17E Transgenics
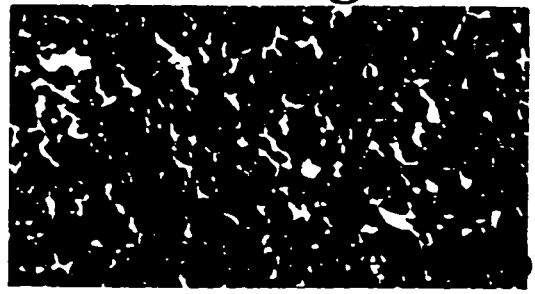
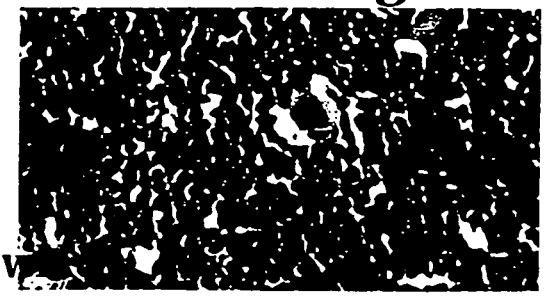

CD45R+ CELLS EXPRESSING IL17Br IN TRANSGENIC BONE MARROW

CD4+ CELLS EXPRESSING IL17Br IN TRANSGENIC BONE MARROW

Figure 22
           IL-17RB-2 Fusion Protein (SEQ ID NO: 24)

1    *MSLVLLSLAA LCRS*AVPREP TVQCGSETGP SPEWMLQHDL IPGDLRDLRV
51   EPVTTSVATG DYSILMNVSW VLRADASIRL LKATKICVTG KSNFQSYSCV
101  RCNYTEAFQT QTRPSGGKWT FSYIGFPVEL NTVYFIGAHN IPNANMNEDG
151  PSMSVNFTSP GCLDHIMKYK KKCVKAGSLW DPNITACKKN EETVEVNFTT
201  TPLGNRYMAL IQHSTIIGFS QVFEPHQKKQ TRASVVIPVT GDSEGATVQL
251  TPYFPTCGSD CIRHKGTVVL CPQTGVPFPL DNNKSKPGGW LPAAAEPKSC
301  DKTHTCPPCP APELLGGPSV FLFPPKPKDT LMISRTPEVT CVVVDVSHED
351  PEVKFNWYVD GVEVHNAKTK PREEQYNSTY RVVSVLTVLH QDWLNGKEYK
401  CKVSNKALPA PIEKTISKAK GQPREPQVYT LPPSRDELTK NQVSLTCLVK
451  GFYPSDIAVE WESNGQPENN YKTTPPVLDS DGSFFLYSKL TVDKSRWQQG
501  NVFSCSVMHE ALHNHYTQKS LSLSPGK*

Figure 23

Fusion Protein for IL-17RB-3 (SEQ ID NO: 25)

```
  1  MSLVLLSLAA  LCRSAVPREP  TVQCGSETGP  SPEWMLQHDL  IPGDLRDLRV
 51  EPVTTSVATG  DYSILMNVSW  VLRADASIRL  LKATKICVTG  KSNFQSYSCV
101  RLECSGAIMA  RCDLNLLGSS  DRSASASRAA  GTAGVGHQTW  LIFVVFVEGG
151  FTVLLVLNSS  AQAICLPRLP  KVLGLQWTFS  YIGFPVELNT  VYFIGAHNIP
201  NANMNEDGPS  MSVNFTSPGC  LDHIMKYKKK  CVKAGSLWDP  NITACKKNEE
251  TVEVNFTTTP  LGNRYMALIQ  HSTIIGFSQV  FEPHQKKQTR  ASVVIPVTGD
301  SEGATVQLTP  YFPTCGSDCI  RHKGTVVLCP  QTGVPFPLDN  NKSKPGGWLP
351  AAAEPKSCDK  THTCPPCPAP  ELLGGPSVFL  FPPKPKDTLM  ISRTPEVTCV
401  VVDVSHEDPE  VKFNWYVDGV  EVHNAKTKPR  EEQYNSTYRV  VSVLTVLHQD
451  WLNGKEYKCK  VSNKALPAPI  EKTISKAKGQ  PREPQVYTLP  PSRDELTKNQ
501  VSLTCLVKGF  YPSDIAVEWE  SNGQPENNYK  TTPPVLDSDG  SFFLYSKLTV
551  DKSRWQQGNV  FSCSVMHEAL  HNHYTQKSLS  LSPGK*
```

IL-17 RECEPTOR LIKE MOLECULES AND USES THEREOF

RELATED APPLICATION

This application claims priority from continuation in part U.S. patent application Ser. No. 09/723,232 filed Nov. 27, 2000 Now ABN which claims priority from U.S. provisional patent application Ser. No. 60/189,923 filed Mar. 16, 2000 and U.S. provisional application Ser. No. 60/204,208 filed May 12, 2000. This application also claims priority from U.S. provisional application No. 60/266,159 filed Feb. 2, 2001 and U.S. provisional application No. 60/213,125 filed Jun. 22, 2000. All of the above-identified applications are incorporated herein by reference in their entirety.

FIELD OF THE INVENTION

The present invention relates to novel IL-17 receptor like polypeptides and nucleic acid molecules encoding the same. The invention also relates to vectors, host cells, pharmaceutical compositions, selective binding agents and methods for producing IL-17 receptor like polypeptides. Also provided for are methods for the diagnosis, treatment, amelioration, and/or prevention of diseases associated with IL-17 receptor like polypeptides.

BACKGROUND OF THE INVENTION

Technical advances in the identification, cloning, expression and manipulation of nucleic acid molecules have greatly accelerated the discovery of novel therapeutics based upon deciphering the human genome. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences can allow one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides to create variants and derivatives thereof may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics, or those encoding polypeptides, which may act as "targets" for therapeutic molecules, have still not been identified. In addition, structural and functional analyses of polypeptide products from many genes have not been undertaken.

Accordingly, it is an object of the invention to identify novel polypeptides and nucleic acid molecules encoding the same, which have diagnostic or therapeutic benefit.

SUMMARY OF THE INVENTION

The present invention relates to novel IL-17 receptor like nucleic acid molecules and encoded polypeptides.

The invention provides for an isolated nucleic acid molecule comprising a nucleotide sequence selected from the group consisting of:

(a) the nucleotide sequence as set forth in any of SEQ ID NO:1, SEQ ID NO:4, or SEQ ID NO:6, including combinations thereof;

(b) a nucleotide sequence encoding the polypeptide as set forth in any of SEQ ID NO:2, SEQ ID NO:5, or SEQ ID NO:7, including combinations thereof;

(c) a nucleotide sequence which hybridizes under moderately or highly stringent conditions to the complement of (a) or (b), wherein the polypeptide encoded by the nucleotide sequence has an activity of the polypeptide as set forth in any of SEQ ID NO:2, SEQ ID NO:5, or SEQ ID NO:7, including combinations thereof; and (d) a nucleotide sequence complementary to any of (a)–(c).

The invention also provides for an isolated nucleic acid molecule comprising a nucleotide sequence selected from the group consisting of:

(a) a nucleotide sequence encoding a polypeptide that is at least about 70, 75, 80, 85, 90, 95, 96, 97, 98, or 99 percent identical to the polypeptide as set forth in any of SEQ ID NO:2, SEQ ID NO:5, or SEQ ID NO:7, including combinations thereof, wherein the polypeptide has an activity of the polypeptide as set forth in any of SEQ ID NO:2, SEQ ID NO:5, or SEQ ID NO:7, including combinations thereof;

(b) a nucleotide sequence encoding an allelic variant or splice variant of the nucleotide sequence as set forth in any of SEQ ID NO:1, SEQ ID NO:4, or SEQ ID NO:6, including combinations thereof, wherein the encoded polypeptide has an activity of the polypeptide as set forth in any of SEQ ID NO:2, SEQ ID NO:5, or SEQ ID NO:7, including combinations thereof;

(c) a nucleotide sequence of any of SEQ ID NO:1, SEQ ID NO:4, or SEQ ID NO:6, including combinations thereof; (a), or (b) encoding a polypeptide fragment of at least about 25 amino acid residues, wherein the polypeptide has an activity of the polypeptide as set forth in any of SEQ ID NO:2, SEQ ID NO:5, or SEQ ID NO:7, including combinations thereof;

(d) a nucleotide sequence of any of SEQ ID NO:1, SEQ ID NO:4, or SEQ ID NO:6, including combinations thereof; or (a)–(d) comprising a fragment of at least about 16 nucleotides;

(e) a nucleotide sequence which hybridizes under moderately or highly stringent conditions to the complement of any of (a)–(d), wherein the polypeptide encoded by the nucleotide sequence has an activity of the polypeptide as set forth in any of SEQ ID NO:2, SEQ ID NO:5, or SEQ ID NO:7, including combinations thereof; and (f) a nucleotide sequence complementary to any of (a)–(e).

The invention further provides for an isolated nucleic acid molecule comprising a nucleotide sequence selected from the group consisting of:

(a) a nucleotide sequence encoding a polypeptide as set forth in any of SEQ ID NO:2, SEQ ID NO:5, or SEQ ID NO:7, including combinations thereof, with at least one conservative amino acid substitution, wherein the polypeptide has an activity of the polypeptide as set forth in any of SEQ ID NO:2, SEQ ID NO:5, or SEQ ID NO:7, including combinations thereof;

(b) a nucleotide sequence encoding a polypeptide as set forth in any of SEQ ID NO:2, SEQ ID NO:5, or SEQ ID NO:7, including combinations thereof, with at least one amino acid insertion, wherein the polypeptide has an activity of the polypeptide as set forth in any of SEQ ID NO:2, SEQ ID NO:5, or SEQ ID NO:7, including combinations thereof;

(c) a nucleotide sequence encoding a polypeptide as set forth in any of SEQ ID NO:2, SEQ ID NO:5, or SEQ ID NO:7, including combinations thereof, with at least one amino acid deletion, wherein the polypeptide has an activity of the polypeptide as set forth in any of SEQ ID NO:2, SEQ ID NO:5, or SEQ ID NO:7, including combinations thereof;

(d) a nucleotide sequence encoding a polypeptide as set forth in any of SEQ ID NO:2, SEQ ID NO:5, or SEQ ID NO:7, including combinations thereof, which has a C- and/or N-terminal truncation, wherein the polypeptide has an activity of the polypeptide as set forth in any of SEQ ID NO:2, SEQ ID NO:5, or SEQ ID NO:7, including combinations thereof;

(e) a nucleotide sequence encoding a polypeptide as set forth in any of SEQ ID NO:2, SEQ ID NO:5, or SEQ ID NO:7, including combinations thereof, with at least one modification selected from the group consisting of amino acid substitutions, amino acid insertions, amino acid deletions, C-terminal truncation, and N-terminal truncation, wherein the polypeptide has an activity of the polypeptide as set forth in any of SEQ ID NO:2, SEQ ID NO:5, or SEQ ID NO:7, including combinations thereof;

(f) a nucleotide sequence of (a)–(e) comprising a fragment of at least about 16 nucleotides;

(g) a nucleotide sequence which hybridizes under moderately or highly stringent conditions to the complement of any of (a)–(f), wherein the polypeptide encoded by the nucleotide sequence has an activity of the polypeptide as set forth in any of SEQ ID NO:2, SEQ ID NO:5, or SEQ ID NO:7, including combinations thereof; and (h) a nucleotide sequence complementary to any of (a)–(e).

The invention also provides for an isolated polypeptide comprising the amino acid sequence selected from the group consisting of:

(a) an amino acid sequence for an ortholog of any of SEQ ID NO:2, SEQ ID NO:5, or SEQ ID NO:7, including combinations thereof, wherein the encoded polypeptide has an activity of the polypeptide as set forth in any of SEQ ID NO:2, SEQ ID NO:5, or SEQ ID NO:7, including combinations thereof;

(b) an amino acid sequence that is at least about 70, 80, 85, 90, 95, 96, 97, 98, or 99 percent identical to the amino acid sequence of any of SEQ ID NO:2, SEQ ID NO:5, or SEQ ID NO:7, including combinations thereof, wherein the polypeptide has an activity of the polypeptide as set forth in any of SEQ ID NO:2, SEQ ID NO:5, or SEQ ID NO:7, including combinations thereof;

(c) a fragment of the amino acid sequence set forth in any of SEQ ID NO:2, SEQ ID NO:5, or SEQ ID NO:7, including combinations thereof, comprising at least about 25 amino acid residues, wherein the polypeptide has an activity of the polypeptide as set forth in any of SEQ ID NO:2, SEQ ID NO:5, or SEQ ID NO:7, including combinations thereof;

(d) an amino acid sequence for an allelic variant or splice variant of either the amino acid sequence as set forth in any of SEQ ID NO:2, SEQ ID NO: 5, or SEQ ID NO:7, including combinations thereof, or at least one of (a)–(b) wherein the polypeptide has an activity of the polypeptide as set forth in any of SEQ ID NO:2, SEQ ID NO:5, or SEQ ID NO:7, including combinations thereof.

The invention further provides for an isolated polypeptide comprising the amino acid sequence selected from the group consisting of:

(a) the amino acid sequence as set forth in any of SEQ ID NO:2, SEQ ID NO:5, or SEQ ID NO:7, including combinations thereof, with at least one conservative amino acid substitution, wherein the polypeptide has an activity of the polypeptide as set forth in any of SEQ ID NO:2, SEQ ID NO:5, or SEQ ID NO:7, including combinations thereof;

(b) the amino acid sequence as set forth in any of SEQ ID NO:2, SEQ ID NO:5, or SEQ ID NO:7, including combinations thereof, with at least one amino acid insertion, wherein the polypeptide has an activity of the polypeptide as set forth in any of SEQ ID NO:2, SEQ ID NO:5, or SEQ ID NO:7, including combinations thereof;

(c) the amino acid sequence as set forth in any of SEQ ID NO:2, SEQ ID NO:5, or SEQ ID NO:7, including combinations thereof with at least one amino acid deletion, wherein the polypeptide has an activity of the polypeptide as set forth in any of SEQ ID NO:2, SEQ ID NO:5, or SEQ ID NO:7, including combinations thereof;

(d) the amino acid sequence as set forth in any of SEQ ID NO:2, SEQ ID NO:5, or SEQ ID NO:7, including combinations thereof, which has a C- and/or N-terminal truncation, wherein the polypeptide has an activity of the polypeptide as set forth in any of SEQ ID NO:2, SEQ ID NO:5, or SEQ ID NO:7, including combinations thereof; and (e) the amino acid sequence as set forth in any of SEQ ID NO:2, SEQ ID NO:5, or SEQ ID NO:7, including combinations thereof, with at least one modification selected from the group consisting of amino acid substitutions, amino acid insertions, amino acid deletions, C-terminal truncation, and N-terminal truncation, wherein the polypeptide has an activity of the polypeptide as set forth in any of SEQ ID NO:2, SEQ ID NO:5, or SEQ ID NO:7, including combinations thereof.

Also provided are fusion polypeptides comprising the amino acid sequences of (a)–(e) above.

The present invention also provides for an expression vector comprising the isolated nucleic acid molecules as set forth herein, recombinant host cells comprising recombinant nucleic acid molecules as set forth herein, and a method of producing an IL-17 receptor like polypeptide comprising culturing the host cells and optionally isolating the polypeptide so produced. These expression vectors include baculovirus expression vectors which utilize insect cells for expression.

The host cells of the present invention also include those comprising a IL-17 receptor nucleic acid molecule operatively linked to a regulatory sequence other than the promoter of the native IL-17 receptor like polypeptide. These host cells also include those modified by transformation or transfection with a heterologous nucleic acid, including promoters and transcription factors, that promotes transcription or translation of the nucleic acid comprising the sequence of SEQ ID NO:1, 4, or 6 or a allelic variant or fragment thereof.

Vectors containing the cDNA inserts corresponding to SEQ ID NOS: 1, 4 and 6 (denoted HIL-17RB-2, IL-17RB-3 and IL-17RB1, respectively) have been deposited on Mar. 14, 2001 with the American Type Culture Collection, 10801 University Blvd., Manassas, Va. 20110, U.S.A. under Accession Nos. PTA-3176. PTA-3177 and PTA-3175, respectively). Included in the present invention are isolated polynucleotides comprising the protein coding or mature protein coding regions of the respective cDNA inserts, as well as mature protein or extracellular domains thereof obtainable by expressing cDNA in suitable host cells.

A transgenic non-human animal comprising a nucleic acid molecule encoding an IL-17 receptor like polypeptide is also encompassed by the invention. The IL-17 receptor like nucleic acid molecules are introduced into the animal in a manner that allows expression and increased levels of the IL-17 receptor like polypeptide, which may include increased circulating levels. The transgenic non-human animal is preferably a mammal. Also provided is a transgenic non-human animal comprising a disruption in the nucleic acid molecule encoding IL-17 receptor like polypeptide, which will knock out or significantly decrease expression if the IL-17 receptor like polypeptide.

Also provided are derivatives of the IL-17 receptor like polypeptides of the present invention.

Analogs of the IL-17 receptor like polypeptides are provided for in the present invention which result from conservative and/or non-conservative amino acids substitutions of the IL-17 receptor like polypeptides of SEQ ID NO: 2, 5 or 7. Such analogs include an IL-17 receptor like polypeptide wherein, for example the amino acid at position 167 of SEQ ID NO: 2, position 225 of SEQ ID NO: 5 or position 50 of SEQ ID No: 7 is methionine, leucine, isoleucine, or phenylalanine; the amino acid at position 261 of SEQ ID NO: 2, position 319 of SEQ ID NO: 5 or position 144 of SEQ ID NO: 7 is cysteine, serine or alanine; the amino acid at position 299 of SEQ ID NO: 2, position 357 of SEQ ID NO: 5 or position 212 of SEQ ID NO: 7 is leucine, norleucine, glutamine, asparagine, arginine, or 1,4, diamino-butyric Acid; the amino acid at position 313 of SEQ ID NO: 2, position 371 of SEQ ID NO: 5 or position 193 of SEQ ID NO: 7 is tryptophan, tyrosine or phenylalanine; the amino acid at position 413 of SEQ ID NO: 2, position 471 of SEQ ID NO: 5, or position 296 of SEQ ID NO: 7 is glycine, proline or alanine; or the amino acid at position 433 of SEQ ID NO: 2, position 491 of SEQ ID NO: 5 or position 313 of SEQ ID NO: 7 is aspartic acid or glutamic acid.

Additionally provided are selective binding agents such as antibodies and peptides capable of specifically binding the IL-17 receptor like polypeptides of the invention. Such antibodies, polypeptides and small molecules may be agonistic or antagonistic. Antagonistic selective binding agents include those which inhibit binding of a IL-17 receptor like polypeptide to an IL-17E ligand (such as the mature protein amino acid sequence of SEQ ID NO: 23).

Pharmaceutical compositions comprising the nucleotides, polypeptides, or selective binding agents of the present invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The IL-17 receptor like polypeptides and nucleic acid molecules of the present invention may be used to treat, prevent, ameliorate, diagnosis and/or detect diseases and disorders, including those recited herein. Expression analysis in biological, cellular or tissue samples suggests that IL-17 receptor like polypeptide may play a role in the diagnosis and/or treatment of the pathological conditions described herein. This expression can be detected with a diagnostic agent such as a IL-17 receptor like polynucleotide.

The invention encompasses diagnosing a pathological condition or the susceptibility to a pathological condition in a subject caused by or resulting from abnormal (i.e. increased or decreased) levels of IL-17 receptor like polypeptide comprising determining the presence or amount of expression of the IL-17 receptor like polypeptide in a sample and comprising the level of said polypeptide in a biological, tissue or cellular sample from either normal subjects or the subject at an earlier time, wherein susceptibility to a pathological condition is based on the presence or amount of expression of the polypeptide The present invention also provides a method of assaying test molecules to identify a test molecule which binds to an IL-17 receptor like polypeptide. The method comprises contacting an IL-17 receptor like polypeptide with a test molecule and determining the extent of binding of the test molecule to the polypeptide. The method further comprises determining whether such test molecules are agonists or antagonists (candidate inhibitors and stimulators)of an IL-17 receptor like polypeptide. The present invention further provides a method of testing the impact of molecules on the expression of IL-17 receptor like polypeptide or on the activity of IL-17 receptor like polypeptide.

The present invention provides for methods of identifying antagonists or agonists of IL-17 receptor like biological activity comprising contacting a small molecule compound with IL-17 receptor like polypeptides and measuring IL-17 receptor like biological activity in the presence and absence of these small molecules. These small molecules can be a naturally occurring medicinal compound or derived from combinational chemical libraries. In certain embodiments, an IL-17 receptor like polypeptide agonist or antagonist may be a protein, peptide, carbohydrate, lipid, or small molecule which interacts with an IL-17 receptor like polypeptide to regulate its activity or inhibit ligand binding.

The IL-17 receptor like polypeptide can be used for identifying ligands thereof. Various forms of "expression cloning" have been used for cloning ligands for receptors. See e.g., Davis et al., Cell, 87:1161–1169 (1996). These and other IL-17 receptor like ligand cloning experiments are described in greater detail herein. Isolation of the IL-17 receptor like ligand(s) allows for the identification or development of novel agonists and/or antagonists of the IL-17 receptor like signaling pathway.

One ligand (denoted herein as IL-17E) has been identified herein in Example 8. Its nucleotide and amino acid sequences are set forth in SEQ ID NOS: 22 and 23, respectively. The cDNA encodes an open reading frame of 161 amino acids with a predicted signal peptide of 16 amino acids and a predicted mature protein of 145 amino acids. Tissue expression data, homology to other IL-17 ligands and phenotypes of transgenic mice overexpressing IL-17E suggest that this IL-17E ligand (and thus the IL-17 receptor like polypeptides of the present invention which bind to IL-17E) play a role in inflammation, including autoimmune diseases, and in myelopoiesis, particularly in the development, stimulation and/or recruitment of eosinophils and lymphocytes (especially B-lymphocytes). See U.S. provisional patent application Ser. No. 60/266,159 incorporated herein by reference in its entirety, wherein a IL-17E polypeptide was identified to be the ligand for the IL-17 receptor like polypeptides IL-17RB-2 and IL-17RB-3 (SEQ ID NOS: 2 and 5) of the present invention.

One embodiment of the invention provides for methods of identifying inhibitors of an interaction of an IL-17 receptor polypeptide with an IL-17E ligand. These methods comprise the steps of detecting binding of an IL-17 receptor like polypeptide (such as polypeptides comprising the mature protein sequence set out in SEQ ID NOS: 2, 5 or 7 or fragments, analogs or variants thereof that retain ligand-binding activity) to IL-17E ligand (such as a polypeptide comprising the mature protein sequence of SEQ ID NO: 23 or fragments, analogs or variants thereof that retain receptor-binding activity), in the presence and absence of a test compound, and identifying the test compound as a candidate inhibitor when the binding is decreased in the presence of the compound. Suitable test compounds include nucleic acid molecules, proteins, peptides, carbohydrates, lipids, organic and inorganic compounds, libraries of which can be screened using known high throughput screening procedures.

The present invention further provides for methods of treating, preventing or ameliorating a pathological condition mediated by IL-17E comprising administering a therapeutically effective amount of a molecule which specifically binds to either IL-17E ligand or IL-17 receptor like polypeptides of the present invention. The invention also provides for a method of inhibiting undesirable interaction of IL-17 receptor like polypeptide with IL-17E ligand comprising administering a therapeutically effective amount of a molecule capable of binding the IL-17 receptor like polypeptide or IL-17E ligand, or a molecule otherwise capable of inhibiting the interaction between IL-17 receptor-like polypeptide with IL-17E ligand. Candidate inhibitors include selective binding agents (including antibodies or derivatives thereof) that are specific for either IL-17E ligand or IL-17 receptor like polypeptides; analogs, fragments or variants of IL-17 receptor like polypeptides of the present invention (e.g. that retain ligand-binding site(s) of the receptor) and fusion proteins thereof; analogs, fragments or variants of IL-17E ligand (e.g. that retain ability to bind receptor without transducing a signal) and fusion proteins thereof.

Exemplary IL-17E mediated pathological conditions include but are not limited to those conditions related to immune system dysfunction, inflammation (including acute or chronic inflammation), and the progression of cancer. IL-17E polypeptide and polynucleotide may play a role in lymphoma conditions and increased expression of IL-17E polypeptide or polynucleotide may be indicative of a pre-lymphoma state. Other conditions involving IL-17E include infection.

The invention also provides for a method of inhibiting undesirable interaction of IL-17 receptor like polypeptide with IL-17E ligand comprising administering a therapeutically effective amount of a molecule capable of binding the IL-17 receptor like polypeptide or IL-17E ligand.

Methods of regulating expression and modulating (i.e., increasing or decreasing) levels or activity of an IL-17 receptor like polypeptide are also encompassed by the invention. One method comprises administering to an animal a nucleic acid molecule encoding an IL-17 receptor like polypeptide. In another method, a nucleic acid molecule comprising elements that will regulate or modulate the expression of an IL-17 receptor like polypeptide may be administered. Conversely, selective binding agents or antisense oligonucleotides may be administered to treat, prevent or ameliorate pathological conditions related to increased levels or activity of IL-17 receptor like polypeptide. Examples of these methods include gene therapy, cell therapy, and anti-sense therapy as further described herein.

Yeast two-hybrid screens have been extensively used to identify and clone receptors for protein ligands. (Chien et al., Proc. Natl. Acad. Sci. U.S.A., 88: 9578–9583, 1991). The isolation of a IL-17 receptor like polypeptide binding partner is useful for identifying or developing novel agonists and antagonists of the IL-17 receptor like polypeptide activity. Such agonists and antagonists include but are not limited to soluble anti-IL-17 receptor like polypeptides (e.g. fragments lacking all or part of the transmembrane and/or cytoplasmic region(s) or fragments of the extracellular region(s) that retain ligand binding activity, analogs or variants thereof, and fusions thereof to heterologous polypeptides such as constant domains of an immunoglobulin or fragments or variants thereof that retain the ability to prolong half-life in circulation), IL-17 receptor like selective binding agents (such as antibodies and derivatives thereof including chimeric, humanized or human antibodies or fragments thereof that specifically bind to the IL-17 receptor like polypeptide or its ligand-binding sites), small molecules, peptides or derivatives thereof capable of binding IL-17 receptor like polypeptide or its ligand binding site(s) or antisense oligonucleotides (e.g., that specifically bind to IL-17 receptor like encoding DNA or RNA or regulatory sequences and inhibit expression of IL-17 like receptor like polypeptide), any of which can be used for potentially treating one or more diseases or disorders disclosed, including those recited herein.

The invention further encompasses methods for determine the presence of IL-17 receptor like nucleic acids in a biological, tissue or cellular sample. These methods comprise the steps of providing a biological sample suspected of containing IL-17 receptor like nucleic acids; contacting the biological sample with a diagnostic reagent of the present invention under conditions wherein the diagnostic reagent will hybridize with IL-17 receptor like nucleic acids contained in said biological sample; detecting hybridization between nucleic acid in the biological sample and the diagnostic reagent; and comparing the level of hybridization between the biological sample and diagnostic reagent with the level of hybridization between a known concentration of IL-17 receptor like nucleic acid and the diagnostic reagent. The polynucleotide detected in these methods may be an IL-17 receptor like DNA or and IL-17 receptor like RNA.

The invention also provides for a device which comprises a membrane suitable for implantation in a patient; and cells encapsulated within said membrane, wherein said cells secrete an IL-17 receptor like polypeptide of the invention wherein the membrane is permeable to the protein product and impermeable to materials detrimental to said cells. The invention further provides for a device which comprises a membrane suitable for implantation and the IL-17 receptor like polypeptide encapsulated in a membrane that is permeable to the polypeptide The present invention also encompasses diagnostic reagents, including detectably labeled polynucleotides encoding the amino acid sequence of SEQ ID NO: 2, SEQ ID NO: 5 or SEQ ID NO: 7, fragments, variants, homologs thereof. Further, the invention provides for methods of determining the presence of IL-17 receptor like nucleic acids (including DNA and RNA) in biological, cellular and tissue samples by contacting said sample with a diagnostic reagent as described herein that will hybridize with IL-17 receptor like nucleic acid contained in said sample, detecting said hybridization and comparing the level of hybridization between the sample and diagnostic reagent with a the level of hybridization between a known concentration of IL-17 receptor like nucleic acid and the diagnostic reagent.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIGS. 1A–1B depicts a nucleic acid sequence (SEQ ID NO:1) and amino acid sequence (SEQ ID NO:2) of a first human IL-17 receptor like polypeptide.

FIG. 2 depicts homology of a first human IL-17 receptor like polypeptide amino acid sequence (SEQ ID NO:2) and a known IL-17 receptor family member (SEQ ID NO:3).

FIGS. 3A–3B depicts a nucleic acid sequence (SEQ ID NO:4) and amino acid sequence (SEQ ID NO:5) of a second human IL-17 receptor like polypeptide.

FIG. 4 depicts homology of a second human IL-17 receptor like polypeptide amino acid sequence (SEQ ID NO:5) and a known IL-17 receptor family member (SEQ ID NO:3).

FIGS. 5A–5B depicts a nucleic acid sequence (SEQ ID NO:6) and amino acid sequence (SEQ ID NO:7) of a third human IL-17 receptor like polypeptide.

FIG. 6 depicts homology of a third human IL-17 receptor like polypeptide amino acid sequence (SEQ ID NO:7) and a known IL-17 receptor family member (SEQ ID NO:3).

FIG. 7 depicts an overlap of amino acid sequences of the first (SEQ ID NO: 2; IL-17RB-2), second (SEQ ID NO: 5; IL-17RB-3), and third (SEQ ID NO: 7) human IL-17 receptor like polypeptides. The underlined sequence is the predicted transmembrane domain which spans residues 293 to 313 of SEQ ID NO: 2, residues 351 to 371 of SEQ ID NO: 5 and residues 176 to 196 of SEQ ID NO: 7. The predicted signal peptide is in bold which spans residues 14 of SEQ ID NOS: 2 and 5. Therefore the predicted extra-cellular sequence spans amino acids 14 to 292 of SEQ ID NO: 2 and amino acids 14 to 350 of SEQ ID NO: 5.

FIG. 11 depicts hematoxylin and eosin (A,B; E–I) and B220 (C,D) stained sections of lymph bone marrow (A,B), spleen (C—F) and kidney (G–J) from IL-17 like transgenic mice (B,D,F,H,J) or non-transgenic control mice (A,C,E,G, I). Panel A illustrates marked eosinophilic myeloid hyperplasia. Panel D illustrates lymphoid hyperplasia with a predominance of B220 positive B cells (arrows) in the IL-17 like transgenic mouse spleen, while panel F illustrates eosinophilic myeloid hyperplasia in the IL-17 like transgenic splenic red pulp compared to the non-transgenic splenic red pulp (E). Panels H and J illustrate renal pelvic dilation (arrow in H) with a marked eosinophilic inflammatory infiltration in the renal pelvis (pyelonephritis, panel J).

FIG. 22 sets out the sequence of the IL-17RB-2 fusion protein (SEQ ID NO: 24) comprising the extra-cellular domain of IL-17-RB-2 (SEQ ID NO: 2) and the FC fusion peptide (SEQ ID 7. NO: 21). The FC fusion portion of the amino acid sequence is underlined and the native signal peptide of IL-17RB-2 is bold.

FIG. 23 sets out the sequence of the IL-17RB-3 fusion protein (SEQ ID NO: 25) comprising the extra-cellular domain of IL-17-RB-3 (SEQ ID NO: 5) and the FC fusion peptide (SEQ ID NO: 21). The FC fusion portion of the amino acid sequence is underlined and the native signal peptide of IL-17RB-3 is bold.

DETAILED DESCRIPTION OF THE INVENTION

Figure 8:
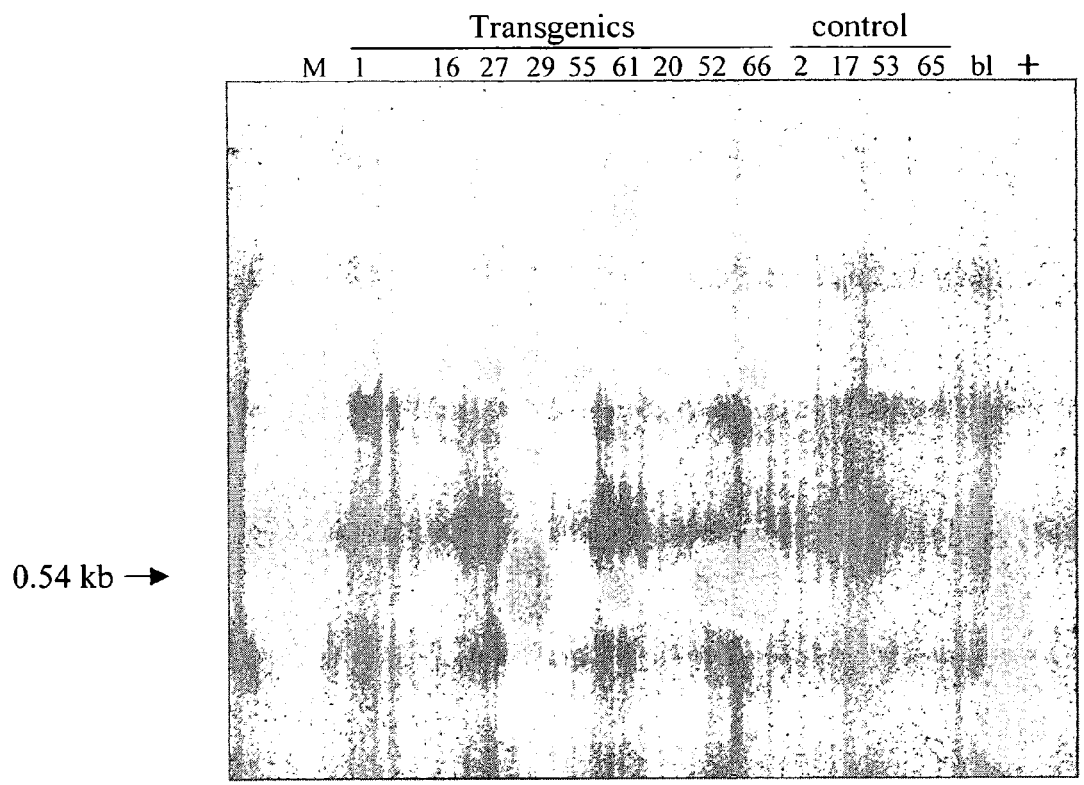
FIG. 8 depicts a Northern blot detecting expression of the IL-17 like overexpressing transgene in necropsied transgenic founder mice (nos. 1, 16, 27, 29, 55, 61, 20, 52, and 66). The control mice (nos. 2, 17, 53 and 65) are non-transgenic littermates. The lane marked "bl" is a blank lane and the positive control (+) was the IL-17 like cDNA. The presence of a 0.54 kb band is indicative of transgene expression.

The section headings used herein are for organizational purposes only and are not to be construed as limiting the subject matter described. All references cited in this application are expressly incorporated by reference herein.

Definitions

The terms "IL-17 receptor like gene" or "IL-17 receptor like nucleic acid molecule" or "polynucleotide" refers to a nucleic acid molecule comprising or consisting of a nucleotide sequence as set forth in any of SEQ ID NO:1, SEQ ID NO:4, or SEQ ID NO:6, including combinations thereof; a nucleotide sequence encoding the polypeptide as set forth in any of SEQ ID NO:2, SEQ ID NO:5, or SEQ ID NO:7, including combinations thereof (such as, but not limited to fusion proteins as described herein); the nucleotide sequences of the DNA insert(s) in Amgen deposit no. A-666A-P (hIL-17r1.1, hIL-17r1.2, and hIL-17r1.3); and nucleic acid molecules as defined herein.

The term "IL-17 receptor like polypeptide" refers to a polypeptide comprising the amino acid sequence of any of SEQ ID NO:2, SEQ ID NO:5, OR SEQ ID NO:7, including combinations thereof, and related polypeptides. Related polypeptides include: IL-17 receptor like polypeptide allelic variants, IL-17 receptor like polypeptide orthologs, IL-17 receptor like polypeptide splice variants, IL-17 receptor like polypeptide variants and IL-17 receptor like polypeptide derivatives. IL-17 receptor like polypeptides may be mature polypeptides, as defined herein, and may or may not have an amino terminal methionine residue, depending on the method by which they are prepared.

The term "IL-17 receptor like polypeptide allelic variant" refers to one of several possible naturally occurring alternate forms of a gene occupying a given locus on a chromosome of an organism or a population of organisms.

The term "IL-17 receptor like polypeptide derivatives" refers to the polypeptide as set forth in any of SEQ ID NO:2, SEQ ID NO:5, OR SEQ ID NO:7, including combinations thereof, IL-17 receptor like polypeptide allelic variants, IL-17 receptor like polypeptide orthologs, IL-17 receptor like polypeptide splice variants, or IL-17 receptor like polypeptide variants, as defined herein, that have been chemically modified. The term "IL-17 receptor like polypeptide fragment" refers to a polypeptide that comprises a truncation at the amino terminus (with or without a leader sequence) and/or a truncation at the carboxy terminus of the polypeptide as set forth in any of SEQ ID NO:2, SEQ ID NO:5, or SEQ ID NO:7, including combinations thereof, IL-17 receptor like polypeptide allelic variants, IL-17 receptor like polypeptide orthologs, IL-17 receptor like polypeptide splice variants and/or an IL-17 receptor like polypeptide variant having one or more amino acid additions or substitutions or internal deletions (wherein the resulting polypeptide is at least 6 amino acids or more in length) as compared to the IL-17 receptor lie polypeptide amino acid sequence set forth in any of SEQ ID NO:2, SEQ F) NO:5, or SEQ ID NO:7, including combinations thereof IL-17 receptor like polypeptide fragments may result from alternative RNA splicing or from in vivo protease activity. For transmembrane or membrane-bound forms of an IL-17 receptor like polypeptide, preferred fragments include soluble forms such as those lacking a transmembrane or membrane binding domain. For example, a soluble fragment of the IL-17 receptor like polypeptide is a polypeptide comprising SEQ ID NO: 2 which lacks amino acids 293 to 313 or a polypeptide comprising SEQ ID NO: 5 which lacks amino acids 351 to 371. Preferred IL-17 receptor like polypeptide fragments retain the ability to bind to IL-17 receptor like polypeptide ligands such as IL-17E of SEQ ID NO: 23. In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such IL-17 receptor like polypeptide fragments may optionally comprise an amino terminal methionine residue. It will be appreciated that such fragments can be used, for example, to generate antibodies to IL-17 receptor like polypeptides.

The term "IL-17 receptor like fusion polypeptide" refers to a fusion of one or more amino acids (such as a heterologous peptide or polypeptide) at the amino or carboxy terminus of the polypeptide as set forth in any of SEQ ID NO:2, SEQ ID NO:5, or SEQ ID NO:7, including combinations thereof, IL-17 receptor like polypeptide allelic variants, IL-17 receptor like polypeptide orthologs, IL-17 receptor like polypeptide splice variants, or IL-17 receptor like polypeptide variants having one or more amino acid deletions, substitutions or internal additions as compared to the IL-17 receptor like polypeptide amino acid sequence set forth in any of SEQ ID NO:2, SEQ ID NO:5, or SEQ ID NO:7, including combinations thereof. It will be appreciated that fusion proteins include combinations of polypeptide amino acid sequence as set forth in any of SEQ ID NO:2, SEQ ID NO:5, or SEQ ID NO:7.

The term "IL-17 receptor like polypeptide ortholog" refers to a polypeptide from another species that corresponds to IL-17 receptor like polypeptide amino acid sequence as set forth in any of SEQ ID NO:2, SEQ ID NO:5, or SEQ ID NO:7, including combinations thereof. For example, mouse and human IL-17 receptor like polypeptides are considered orthologs of each other.

The term "IL-17 receptor like polypeptide splice variant" refers to a nucleic acid molecule, usually RNA, which is generated by alternative processing of intron sequences in an RNA transcript of IL-17 receptor like polypeptide amino acid sequence as set forth in any of SEQ ID NO:2, SEQ ID NO: 5, or SEQ ID NO:7, including combinations thereof.

The term "IL-17 receptor like polypeptide variants" refers to IL-17 receptor like polypeptides comprising amino acid sequences having one or more amino acid sequence substitutions, deletions (such as internal deletions and/or IL-17 receptor like polypeptide fragments), and/or additions (such as internal additions and/or IL-17 receptor like fusion polypeptides) as compared to the IL-17 receptor like polypeptide amino acid sequence set forth in any of SEQ ID NO:2, SEQ ID NO:5, OR SEQ ID NO:7, including combinations thereof (with or without a leader sequence). Variants may be naturally occurring (e.g., IL-17 receptor like polypeptide allelic variants, IL-17 receptor like polypeptide orthologs and IL-17 receptor like polypeptide splice variants) or artificially constructed. Such IL-17 receptor like polypeptide variants may be prepared from the corresponding nucleic acid molecules having a DNA sequence that varies accordingly from the DNA sequence as set forth in any of SEQ ID NO:1, SEQ ID NO:4, OR SEQ ID NO:6, including combinations thereof. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term specific binding reaction referred to above is meant to indicate that the antigen will react, in a highly selective manner, with its corresponding antibody and not with the multitude of other antibodies which can be evoked by other antigens.

The term "biologically active IL-17 receptor like polypeptides" refers to IL-17 receptor like polypeptides having at least one activity characteristic of the polypeptide comprising the amino acid sequence of any of SEQ ID NO:2, SEQ ID NO:5, or SEQ ID NO:7, including combinations thereof.

The terms "effective amount" and "therapeutically effective amount" each refer to the amount of a IL-17 receptor like polypeptide or IL-17 receptor like nucleic acid molecule used to support an observable level of one or more biological activities of the IL-17 receptor like polypeptides as set forth herein.

The term "expression vector" refers to a vector which is suitable for use in a host cell and contains nucleic acid sequences which direct and/or control the expression of inserted heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptides will be higher than the percent identity between those two polypeptides.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from at least one contaminating nucleic acid molecule with which it is naturally associated. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates or other materials with which it is naturally found when isolated from the cell source, (2) is not linked (by covalent or noncovalent interaction) to all or a portion of a polypeptide to which the "isolated polypeptide" is linked to in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "mature IL-17 receptor like polypeptide" refers to an IL-17 receptor like polypeptide lacking a leader sequence. A mature IL-17 receptor like polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refers to one or more formulation materials suitable for accomplishing or enhancing the delivery of the IL-17 receptor like polypeptide, IL-17 receptor like nucleic acid molecule or IL-17 receptor like selective binding agent as a pharmaceutical composition.

The term "selective binding agent" refers to a molecule or molecules having specificity for an IL-17 receptor like polypeptide. Selective binding agents include antibodies, such as polyclonal antibodies, monoclonal antibodies (mABs), chimeric antibodies, CDR-grafted antibodies, anti-idiotypic (anti-Id) antibodies to antibodies that can be labeled in soluble or bound forms, as well as fragments, regions, or derivatives thereof which are provided by known techniques, including, but not limited to enzymatic cleavage, peptide synthesis, or recombinant techniques.

IL-17 receptor like polypeptides, fragments, variants, and derivatives may be used to prepare IL-17 receptor like selective binding agents using methods known in the art. Thus, antibodies and antibody fragments that bind IL-17 receptor like polypeptides are within the scope of the present invention. Antibody fragments include those portions of the antibody which bind to an epitope on the IL-17 receptor like polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions. These antibodies may be, for example, polyclonal monospecific polyclonal, monoclonal, recombinant, chimeric, humanized, human, single chain, and/or bispecific.

As used herein, the terms, "specific" and "specificity" refer to the ability of the selective binding agents to bind to human IL-17 receptor like polypeptides and not to bind to human non-IL-17 receptor like polypeptides. It will be appreciated, however, that the selective binding agents may also bind orthologs of the polypeptide as set forth in any of SEQ ID NO:2, SEQ ID NO:5, or SEQ ID NO:7, including combinations thereof, that is, interspecies versions thereof, such as mouse and rat polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52:456 (1973); Sambrook et al., *Molecular Cloning, a laboratory Manual*, Cold Spring Harbor Laboratories (New York, 1989); Davis et al., *Basic Methods in Molecular Biology*, Elsevier, 1986; and Chu et al., *Gene*, 13:197 (1981). Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "vector" is used to refer to any molecule (e.g., nucleic acid, plasmid, or virus) used to transfer coding information to a host cell.

Relatedness of Nucleic Acid Molecules and/or Polypeptides

It is understood that related nucleic acid molecules include allelic or splice variants of the nucleic acid molecule of any of SEQ ID NO:1, SEQ ID NO:4, or SEQ ID NO:6, including combinations thereof; and include sequences which are complementary to any of the above nucleotide sequences. Related nucleic acid molecules also include a nucleotide sequence encoding a polypeptide comprising or consisting essentially of a substitution, modification, addition and/or a deletion of one or more amino acid residues compared to the polypeptide in any of SEQ ID NO:2, SEQ ID NO:5, or SEQ ID NO:7, including combinations thereof.

Fragments include molecules which encode a polypeptide of at least about 25 amino acid residues, or about 50, or about 75, or about 100, or greater than about 100 amino acid residues of the polypeptide of any of SEQ ID NO:2, SEQ ID NO:5, or SEQ ID NO:7, including combinations thereof.

In addition, related IL-17 receptor like nucleic acid molecules include those molecules which comprise nucleotide sequences which hybridize under moderately or highly stringent conditions as defined herein with the fully complementary sequence of the nucleic acid molecule of any of SEQ ID NO:1, SEQ ID NO:4, or SEQ ID NO:6, including combinations thereof, or of a molecule encoding a polypeptide, which polypeptide comprises the amino acid sequence as shown in any of SEQ ID NO:2, SEQ ID NO:5, or SEQ ID NO:7, including combinations thereof, or of a nucleic acid fragment as defined herein, or of a nucleic acid fragment encoding a polypeptide as defined herein. Hybridization probes may be prepared using the IL-17 receptor like sequences provided herein to screen cDNA, genomic or synthetic DNA libraries for related sequences. Regions of the DNA and/or amino acid sequence of IL-17 receptor like polypeptide that exhibit significant identity to known sequences are readily determined using sequence alignment algorithms as described herein and those regions may be used to design probes for screening.

The term "highly stringent conditions' refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65–68° C. or 0.015M sodium chloride, 0.0015M sodium citrate, and 50% formamide at 42° C. See Sambrook, Fritsch & Maniatis, Molecular Cloning: A Laboratory Manual, $2^{nd}$ Ed., Cold Spring Harbor Laboratory, (Cold Spring Harbor, N.Y. 1989); Anderson et al., Nucleic Acid Hybridisation: a practical approach, Ch. 4, IRL Press Limited (Oxford, England).

More stringent conditions (such as higher temperature, lower ionic strength, higher formamide, or other denaturing agent) may also be used, however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecyl-sulfate (NaDodSO$_4$ or SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8–7.4, however, at typical ionic strength conditions, the rate of hybridization is nearly independent of pH. See Anderson et al., Nucleic Acid Hybridisation: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log[Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015M sodium chloride, 0.0015M sodium citrate at 50–65° C. or 0.015M sodium chloride, 0.0015M sodium citrate, and 20% formamide at 37–50° C. By way of example, a "moderately stringent" condition of 50° C. in 0.015 M sodium ion will allow about a 21% mismatch.

It will be appreciated by those skilled in the art that there is no absolute distinction between lhighly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$T_m=2° \text{ C. per } A\text{-}T \text{ base pair}+4° \text{ C. per } G\text{-}C \text{ base pair}$$

The sodium ion concentration in 6× salt sodium citrate (SSC) is 1M. See Suggs et al., Developmental Biology Using Purified Genes, p. 683, Brown and Fox (eds.) (1981).

High stringency washing conditions for oligonucleotides are usually at a temperature of 0–5° C. below the Tm of the oligonucleotide in 6×SSC, 0.1% SDS.

In another embodiment, related nucleic acid molecules comprise or consist of a nucleotide sequence that is about 70 percent identical to the nucleotide sequence as shown in any of SEQ ID NO:1, SEQ ID NO:4, or SEQ ID NO:6, including combinations thereof, or comprise or consist essentially of a nucleotide sequence encoding a polypeptide that is about 70 percent identical to the polypeptide as set forth in any of SEQ ID NO:2, SEQ ID NO:5, or SEQ ID NO:7, including combinations thereof. In preferred embodiments, the nucleotide sequences are about 75 percent, or about 80 percent, or about 85 percent, or about 90 percent, or about 95, 96, 97, 98, or 99 percent identical to the nucleotide sequence as shown in any of SEQ ID NO:1, SEQ ID NO:4, or SEQ ID NO:6, including combinations thereof, or the nucleotide sequences encode a polypeptide that is about 75 percent, or about 80 percent, or about 85 percent, or about 90 percent, or about 95, 96, 97, 98, or 99 percent identical to the polypeptide sequence as set forth in any of SEQ ID NO:2, SEQ ID NO:5, or SEQ ID NO:7, including combinations thereof.

Differences in the nucleic acid sequence may result in conservative and/or non-conservative modifications of the amino acid sequence relative to the amino acid sequence of any of SEQ ID NO:2, SEQ ID NO:5, or SEQ ID NO:7, including combinations thereof.

Conservative modifications to the amino acid sequence of any of SEQ ID NO: 2, SEQ ID NO: 5, or SEQ ID NO: 7, including combinations thereof (and the corresponding modifications to the encoding nucleotides) will produce IL-17 receptor like polypeptides having functional and chemical characteristics similar to those of naturally occurring IL-17 receptor like polypeptide. In contrast, substantial modifications in the functional and/or chemical characteristics of IL-17 receptor like polypeptides may be accomplished by selecting substitutions in the amino acid sequence of any of SEQ ID NO:2, SEQ ID NO:5, or SEQ ID NO:7, including combinations thereof, that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties:
 1) hydrophobic: norleucine, Met, Ala, Val, Leu, Ile;
 2) neutral hydrophilic: Cys, Ser, Thr, Asn, Gln;
 3) acidic: Asp, Glu;
 4) basic: His, Lys, Arg;
 5) residues that influence chain orientation: Gly, Pro; and
 6) aromatic: Trp, Tyr, Phe.

For example, non-conservative substitutions may involve the exchange of a member of one of these classes for a member from another class. Such substituted residues may be introduced into regions of the human IL-17 receptor like polypeptide that are homologous with non-human IL-17 receptor like polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105–131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the IL-17 receptor like polypeptide, or to increase or decrease the affinity of the IL-17 receptor like polypeptides described herein.

Exemplary amino acid substitutions are set forth in Table I.

| Amino Acid Substitutions | | |
| --- | --- | --- |
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NO:2, SEQ ID NO:5, or SEQ ID NO:7, including combinations thereof, using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an IL-17 receptor like polypeptide to such similar polypeptides. With such a comparison, one can identify residues and portions of the molecules that are conserved among similar polypeptides. It will be appreciated that changes in areas of an IL-17 receptor like polypeptide that are not conserved relative to such similar polypeptides would be less likely to adversely affect the biological activity and/or structure of the IL-17 receptor like polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of IL-17 receptor like polypeptide to such similar polypeptides. After making such a comparison, one skilled in the art can determine residues and portions of the molecules that are conserved among similar polypeptides. One skilled in the art would know that changes in areas of the IL-17 receptor like molecule that are not conserved would be less likely to adversely affect the biological activity and/or structure of a IL-17 receptor like polypeptide. One skilled in the art would also know that, even in relatively conserved regions, one may substitute chemically similar amino acids for the naturally occurring residues while retaining activity (conservative amino acid residue substitutions).

Additionally, one skilled in the art can review structure-function studies identifying residues in similar polypeptides that are important for activity or structure. In view of such a comparison, one can predict the importance of amino acid residues in an IL-17 receptor like polypeptide that correspond to amino acid residues that are important for activity or structure in similar polypeptides. One skilled in the art may opt for chemically similar amino acid substitutions for such predicted important amino acid residues of IL-17 receptor like polypeptides.

One skilled in the art can also analyze the three-dimensional structure and amino acid sequence in relation to that structure in similar polypeptides. In view of that information, one skilled in the art may predict the alignment of amino acid residues of an IL-17 receptor like polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure, and to the identification of epitopes, from analyses of amino acid sequences. See Chou et al., Biochemistry, 13 (2):222–245 (1974); Chou et al., Biochemistry, 113 (2):211–222 (1974); Chou et al., Adv. Enzymol. Relat. Areas Mol. Biol., 47:45–148 (1978); Chou et al., Ann. Rev. Biochem., 47:251–276 and Chou et al., Biophys. J., 26:367–384 (1979). Moreover, computer programs are currently available to assist with predicting antigenic portions and epitopic core regions of proteins. Examples include those programs based upon the. Examples include those programs based upon the Jameson-Wolf analysis (Jameson et al., Comput. Appl. Biosci., 4(1):181–186 (1998) and Wolf et al., Comput. Appl. Biosci., 4(1):187–191 (1988), the program PepPlot® (Brutlag et al., CABS, 6:237–245 (1990), and Weinberger et al., Science, 228: 740–742 (1985), and other new programs for protein tertiary structure prediction (Fetrow et al., Biotechnology, 11:479–483 (1993).

Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1):244–247 (1999). It has been suggested (Brenner et al., Curr. Op. Struct. Biol., 7(3):369–376 (1997)) that there are a limited number of folds in a given polypeptide or protein and that once a critical number of structures have been resolved, structural prediction will gainbecome dramatically in accuracy more accurate.

Additional methods of predicting secondary structure include "threading" (Jones, D., *Curr. Opin. Struct. Bol.,* 7(3):377–87 (1997); Sippl et al., *Structure,* 4(1):15–9 (1996)), "profile analysis" (Bowie et al., *Science,* 253: 164–170 (1991); Gribskov et al., *Meth. Enzym.,* 183:146–159 (1990); Gribskov et al., *Proc. Nat. Acad. Sci.,* 84(13):4355–4358 (1987)), and "evolutionary linkage" (See Home, supra, and Brenner, supra).

IL-17 receptor like polypeptide analogs of the invention can be determined by comparing the amino acid sequence of IL-17 receptor like polypeptide with related family members. An exemplary IL-17 receptor like polypeptide related family member is human IL-17 receptor polypeptide as set out in SEQ ID NO: 3. This comparison can be accomplished by using a Pileup alignment (Wisconsin GCG Program Package) or an equivalent (overlapping) comparison with multiple family members within conserved and non-conserved regions.

As shown in FIGS. 2, 4 and 6, the predicted amino acid sequences of human IL-17 receptor like polypeptides (SEQ ID NOS: 2, 5 and 7)are aligned with a known human IL-17 receptor family member (SEQ ID NO: 3) respectively. Other IL-17 receptor like polypeptide analogs can be determined using these or other methods known to those of skill in the art. These overlapping sequences provide guidance for conservative and non-conservative amino acids substitutions resulting in additional IL-17 receptor like analogs. It will be appreciated that these amino acid substitutions can consist of naturally occurring or non-naturally occurring amino acids. For example, potential IL-17 receptor like analogs may have the Met at residue at position 167 of SEQ ID NO: 2, position 225 of SEQ ID NO: 5 or position 50 of SEQ ID NO: 7 substituted with a Leu, Ile, or Phe residue; the Cys residue at position 261 of SEQ ID NO: 2, position 319 of SEQ ID NO: 5 or position 144 of SEQ ID No: 7 substituted with a Ser or Ala residue; and/or the Leu residue at position 299 of SEQ ID NO: 2, position 357 of SEQ ID NO: 5 or position 212 of SEQ ID No: 7 substituted with a norleucine, Gln, Asn, Arg, 1,4, or Diamino-butyric Acid. In addition, potential IL-17 receptor like analogs may have the Trp residue at position 313 of SEQ ID NO: 2, position 371 of SEQ ID NO: 5 or position 196 of SEQ ID NO: 7 substituted with a Tyr or Phe residue; the Gly residue at position 413 of SEQ ID NO: 2, position 471 of SEQ ID NO: 5 or position 296 of SEQ ID NO: 7 substituted with a Pro or Ala residue; and/or the Asp residue at position 433 of SEQ ID NO: 2, position 491 of SEQ ID No: 5 or position 313 of SEQ ID No: 7 substituted with a Glu residue.

Preferred IL-17 receptor like polypeptide variants include glycosylation variants wherein the number and/or type of glycosylation sites has been altered compared to the amino acid sequence set forth in any of SEQ ID NO:2, SEQ ID NO:5, or SEQ ID NO:7, including combinations thereof. In one embodiment, IL-17 receptor like polypeptide variants comprise a greater or a lesser number of N-linked glycosylation sites than the amino acid sequence set forth in any of SEQ ID NO:2, SEQ ID NO:5, or SEQ ID NO:7, including combinations thereof. An N-linked glycosylation site is characterized by the sequence: Asn-X-Ser or Asn-X-Thr, wherein the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred IL-17 receptor like variants include cysteine variants, wherein one or more cysteine residues are deleted from or substituted for another amino acid (e.g., serine) as compared to the amino acid sequence set forth in any of SEQ ID NO:2, SEQ ID NO:5, or SEQ ID NO:7, including combinations thereof. Cysteine variants are useful when IL-17 receptor like polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, the polypeptide comprising the amino acid sequence of any of SEQ ID NO: 2, SEQ ID NO:5, or SEQ ID NO: 7, including combinations thereof, or an IL-17 receptor like polypeptide variant, including a fragment and/or derivative, may be fused to a homologous polypeptide to form a homodimer or to a heterologous polypeptide to form a heterodimer. Heterologous peptides and polypeptides include, but are not limited to: an epitope to allow for the detection and/or isolation of an IL-17 receptor like fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in any of SEQ ID NO:2, SEQ ID NO:5, or SEQ ID NO:7, including combinations thereof, or an IL-17 receptor like polypeptide variant.

Fusions can be made either at the amino terminus or at the carboxy terminus of the polypeptide comprising the amino acid sequence set forth in any of SEQ ID NO:2, SEQ ID NO:5, or SEQ ID NO:7, including combinations thereof, or an IL-17 receptor like polypeptide variant. Fusions may be direct with no linker or adapter molecule or indirect using a linker or adapter molecule. A linker or adapter molecule may be one or more amino acid residues, typically up to about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of any of SEQ ID NO:2, SEQ ID NO:5, OR SEQ ID NO:7, including combinations thereof, or an IL-17 receptor like polypeptide variant is fused to one or more domains of an Fc region of human IgG. Antibodies comprise two functionally independent parts, a variable domain known as "Fab", which binds antigen, and a constant domain known as "Fc", which is involved in effector functions such as complement activation and attack by phagocytic cells. An Fc has a long serum half-life, whereas an Fab is short-lived. Capon et al., *Nature*, 337:525–31 (1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art, including materials and methods applicable to the production of fused IL-17 receptor like polypeptide.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol., 154: 5590–5600 |
| IgG1 | TNF receptor | septic shock | Fisher et al. (1996), N. Engl. J. Med., 334: 1697–1702; Van Zee et al., (1996), J. Immunol., 156: 2221–2230 |
| IgG, IgA, IgM, or IgE (excluding the first domain) | TNF receptor | inflammation, autoimmune disorders | U.S. Pat. No. 5,808,029, issued Sept. 15, 1998 |
| IgG1 | CD4 receptor | AIDS | Capon et al. (1989), Nature 337: 525–531 |
| IgG1, IgG3 | N-terminus of IL-2 | anti-cancer, antiviral | Harvill et al. (1995) Immunotech., 1: 95–105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med., 174: 561–569 |

In one example, all or a portion of the human IgG hinge, CH2 and CH3 regions may be fused at either the N-terminus or C-terminus of the IL-17 receptor like polypeptides using methods known to the skilled artisan. In another example, a portion of hinge regions and CH2 and CH3 regions may be fused. The resulting IL-17 receptor like polypeptide-Fc fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in Computational *Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo et al., SIAM *J. Applied Math.*, 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis.), BLASTP, BLASTN, and FASTA (Altschul et al., *J. Mol. Biol.*, 215:403–410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., *Proc. Natl. Acad. Sci USA*, 89:10915–10919 (1992) for the BLOSUM 62 comparison matrix) is also used by the algorithm.

Preferred parameters for a polypeptide sequence comparison include the following:
Algorithm: Needleman et al., *J. Mol. Biol.*, 48:443–453 (1970);
Comparison matrix: BLOSUM 62 from Henikoff et al., Proc. Natl. Acad. Sci. USA, 89:10915–10919 (1992);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:
Algorithm: Needleman et al., J. Mol. Biol., 48:443–453 (1970);
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art the nucleic acid and polypeptide molecules described herein may be produced by recombinant and other means.

Nucleic Acid Molecules

The nucleic acid molecules encode a polypeptide comprising the amino acid sequence of an IL-17 receptor like polypeptide can readily be obtained in a variety of ways including, without limitation, chemical synthesis, cDNA or genomic library screening, expression library screening and/or PCR amplification of cDNA.

Recombinant DNA methods used herein are generally those set forth in Sambrook et al., *Molecular Cloning: A Laboratory Manual*, Cold Spring Harbor Laboratory Press, Cold Spring Harbor, N.Y. (1989), and/or Ausubel et al., eds., *Current Protocols in Molecular Biology*, Green Publishers Inc. and Wiley and Sons, NY (1994). The present invention provides for nucleic acid molecules as described herein and methods for obtaining the molecules.

A gene or cDNA encoding a IL-17 receptor like polypeptide or fragment thereof may be obtained by hybridization screening of a genomic or cDNA library, or by PCR amplification. Where a gene encoding the amino acid sequence of an IL-17 receptor like polypeptide has been identified from one species, all or a portion of that gene may be used as a probe to identify corresponding genes from other species (orthologs) or related genes from the same species. The probes or primers may be used to screen cDNA libraries from various tissue sources believed to express the IL-17 receptor like polypeptide. In addition, part or all of a nucleic acid molecule having the sequence as set forth in any of SEQ ID NO:1, SEQ ID NO:4, OR SEQ ID NO:6, including combinations thereof may be used to screen a genomic library to identify and isolate a gene encoding the amino acid sequence of an IL-17 receptor like polypeptide. Typically, conditions of moderate or high stringency will be employed for screening to minimize the number of false positives obtained from the screen.

Nucleic acid molecules encoding the amino acid sequence of IL-17 receptor like polypeptides may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of an IL-17 receptor like polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an IL-17 receptor like polypeptide can be inserted into an expression vector. By introducing the expression vector into an appropriate host, the encoded IL-17 receptor like polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the amino acid sequence of an IL-17 receptor like polypeptide, are then added to the cDNA along with a polymerase such as Taq polymerase, and the polymerase amplifies the cDNA region between the two primers.

Another means of preparing a nucleic acid molecule encoding the amino acid sequence of an IL-17 receptor like polypeptide, including a fragment or varaint, is chemical synthesis using methods well known to the skilled artisan such as those described by Engels et al., *Angew. Chem. Intl. Ed.*, 28:716–734 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of an IL-17 receptor like polypeptide will be several hundred nucleotides in length. Nucleic acids larger than about 100 nucleotides can be synthesized as several fragments using these methods. The fragments can then be ligated together to form the full length nucleotide sequence of an IL-17 receptor like polypeptide. Usually, the DNA fragment encoding the amino terminus of the polypeptide will have an ATG, which encodes a methionine residue. This methionine may or may not be present on the mature form of the IL-17 receptor like polypeptide, depending on whether the polypeptide produced in the host cell is designed to be secreted from that cell. Other methods known to the skilled artisan may be used as well.

In some cases, it may be desirable to prepare nucleic acid molecules encoding IL-17 receptor like polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In certain embodiments, nucleic acid variants contain codons which have been altered for the optimal expression of an IL-17 receptor like polypeptide in a given host cell. Particular codon alterations will depend upon the IL-17 receptor like polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "*Drosophila*_high.cod", "Human_high.cod", "Maize_high.cod", and "Yeast_high.cod".

In other embodiments, nucleic acid molecules encode IL-17 receptor like variants with conservative amino acid substitutions as described herein, IL-17 receptor like variants comprising an addition and/or a deletion of one or more N-linked or O-linked glycosylation sites, IL-17 receptor like variants having deletions and/or substitutions of one or more cysteine residues, or IL-17 receptor like polypeptide fragments as described herein. In addition, nucleic acid molecules may encode any combination of IL-17 receptor like variants, fragments, and fusion polypeptides described herein.

Vectors and Host Cells

A nucleic acid molecule encoding the amino acid sequence of an IL-17 receptor like polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an IL-17 receptor like polypeptide may be amplified/expressed in prokaryotic, yeast, insect (baculovirus systems), and/or eukaryotic host cells. Selection of the host cell will depend in part on whether an IL-17 receptor like polypeptide is to be post-translationally modified (e.g., glycosylated and/or phosphorylated). If so, yeast, insect, or mammalian host cells are preferable. For a review of expression vectors, see *Meth. Enz.*, v.185, D. V. Goeddel, ed. Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-17 receptor like polypeptide coding sequence; the oligonucleotide sequence encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the IL-17 receptor like polypeptide from the host cell. Affinity purification can be accomplished, for example, by column chromatography using antibodies against the tag as an affinity matrix. Optionally, the tag can subsequently be removed from the purified IL-17 receptor like polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source) or synthetic, or the flanking sequences may be native sequences which normally function to regulate IL-17 receptor like polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than the IL-17 receptor like gene flanking sequences will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an IL-17 receptor like polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an IL-17 receptor like polypeptide. As a result, increased quantities of IL-17 receptor like polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of an IL-17 receptor like polypeptide to be expressed. The Shine-Dalgarno sequence is varied but is typically a polypurine (i.e., having a high A–G content). Many Shine-Dalgarno sequences have been identified, each of which can be readily synthesized using methods set forth herein and used in a prokaryotic vector.

A leader, or signal, sequence may be used to direct an IL-17 receptor like polypeptide out of the host cell. Typically, a nucleotide sequence encoding the signal sequence is positioned in the coding region of an IL-17 receptor like nucleic acid molecule, or directly at the 5' end of an IL-17 receptor like polypeptide coding region. Many signal sequences have been identified, and any of those that are functional in the selected host cell may be used in conjunction with an IL-17 receptor like nucleic acid molecule. Therefore, a signal sequence may be homologous (naturally occurring such as amino acids 1 to 14 of SEQ ID NOS: 2 and 5) or heterologous to an IL-17 receptor like gene or cDNA. Additionally, a signal sequence may be chemically synthesized using methods described herein. In most cases, the secretion of an IL-17 receptor like polypeptide from the host cell via the presence of a signal peptide will result in the removal of the signal peptide from the secreted IL-17 receptor like polypeptide. The signal sequence may be a component of the vector, or it may be a part of an IL-17 receptor like nucleic acid molecule that is inserted into the vector.

Included within the scope of this invention is the use of either a nucleotide sequence encoding a native IL-17 receptor like polypeptide signal sequence joined to an IL-17 receptor like polypeptide coding region or a nucleotide sequence encoding a heterologous signal sequence joined to an IL-17 receptor like polypeptide coding region. The heterologous signal sequence selected should be one that is recognized and processed, i.e., cleaved by a signal peptidase, by the host cell. For prokaryotic host cells that do not recognize and process the native IL-17 receptor like polypeptide signal sequence, the signal sequence is substituted by a prokaryotic signal sequence selected, for example, from the group of the alkaline phosphatase, penicillinase, or heat-stable enterotoxin II leaders. For yeast secretion, the native IL-17 receptor like polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired IL-17 receptor like polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the IL-17 receptor like gene, especially where the gene used is a full length genomic sequence or a fragment thereof. Where the intron is not naturally occurring within the gene (as for most cDNAs), the intron(s) may be obtained from another source. The position of the intron with respect to flanking sequences and the IL-17 receptor like gene is generally important, as the intron must be transcribed to be effective. Thus, when an IL-17 receptor like cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding a IL-17 receptor like polypeptide. Promoters are untranscribed sequences located upstream (5') to the start codon of a structural gene (generally within about 100 to 1000 bp) that control the transcription of the structural gene. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding an IL-17 receptor like polypeptide by removing the promoter from the source DNA by restriction enzyme digestion and inserting the desired promoter sequence into the vector. The native IL-17 receptor like gene promoter sequence may be used to direct amplification and/or expression of an IL-17 receptor like nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling IL-17 receptor like gene transcription include, but are not limited to: the SV40 early promoter region (Bernoist and Chambon, *Nature,* 290:304–310, 1981); the CMV promoter; the promoter contained in the 3' long terminal repeat of Rous sarcoma virus (Yamamoto et al., *Cell,* 22:787–797, 1980); the herpes thymidine kinase promoter (Wagner et al., *Proc. Natl. Acad. Sci. USA,* 78:144–1445, 1981); the regulatory sequences of the metallothionine gene (Brinster et al., *Nature,* 296:39–42, 1982); prokaryotic expression vectors such as the beta-lactamase promoter (Villa-Kamaroff, et al., *Proc. Natl. Acad. Sci. USA,* 75:3727–3731, 1978); or the tac promoter (DeBoer, et al., *Proc. Natl. Acad. Sci. USA,*

80:21–25, 1983). Also of interest are the following animal transcriptional control regions, which exhibit tissue specificity and have been utilized in transgenic animals: the elastase I gene control region which is active in pancreatic acinar cells (Swift et al., *Cell*, 38:639–646, 1984; Ornitz et al., Cold Spring Harbor *Symp. Quant. Biol.*, 50:399–409 (1986); MacDonald, *Hepatology*, 7:425–515, 1987); the insulin gene control region which is active in pancreatic beta cells (Hanahan, *Nature*, 315:115–122, 1985); the immunoglobulin gene control region which is active in lymphoid cells (Grosschedl et al., *Cell*, 38:647–658 (1984); Adames et al., *Nature*, 318:533–538 (1985); Alexander et al., *Mol. Cell. Biol.*, 7:1436–1444, 1987); the mouse mammary tumor virus control region which is active in testicular, breast, lymphoid and mast cells (Leder et al., *Cell*, 45:485–495, 1986); the albumin gene control region which is active in liver (Pinkert et al., *Genes and Devel.*, 1:268–276, 1987); the alphafetoprotein gene control region which is active in liver (Krumlauf et al., *Mol. Cell. Biol.*, 5:1639–1648, 1985; Hammer et al., *Science*, 235:53–58, 1987); the alpha 1-antitrypsin gene control region which is active in the liver (Kelsey et al., *Genes and Devel.*, 1:161–171, 1987); the beta-globin gene control region which is active in myeloid cells (Mogram et al., *Nature*, 315:338–340, 1985; Kollias et al., *Cell*, 46:89–94, 1986); the myelin basic protein gene control region which is active in oligodendrocyte cells in the brain (Readhead et al., *Cell*, 48:703–712, 1987); the myosin light chain-2 gene control region which is active in skeletal muscle (Sani, *Nature*, 314:283–286, 1985); and the gonadotropic releasing hormone gene control region which is active in the hypothalamus (Mason et al., *Science*, 234:1372–1378, 1986).

An enhancer sequence may be inserted into the vector to increase the transcription of a DNA encoding an IL-17 receptor like polypeptide of the present invention by higher eukaryotes. Enhancers are cis-acting elements of DNA, usually about 10–300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an IL-17 receptor like nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), PBSII (Stratagene Company, La Jolla, Calif.), pET15 (Novagen, Madison, Wis.), PGEX (Pharmacia Biotech, Piscataway, N.J.), pEGFP—N2 (Clontech, Palo Alto, Calif.), PETL (BlueBacII; Invitrogen), pDSR-alpha (PCT Publication No. WO90/14363) and pFastBacDual (Gibco/BRL, Grand Island, N.Y.).

Additional suitable vectors include, but are not limited to, cosmids, plasmids or modified viruses, but it will be appreciated that the vector system must be compatible with the selected host cell. Such vectors include, but are not limited to plasmids such as BLUESCRIPT® plasmid derivatives (a high copy number ColE 1-based phagemid, Stratagene Cloning Systems Inc., La Jolla Calif.), PCR cloning plasmids designed for cloning Taq-amplified PCR products (e.g., TOPO™ TA Cloning® Kit, PCR2.1 plasmid derivatives, Invitrogen, Carlsbad, Calif.), and mammalian, yeast, or virus vectors such as a baculovirus expression system (pBacPAK plasmid derivatives, Clontech, Palo Alto; CA). The recombinant molecules can be introduced into host cells via transformation, transfection, infection, or other known techniques.

After the vector has been constructed and a nucleic acid molecule encoding an IL-17 receptor like polypeptide has been inserted into the proper site of the vector, the completed vector may be inserted into a suitable host cell for amplification and/or polypeptide expression. The transformation of an expression vector for an IL-17 receptor like polypeptide into a selected host cell may be accomplished by well known methods including methods such as transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast cell, an insect cell or a vertebrate cell). The host cell, when cultured under appropriate conditions, synthesizes an IL-17 receptor like polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA*, 97:4216–4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques*, 14:810–817 (1993); Lucklow, *Curr. Opin. Biotechnol.*, 4:564–572 (1993); and Lucklow et al. (*J. Virol.*, 67:4566–4579 (1993). Preferred insect cells are Sf-9 and HiS (Invitrogen, Carlsbad, Calif.).

One may also use transgenic animals to express glycosylated IL-17 receptor like polypeptides. For example, one may use a transgenic milk-producing animal (a cow or goat, for example) and obtain the present glycosylated polypeptide in the animal milk. One may also use plants to produce IL-17 receptor like polypeptides, however, in general, the glycosylation occurring in plants is different from that produced in mammalian cells, and may result in a glycosylated product which is not suitable for human therapeutic use.

Polypeptide Production

Host cells comprising an IL-17 receptor like polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of an IL-17 receptor like polypeptide produced by a host cell can be evaluated using standard methods known in the art. Such methods include, without limitation, Western blot analysis, SDS-polyacrylamide gel electrophoresis, non-denaturing gel electrophoresis, high performance liquid chromatography (HPLC)separation, immunoprecipitation, and/or activity assays such as DNA binding gel shift assays.

If an IL-17 receptor like polypeptide has been designed to be secreted from the host cells, the majority of polypeptide may be found in the cell culture medium. If however, the IL-17 receptor like polypeptide is not secreted from the host cells, it will be present in the cytoplasm and/or the nucleus (for eukaryotic host cells) or in the cytosol (for bacterial host cells). The host cells are typically disrupted mechanically or with a detergent to release the intracellular contents into a buffered solution. Il-17 receptor like polypeptide can then be isolated from the solution.

For an IL-17 receptor like polypeptide situated in the host cell cytoplasm and/or the nucleus (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an IL-17 receptor like polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The IL-17 receptor like polypeptide in its now soluble form can then be analyzed using gel electrophoresis, immunoprecipitation or the like. If it is desired to isolate the IL-17 receptor like polypeptide, isolation may be accomplished using standard methods such as those described herein and in Marston et al., *Meth. Enz.*, 182:264–275 (1990).

In some cases, an IL-17 receptor like polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the proteini's cysteine bridge(s). Some of the commonly used redox couples include cysteine/cystamine, glutathione (GSH)/dithiobis GSH, cupric chloride, dithiothreitol(DTT)/dithiane DTT, and 2-2mercaptoethanol(OME)/dithio-β (ME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of an IL-17 receptor like polypeptide, then the polypeptide will be found primarily in the supernatant after centrifugation of the cell homogenate. The polypeptide may be further isolated from the supernatant using methods such as those described herein.

The purification of an IL-17 receptor like polypeptide from solution can be accomplished using a variety of techniques. If the polypeptide has been synthesized such that it contains a tag such as Hexahistidine (IL-17 receptor like polypeptide/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag.

For example, polyhistidine binds with great affinity and specificity to nickel, thus an affinity column of nickel (such as the Qiagen® nickel columns) can be used for purification of IL-17 receptor like polypeptide/polyHis. See for example, Ausubel et al., eds., *Current Protocols in Molecular Biology*, Section 10.11.8, John Wiley & Sons, New York (1993).

Additionally, the IL-17 receptor like polypeptide may be purified through the use of a monoclonal antibody which is capable of specifically recognizing and binding to the IL-17 receptor like polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

IL-17 receptor like polypeptides, including fragments, variants and/or derivatives thereof may also be prepared by chemical synthesis methods (such as solid phase peptide synthesis) using techniques known in the art, such as those set forth by Merrifield et al., *J. Am. Chem. Soc.*, 85:2149 (1963), Houghten et al., *Proc Natl Acad. Sci. USA*, 82:5132 (1985), and Stewart and Young, Solid Phase Peptide Synthesis, Pierce Chemical Co., Rockford, Ill. (1984). Such polypeptides may be synthesized with or without a methionine on the amino terminus. Chemically synthesized IL-17 receptor like polypeptides may be oxidized using methods set forth in these references to form disulfide bridges. Chemically synthesized IL-17 receptor like polypeptides are expected to have comparable biological activity to the corresponding IL-17 receptor like polypeptides produced recombinantly or purified from natural sources, and thus may be used interchangeably with a recombinant or natural IL-17 receptor like polypeptide.

Another means of obtaining an IL-17 receptor like polypeptide is via purification from biological samples such as source tissues and/or fluids in which the IL-17 receptor like polypeptide is naturally found. Such purification can be conducted using methods for protein purification as described herein. The presence of the IL-17 receptor like polypeptide during purification may be monitored using, for example, an antibody prepared against recombinantly produced IL-17 receptor like polypeptide or peptide fragments thereof.

A number of additional methods for producing nucleic acids and polypeptides are known in the art, and the methods can be used to produce polypeptides having specificity for IL-17 receptor like. See for example, Roberts et al., *Proc. Natl. Acad. Sci. U.S.A.*, 94:12297–12303 (1997), which describes the production of fusion proteins between an mRNA and its encoded peptide. See also Roberts, R., *Curr. Opin. Chem. Biol.*, 3:268–273 (1999). Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192, 5,814,476, 5,723,323, and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 receptor like protein expression libraries, which can subsequently be used for high throughput phenotypic screening in a variety of assays, such as biochemical assays, cellular assays, and whole organism assays (e.g., plant, mouse, etc.).

Chemical Derivatives

Chemically modified derivatives of the IL-17 receptor like polypeptides may be prepared by one skilled in the art, given the disclosures set forth hereinbelow. IL-17 receptor like polypeptide derivatives are modified in a manner that is different, either in the type or location of the molecules naturally attached to the polypeptide. Derivatives may include molecules formed by the deletion of one or more naturally-attached chemical groups. The polypeptide comprising the amino acid sequence of any of SEQ ID NO:2, SEQ ID NO:5, or SEQ ID NO:7, including combinations thereof, or an IL-17 receptor like polypeptide variant may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer preferably is between about 5 kDa and about 50 kDa, more preferably between about 12 kDa and about 40 kDa and most preferably between about 20 kDa and about 35 kDa.

Suitable water soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$–$C_{10}$) alkoxy- or aryloxy-polyethylene glycol), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of any of SEQ ID NO:2, SEQ ID NO:5, or SEQ ID NO:7, including combinations thereof, or an IL-17 receptor like polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of any of SEQ ID NO:2, SEQ ID NO:5, or SEQ ID NO:7, including combinations thereof, or an IL-17 receptor like polypeptide variant becomes attached to one or more polymer molecules, and (b) obtaining the reaction product(s). The optimal reaction conditions will be determined based on known parameters and the desired result. For example, the larger the ratio of polymer molecules: protein, the greater the percentage of attached polymer molecule. In one embodiment, the IL-17 receptor like polypeptide derivative may have a single polymer molecule moiety at the amino terminus. See, for example, U.S. Pat. No. 5,234,784.

The pegylation of the polypeptide specifically may be carried out by any of the pegylation reactions known in the art, as described for example in the following references: Francis et al., *Focus on Growth Factors*, 3:4–10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$–$C_{10}$ alkoxy or aryloxy derivatives thereof (see U.S. Pat. No. 5,252,714).

In another embodiment, IL-17 receptor like polypeptides may be chemically coupled to biotin, and the biotin/IL-17 receptor like polypeptide molecules which are conjugated are then allowed to bind to avidin, resulting in tetravalent avidin/biotin/IL-17 receptor like polypeptide molecules. IL-17 receptor like polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present IL-17 receptor like polypeptide derivatives include those described herein for IL-17 receptor like polypeptides. However, the IL-17 receptor like polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents, rabbits, goats, or sheep, or other farm animals, in which the gene (or genes) encoding the native IL-17 receptor like polypeptide has (have) been disrupted ("knocked out") such that the level of expression of this gene or genes is (are) significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which either the native form of the IL-17 receptor like gene(s) for that animal or a heterologous IL-17 receptor like gene(s) is (are) over-expressed by the animal, thereby creating a "transgenic" animal. Such transgenic animals may be prepared using well known methods such as those described in U.S. Pat. No. 5,489,743 and PCT application No. WO94/28122.

The present invention further includes non-human animals in which the promoter for one or more of the IL-17 receptor like polypeptides of the present invention is either activated or inactivated (e.g., by using homologous recombination methods) to alter the level of expression of one or more of the native IL-17 receptor like polypeptides.

These non-human animals may be used for drug candidate screening. In such screening, the impact of a drug candidate on the animal may be measured. For example, drug candidates may decrease or increase the expression of the IL-17 receptor like gene. In certain embodiments, the amount of IL-17 receptor like polypeptide, that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the IL-17 receptor like molecules of the invention, including, but not limited to: the identification and validation of IL-17 receptor like disease-related genes as targets for therapeutics; molecular toxicology of IL-17 receptor like molecules and inhibitors thereof; stratification of populations and generation of surrogate markers for clinical trials; and enhancing IL-17 receptor like-related small molecule drug discovery by aiding in the identification of selective compounds in high throughput screens (HTS).

Selective Binding Agents

As used herein, the term "selective binding agent" refers to a molecule which has specificity for one or more IL-17 receptor like polypeptides. Suitable selective binding agents include, but are not limited to, antibodies and derivatives thereof, polypeptides, and small molecules. Suitable selective binding agents may be prepared using methods known in the art. An exemplary IL-17 receptor like polypeptide selective binding agent of the present invention is capable of binding a certain portion of the IL-17 receptor like polypeptide thereby inhibiting the binding of a ligand such as IL17E of SEQ ID NO: 23 to the IL-17 receptor like polypeptide receptor(s).

Selective binding agents such as antibodies and antibody fragments that bind IL-17 receptor like polypeptides are within the scope of the present invention. The antibodies may be polyclonal including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the IL-17 receptor like polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an IL-17 receptor like polypeptide generally are produced in animals (e.g., rabbits or mice) by means of multiple subcutaneous or intraperitoneal injections of IL-17 receptor like polypeptide and an adjuvant. It may be useful to conjugate an IL-17 receptor like polypeptide to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-IL-17 receptor like polypeptide antibody titer.

Monoclonal antibodies directed toward an IL-17 receptor like polypeptide are produced using any method which provides for the production of antibody molecules by continuous cell lines in culture. Examples of suitable methods for preparing monoclonal antibodies include the hybridoma methods of Kohler et al., *Nature,* 256:495–497 (1975) and the human B-cell hybridoma method, Kozbor, *J. Immunol.,* 133:3001 (1984); Brodeur et al., *Monoclonal Antibody Production Techniques and Applications,* pp. 51–63 (Marcel Dekker, Inc., New York, 1987). Also provided by the invention are hybridoma cell lines which produce monoclonal antibodies reactive with IL-17 receptor like polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is identical with or homologous to a corresponding sequence in antibodies derived from another species or belonging to another antibody class or subclass. Also included are fragments of such antibodies, so long as they exhibit the desired biological activity. See, U.S. Pat. No. 4,816,567; Morrison et al., *Proc. Natl. Acad. Sci.,* 81:6851–6855 (1985).

In another embodiment, a monoclonal antibody of the invention is a "humanized" antibody. Methods for humanizing non-human antibodies are well known in the art. See U.S. Pat. Nos. 5,585,089, and 5,693,762. Generally, a humanized antibody has one or more amino acid residues introduced into it from a source which is non-human. Humanization can be performed, for example, using methods described in the art. (See U.S. Pat. Nos. 5,585,089 and 5,693,762). Generally, a humanized antibody has one or more amino acid residues introduced into it form a source which is non-human. Humanization can be preformed, for example, using methods known in the art(Jones et al., *Nature* 321:522–525 (1986); Riechmann et al., *Nature,* 332:323–327 (1988); Verhoeyen et al., *Science* 239:1534–1536 (1988)), by substituting at least a portion of a rodent complementarity-determining regions (CDRs) for the corresponding regions of a human antibody.

Also encompassed by the invention are human antibodies which bind IL-17 receptor like polypeptides. Using transgenic animals (e.g., mice) that are capable of producing a repertoire of human antibodies in the absence of endogenous immunoglobulin production such antibodies are produced by immunization with an IL-17 receptor like antigen (i.e., having at least 6 contiguous amino acids), optionally conjugated to a carrier. See, for example, Jakobovits et al., *Proc. Natl. Acad. Sci.,* 90:2551–2555 (1993); Jakobovits et al., *Nature* 362:255–258 (1993); Bruggermann et al., *Year in Immuno.,* 7:33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human variable regions including human (rather than e.g., murine) amino acid sequences, including variable regions, including human which are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced from phage-display libraries (Hoogenboom et al., *J. Mol. Biol.* 227:381 (1991); Marks et al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application no. PCT/US98/ 17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-IL-17 receptor like antibodies of the invention may be employed in any known assay method, such as competitive binding assays, direct and indirect sandwich assays, and immunoprecipitation assays (Sola, Monoclonal Antibodies: A Manual of Techniques, pp. 147–158 (CRC Press, Inc., 1987)) for the detection and quantitation of IL-17 receptor like polypeptides. The antibodies will bind IL-17 receptor like polypeptides with an affinity which is appropriate for the assay method being employed.

For diagnostic applications, in certain embodiments, anti-IL-17 receptor like antibodies may be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, β-galactosidase, or horseradish peroxidase (Bayer et al., *Meth. Enz.*, 184:138–163 (1990)).

Competitive binding assays rely on the ability of a labeled standard (e.g., an IL-17 receptor like polypeptide, or an immunologically reactive portion thereof) to compete with the test sample analyte (an IL-17 receptor like polypeptide) for binding with a limited amount of anti IL-17 receptor like antibody. The amount of an IL-17 receptor like polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-IL-17 receptor like antibodies, also are useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

The invention also relates to a kit comprising IL-17 receptor like selective binding agents (such as antibodies) and other reagents useful for detecting IL-17 receptor like polypeptide levels in biological samples. Such reagents may include a secondary activity, a detectable label, blocking serum, positive and negative control samples, and detection reagents Selective binding agents of the invention, including antibodies, may be used as therapeutics. These therapeutic agents are generally agonists or antagonists, in that they either enhance or reduce, respectively, at least one of the biological activities of an IL-17 receptor like polypeptide. In one embodiment, antagonist antibodies of the invention are antibodies or binding fragments thereof which are capable of specifically binding to an IL-17 receptor like polypeptide and which are capable of inhibiting or eliminating the functional activity of an IL-17 receptor like polypeptide in vivo or in vitro. In preferred embodiments, the selective binding agent, e.g., an antagonist antibody, will inhibit the functional activity of an IL-17 receptor like polypeptide by at least about 50%, and preferably by at least about 80%. In another embodiment, the selective binding agent may be an anti-IL-17 receptor like polypeptide antibody that is capable of interacting with an IL-17 receptor like binding partner (a ligand or receptor) thereby inhibiting or eliminating IL-17 receptor like activity in vitro or in vivo. Selective binding agents, including agonist and antagonist anti-IL-17 receptor like antibodies, are identified by screening assays which are well known in the art.

The invention also relates to a kit comprising IL-17 receptor like selective binding agents (such as antibodies) and other reagents useful for detecting IL-17 receptor like polypeptide levels in biological samples. Such reagents may include, a detectable label, blocking serum, positive and negative control samples, and detection reagents.

IL-17 receptor like polypeptides can be used to clone IL-17 receptor like ligand(s) using an "expression cloning" strategy. Radiolabeled ($^{125}$-Iodine) IL-17 receptor like polypeptide or "affinity/activity-tagged" IL-17 receptor like polypeptide (such as an Fc fusion or an alkaline phosphatase fusion) can be used in binding assays to identify a cell type or cell line or tissue that expresses IL-17 receptor like ligand(s). RNA isolated from such cells or tissues can then be converted to cDNA, cloned into a mammalian expression vector, and transfected into mammalian cells (for example, COS, or 293) to create an expression library. Radiolabeled or tagged IL-17 receptor like polypeptide can then be used as an affinity reagent to identify and isolate the subset of cells in this library expressing IL-17 receptor like ligand(s). DNA is then isolated from these cells and transfected into mammalian cells to create a secondary expression library in which the fraction of cells expressing IL-17 receptor like ligand(s) would be many-fold higher than in the original library. This enrichment process can be repeated iteratively until a single recombinant clone containing an IL-17 receptor like ligand is isolated. Isolation of IL-17 receptor like ligand(s) is useful for identifying or developing novel agonists and antagonists of the IL-17 receptor like signaling pathway. Such agonists and antagonists include IL-17 receptor like ligand(s), anti-IL-17 receptor like ligand antibodies, small molecules, or antisense oligonucleotides.

Assaying for Other Modulators of Il-17 Receptor Like Polypeptide Activity

In some situations, it may be desirable to identify molecules that are modulators, i.e., agonists or antagonists, of the activity of IL-17 receptor like polypeptide. Natural or synthetic molecules that modulate IL-17 receptor like polypeptide may be identified using one or more screening assays, such as those described herein. Such molecules may be administered either in an ex vivo manner, or in an in vivo manner by injection, or by oral delivery, implantation device, or the like.

"Test molecule(s)" refers to the molecule(s) that is/are under evaluation for the ability to modulate (i.e., increase or decrease) the activity of an IL-17 receptor like polypeptide. Most commonly, a test molecule will interact directly with an IL-17 receptor like polypeptide. However, it is also contemplated that a test molecule may also modulate IL-17 receptor like polypeptide activity indirectly, such as by affecting IL-17 receptor like gene expression, or by binding to an IL-17 receptor like binding partner (e.g., receptor or ligand). In one embodiment, a test molecule will bind to an IL-17 receptor like polypeptide with an affinity constant of at least about $10^{-6}$ M, preferably about $10^{-8}$ M, more preferably about $10^{-9}$ M, and even more preferably about $10^{-10}$ M.

Methods for identifying compounds which interact with IL-17 receptor like polypeptides are encompassed by the present invention. In certain embodiments, an IL-17 receptor like polypeptide is incubated with a test molecule under conditions which permit the interaction of the test molecule with an IL-17 receptor like polypeptide, and the extent of the interaction can be measured. The test molecule(s) can be screened in a substantially purified form or in a crude mixture. The test molecules can be nucleic acid molecules, proteins, peptides, carbohydrates, lipids, organic and inorganic compounds.

In certain embodiments, an IL-17 receptor like polypeptide agonist or antagonist may be a protein, peptide, carbohydrate, lipid, or small molecular weight molecule which interacts with IL-17 receptor like polypeptide, or ligand thereof, to regulate its activity. Molecules which regulate IL-17 receptor like polypeptide expression include nucleic acids which are complementary to nucleic acids encoding an IL-17 receptor like polypeptide, or are complementary to nucleic acids sequences which direct or control the expression of IL-17 receptor like polypeptide, and which act as anti-sense regulators of expression.

Once a set of test molecules has been identified as interacting with an IL-17 receptor like polypeptide, the molecules may be further evaluated for their ability to increase or decrease IL-17 receptor like polypeptide activity. The measurement of the interaction of test molecules with IL-17 receptor like polypeptides may be carried out in several formats, including cell-based binding assays, membrane binding assays, solution-phase assays and immunoassays. In general, test molecules are incubated with an IL-17 receptor like polypeptide for a specified period of time, and IL-17 receptor like polypeptide activity is determined by one or more assays for measuring biological activity.

The interaction of test molecules with IL-17 receptor like polypeptides may also be assayed directly using polyclonal or monoclonal antibodies in an immunoassay. Alternatively, modified forms of IL-17 receptor like polypeptides containing epitope tags as described herein may be used in immunoassays.

In certain embodiments, a IL-17 receptor like polypeptide agonist or antagonist may be a protein, peptide, carbohydrate, lipid, or small molecular weight molecule which interacts with IL-17 receptor like polypeptide to regulate its activity. Potential protein antagonists of IL-17 receptor like polypeptide include antibodies which interact with active regions of the polypeptide and inhibit or eliminate at least one activity of IL-17 receptor like molecules. Molecules which regulate IL-17 receptor like polypeptide expression include nucleic acids which are complementary to nucleic acids encoding a IL-17 receptor like polypeptide, or are complementary to nucleic acids sequences which direct or control the expression of IL-17 receptor like polypeptide, and which act as anti-sense regulators of expression.

In the event that IL-17 receptor like polypeptides display biological activity through an interaction with a binding partner (e.g., a receptor or a ligand), a variety of in vitro assays may be used to measure the binding of an IL-17 receptor like polypeptide to the corresponding binding partner (such as a selective binding agent, receptor, or ligand). These assays may be used to screen test molecules for their ability to increase or decrease the rate and/or the extent of binding of an IL-17 receptor like polypeptide to its binding partner. In one assay, an IL-17 receptor like polypeptide is immobilized in the wells of a microtiter plate. Radiolabeled IL-17 receptor like binding partner (for example, iodinated IL-17 receptor like binding partner) and the test molecule(s) can then be added either one at a time (in either order) or simultaneously to the wells. After incubation, the wells can be washed and counted, using a scintillation counter, for radioactivity to determine the extent to which the binding partner bound to IL-17 receptor like polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing IL-17 receptor like binding partner to the microtiter plate wells, incubating with the test molecule and radiolabeled IL-17 receptor like polypeptide, and determining the extent of IL-17 receptor like polypeptide binding. See, for example, chapter 18, *Current Protocols in Molecular Biology*, Ausubel et al., eds., John Wiley & Sons, New York, N.Y. (1995).

As an alternative to radiolabelling, an IL-17 receptor like polypeptide or its binding partner may be conjugated to biotin and the presence of biotinylated protein can then be detected using streptavidin linked to an enzyme, such as horseradish peroxidase (HRP) or alkaline phosphatase (AP), that can be detected colorometrically, or by fluorescent tagging of streptavidin. An antibody directed to an IL-17 receptor like polypeptide or to an IL-17 receptor like binding partner and conjugated to biotin may also be used and can be detected after incubation with enzyme-linked streptavidin linked to AP or HRP.

An IL-17 receptor like polypeptide or an IL-17 receptor like binding partner can also be immobilized by attachment to agarose beads, acrylic beads or other types of such inert solid phase substrates. The substrate-protein complex can be placed in a solution containing the complementary protein and the test compound. After incubation, the beads can be precipitated by centrifugation, and the amount of binding between an IL-17 receptor like polypeptide and its binding partner can be assessed using the methods described herein. Alternatively, the substrate-protein complex can be immobilized in a column, and the test molecule and complementary protein are passed through the column. The formation of a complex between an IL-17 receptor like polypeptide and its binding partner can then be assessed using any of the techniques set forth herein, i.e., radiolabelling, antibody binding, or the like.

Another in vitro assay that is useful for identifying a test molecule which increases or decreases the formation of a complex between an IL-17 receptor like binding protein and an IL-17 receptor like binding partner is a surface plasmon resonance detector system such as the BIAcore assay system (Pharmacia, Piscataway, N.J.). The BIAcore system may be carried out using the manufacturer's protocol. This assay essentially involves the covalent binding of either IL-17 receptor like polypeptide or an IL-17 receptor like binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between an IL-17 receptor like polypeptide and an IL-17 receptor like binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for effects on complex formation by IL-17 receptor like polypeptide and IL-17 receptor like binding partner. The assays may be automated to screen compounds generated in phage display, synthetic peptide, and chemical synthesis libraries.

Compounds which increase or decrease the formation of a complex between an IL-17 receptor like polypeptide and an IL-17 receptor like binding partner may also be screened in cell culture using cells and cell lines expressing either IL-17 receptor like polypeptide or IL-17 receptor like binding partner. Cells and cell lines may be obtained from any mammal, but preferably will be from human or other primate, canine, or rodent sources. The binding of an IL-17 receptor like polypeptide to cells expressing IL-17 receptor like binding partner at the surface is evaluated in the presence or absence of test molecules, and the extent of binding may be determined by, for example, flow cytometry using a biotinylated antibody to an IL-17 receptor like binding partner. Cell culture assays can be used advantageously to further evaluate compounds that score positive in protein binding assays described herein.

Cell cultures can also be used to screen the impact of a drug candidate. For example, drug candidates may decrease or increase the expression of the IL-17 receptor like gene. In certain embodiments, the amount of IL-17 receptor like polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

A yeast two-hybrid system (Chien et al., *Proc. Natl. Acad. Sci. USA*, 88:9578–9583, 1991) can be used to identify novel polypeptides that bind to, or interact with, IL-17 receptor like polypeptides. As an example, a yeast-two hybrid bait construct can be generated in a vector (such as the pAS2-1 from Clontech) which encodes a yeast GAL4-DNA binding domain fused to the Cdkll polynucleotide. This bait construct may be used to screen human cDNA libraries wherein the cDNA library sequences are fused to GAL4 activation domains. Positive interactions will result in the activation of a reporter gene such as β-Gal. Positive clones emerging from the screening may be characterized further to identify interacting proteins.

Internalizing Proteins

The tat protein sequence (from HIV) can be used to internalize proteins into a cell. See e.g., Falwell et al., *Proc. Natl. Acad. Sci.*, 91:664–668 (1994). For example, an 11 amino acid sequence (YGRKKRRQRRR SEQ ID NO: 18) of the HIV tat protein (termed the "protein transduction domain", or TAT PDT) has been described as mediating delivery across the cytoplasmic membrane and the nuclear membrane of a cell. See Schwarze et al., *Science*, 285: 1569–1572 (1999); and Nagahara et al., *Nature Medicine*, 4:1449–1452 (1998). In these procedures, FITC-constructs (FITC-GGGGYGRKKRRQRRR SEQ ID NO: 19) are prepared which bind to cells as observed by fluorescence-activated cell sorting (FACS) analysis, and these constructs penetrate tissues after i.p. adminstration. Next, tat-bgal fusion proteins are constructed. Cells treated with this construct demonstrated β-gal activity. Following injection, a number of tissues, including liver, kidney, lung, heart, and brain tissue have been found to demonstrate expression using these procedures. It is believed that these constructions underwent some degree of unfolding in order to enter the cell; as such, refolding may be required after entering the cell.

It will thus be appreciated that the tat protein sequence may be used to internalize a desired protein or polypeptide into a cell. For example, using the tat protein sequence, an IL-17 receptor like antagonist (such as an anti-IL-17 receptor like selective binding agent, small molecule, soluble receptor, or antisense oligonucleotide) can be administered intracellularly to inhibit the activity of an IL-17 receptor like molecule. As used herein, the term "IL-17 receptor like molecule" refers to both IL-17 receptor like nucleic acid molecules and IL-17 receptor like polypeptides as defined herein. Where desired, the IL-17 receptor like protein itself may also be internally administered to a cell using these procedures. See also, Strauss, E., "Introducing Proteins Into the Body's Cells", *Science*, 285:1466–1467 (1999).

Cell Source Identification Using IL-17 Receptor Like Polypeptides

In accordance with certain embodiments of the invention, it may be useful to be able to determine the source of a certain cell type associated with an IL-17 receptor like polypeptide. For example, it may be useful to determine the origin of a disease or pathological condition as an aid in selecting an appropriate therapy.

Therapeutic Uses

A non-exclusive list of acute and chronic diseases which can be treated, diagnosed, ameliorated, or prevented with the IL-17 receptor like nucleic acids, polypeptides, and agonists and antagonists of the invention include:

The diagnosis and/or treatment of diseases involving immune system dysfunction. Examples of such diseases include, but are not limited to, rheumatoid arthritis, psioriatic arthritis, inflammatory arthritis, osteoarthritis, inflammatory joint disease, autoimmune disease including autoimmune vasculitis, multiple sclerosis, lupus, diabetes (e.g., insulin diabetes), inflammatory bowel disease, transplant rejection, graft vs. host disease, and inflammatory conditions resulting from strain, sprain, cartilage damage, trauma, orthopedic surgery, infection or other disease processes. Other diseases influenced by the dysfunction of the immune system are encompassed within the scope of the invention, including but not limited to, allergies. The IL-17 receptor like nucleic acids, polypeptides, and agonists iand antagonists of the invention can also be used to inhibit T cell proliferation, to inhibit T cell activation, and/or to inhibit B cell proliferation and/or immunoglobulin secretion.

The diagnosis and/or treatment of diseases involving infection. Examples of such diseases include, but are not limited to, leprosy, viral infections such as hepatitis or HIV, bacterial infection such as *clostridium* associated illnesses, including *clostridium*-associated diarrhea, pulmonary tuberculosis, acute febrile illness from bacteria such as or virus, fever, acute phase response of the liver, septicemia, septic shock. Other diseases involving infection are encompassed within the scope of the invention.

The diagnosis and/or treatment of diseases involving weight disorders. Examples of such diseases include, but are not limited to obesity, anorexia, cachexia, including AIDS-induced cachexia, myopathies (e.g., muscle protein metabolism, such as in sepsis), and hypoglycemia. Other diseases involving weight disorders are encompassed within the scope of the invention.

The diagnosis and/or treatment of diseases involving neuronal dysfunction. Examples of such diseases include, but are not limited to Alzheimer's, Parkinson's disease, neurotoxicity (e.g., as induced by HIV), ALS, brain injury, stress, depression, nociception and other pain (including cancer-related pain), hyperalgesia, epilepsy, learning impairment and memory disorders, sleep disturbance, and peripheral and central neuropathies. Other neurological disorders are encompassed within the scope of the invention.

The diagnosis and/or treatment of diseases involving the lung. Examples of such diseases include, but are not limited to, acute or chronic lung injury including interstitial lung disease, acute respiratory disease syndrome, pulmonary hypertension, emphysema, cystic fibrosis, pulmonary fibrosis, and asthma. Other diseases of the lung are encompassed within the scope of the invention.

The diagnosis and/or treatment of diseases involving the skin. Examples of such diseases include, but are not limited to, psoriasis, eczema, and wound healing. Other diseases of the skin are encompassed within the scope of the Invention.

The diagnosis and/or treatment of diseases involving the kidney. Examples of such diseases include, but are not limited to, acute and chronic glomerulonephritis. Other diseases of the kidney are encompassed within the scope of the invention.

The diagnosis and/or treatment of diseases involving the bone. Examples of such diseases include, but are not limited to, osteoporosis, osteopetrosis, osteogenesis imperfecta, Paget's disease, periodontal disease, temporal mandibular joint disease, and hypercalcemia. Other diseases of the bone are encompassed within the scope of the invention.

The diagnosis and/or treatment of diseases involving the vascular system. Examples of such diseases include, but are not limited to hemorrhage or stroke, hemorrhagic shock, ischemia, including cardiac ischemia and cerebral ischemia (e.g., brain injury as a result of trauma, epilepsy, hemorrhage or stroke, each of which may lead to neurodegeneration), atherosclerosis, congestive heart failure; restenosis, reperfusion injury, and angiogenesis. Other diseases of the vascular system are encompassed within the scope of the invention.

The diagnosis and/or treatment of tumor cells. Examples of such diseases include, but are not limited to, lymphomas, bone sarcoma, chronic and acute myelogenous leukemia (AML and CML), myelomoncytic leukemias and other leukemias, multiple myeloma, lung, breast cancer, tumor metastasis, and side effects from radiation therapy. Other diseases involving tumor cells are encompassed within the scope of the invention.

The diagnosis and/or treatment of reproductive disorders. Examples of such diseases include, but are not limited to, infertility, miscarriage, pre-term labor and delivery, and endometriosis. Other diseases involving the reproductive system are encompassed within the scope of the invention.

The diagnosis and/or treatment of eye disorders. Examples of such diseases include, but are not limited to, inflammatory eye disease, as may be associated with, for example, corneal transplant; retinal degeneration, blindness, macular degeneration, glaucoma, uveitis, and retinal neuropathy. Other diseases of the eye are encompassed within the scope of the invention.

The diagnosis and/or treatment of diseases involving inflammation. Examples of such diseases include but are not limited to those described herein.

Other diseases which are treatable using agents within the scope of the invention include acute pancreatitis, chronic fatigue syndrome, fibromyalgia, and Kawasaki's disease (MLNS).

Other diseases associated with undesirable levels of one or more of IL-1, IL-1ra, the ligand of the present IL-17 receptor like polypeptide, and/or the present IL-17 receptor like polypeptide itself are encompassed within the scope of the invention. Undesirable levels include excessive and/or sub-normal levels of IL-1, IL-1ra, the ligand of the present IL-17 receptor like polypeptide, and/or the IL-17 receptor like polypeptides described herein.

As contemplated by the present invention, an agonist or antagonist of the IL-17 receptor like polypeptide (including, but not limited to, anti-IL-17 receptor like selective binding agents (such as antibodies), ligands to the IL-17 receptor like receptor, soluble IL-17 receptor like polypeptides, small molecules, and antisense oligonucleotides, or an IL-17 receptor like polypeptide itself) may be administered as an adjunct to other therapy and also with other pharmaceutical compositions suitable for the indication being treated. An agonist or antagonist of the IL-17 receptor like polypeptide, and/or an IL-17 receptor like polypeptide itself and any of one or more additional therapies or pharmaceutical formulations may be administered separately, sequentially, or simultaneously.

In a specific embodiment, the present invention is directed to the use of an agonist or antagonist of the IL-17 receptor like polypeptide, and/or an IL-17 receptor like polypeptide itself in combination (pre-treatment, post-treatment, or concurrent treatment) with any of one or more IL-1 inhibitors for the treatment or prevention of the diseases and disorders recited herein.

IL-1 inhibitors include any protein capable of specifically preventing activation of cellular receptors to IL-1, which may result from any number of mechanisms. Such mechanisms include downregulating IL-1 production, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Classes of interleukin-1 inhibitors include:

Interleukin-1 receptor antagonists such as IL-1ra, as described herein;
Anti-IL-1 receptor monoclonal antibodies (e.g., EP 623674);
IL-1 binding proteins such as soluble IL-1 receptors (e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812;
Anti-IL-1 monoclonal antibodies (e.g., WO 9501997, WO 9402627, WO 9006371, U.S. Pat. No. 4,935,343, EP 364778, EP 267611 and EP 220063;
IL-1 receptor accessory proteins and antibodies thereto (e.g., WO 96/23067);
Inhibitors of interleukin-1β converting enzyme (ICE) or caspase I, which can be used to inhibit IL-1 beta production and secretion;
Interleukin-2β protease inhibitors;
Other compounds and proteins which block in vivo synthesis or extracellular release of IL-1.

Exemplary IL-1 inhibitors are disclosed in the following references:
U.S. Pat. Nos. 5,747,444; 5,359,032; 5608035; 5843905; 5359032; 5866576; 5869660; 5869315; 5872095; 5955480;
International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, and 99/36415;
European (EP) patent applications 534978 and 894795; and French patent application FR 2762514;

Interleukin-1 receptor antagonist (IL-1ra) is a human protein that acts as a natural inhibitor of interleukin-1. Preferred receptor antagonists (including IL-1ra and variants and derivatives thereof), as well as methods of making and using thereof, are described in U.S. Pat. No. 5,075,222; WO 91/08285; WO 91/17184; AU 9173636; WO 92/16221; WO93/21946; WO 94/06457; WO 94/21275; FR 2706772; WO 94/21235; DE 4219626, WO 94/20517; WO 96/22793; WO 97/28828; and WO 99/36541. The proteins include glycosylated as well as non-glycosylated IL-1 receptor antagonists.

Those skilled in the art will recognize that many combinations of deletions, insertions, and substitutions (individually or collectively "variant(s)" herein) can be made within the amino acid sequences of IL-1ra, provided that the resulting molecule is biologically active (e.g., possesses the ability to affect one or more of the diseases and disorders such as those recited herein.)

In a specific embodiment, the present invention is directed to the use of an agonist or antagonist of the IL-17 receptor like polypeptide, and/or an IL-17 receptor like polypeptide itself in combination (pre-treatment, post-treatment, or concurrent treatment) with any of one or more TNF inhibitors for the treatment or prevention of the diseases and disorders recited herein.

Such TNF inhibitors include compounds and proteins which block in vivo synthesis or extracellular release of TNF. In a specific embodiment, the present invention is directed to the use of an agonist or antagonist of the IL-17 receptor like polypeptide, and/or an IL-17 receptor like polypeptide itself in combination (pre-treatment, post-treatment, or concurrent treatment) with any of one or more of the following TNF inhibitors: TNF binding proteins (soluble TNF receptor type-I and soluble TNF receptor type-II ("sTNFRs"), as defined herein), anti-TNF antibodies, granulocyte colony stimulating factor; thalidomide; BN 50730; tenidap; E 5531; tiapafant PCA 4248; nimesulide; panavir; rolipram; RP 73401; peptide T; MDL 201,449A; (1R,3S)-Cis-1-[9-(2,6-diaminopurinyl)]-3-hydroxy-4-cyclopentene hydrochloride; (1R,3R)-trans-1-(9-(2,6-diamino)purine]-3-acetoxycyclopentane; (1R,3R)-trans-1-[9-adenyl)-3-azidocyclopentane hydrochloride and (1R,3R)-trans-1-(6-hydroxy-purin-9-yl)-3-azidocyclo-pentane. TNF binding proteins are disclosed in the art (EP 308 378, EP 422 339, GB 2 218 101, EP 393 438, WO 90/13575, EP 398 327, EP 412 486, WO 91/03553, EP 418 014, JP 127,800/1991, EP 433 900, U.S. Pat. No. 5,136,021, GB 2 246 569, EP 464 533, WO 92/01002, WO 92/13095, WO 92/16221, EP 512 528, EP 526 905, WO 93/07863, EP 568 928, WO 93/21946, WO 93/19777, EP 417 563, WO 94/06476, and PCT International Application No. PCT/US97/12244).

For example, EP 393 438 and EP 422 339 teach the amino acid and nucleic acid sequences of a soluble TNF receptor type I (also known as "IsTNFR-I" or "30 kDa TNF inhibitor") and a soluble TNF receptor type II (also known as "sTNFR-II" or "40 kDa TNF inhibitor"), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types and expressing the gene to produce the inhibitors. Additionally, polyvalent forms (i.e., molecules comprising more than one active moiety) of sTNFR-I and sTNFR-II have also been disclosed. In one embodiment, the polyvalent form may be constructed by chemically coupling at least one TNF inhibitor and another moiety with any clinically acceptable linker, for example polyethylene glycol (WO 92/16221 and WO 95/34326), by a peptide linker (Neve et al. (1996), *Cytokine,* 8(5):365–370, by chemically coupling to biotin and then binding to avidin (WO 91/03553) and, finally, by combining chimeric antibody molecules (U.S. Pat. No. 5,116,964, WO 89/09622, WO 91/16437 and EP 315062.

Anti-TNF antibodies include MAK 195F Fab antibody (Holler et al. (1993), 1*st International Symposium on Cytokines in Bone Marrow Transplantation,* 147); CDP 571 anti-TNF monoclonal antibody (Rankin et al. (1995), *British Journal of Rheumatology,* 34:334–342); BAY X$^{135}$I murine anti-tumor necrosis factor monoclonal antibody (Kieft et al. (1995), 7th European Congress of Clinical Microbiology and Infectious Diseases, page 9); CenTNF cA2 (REMICADE) anti-TNF monoclonal antibody (Elliott et al. (1994), *Lancet,* 344:1125–1127 and Elliott et al. (1994), *Lancet,* 344:1105–1110).

It will be appreciated that the IL-17 receptor like polypeptides may be used (simultaneously or sequentially) in combination with one or more cytokines, growth factors, antibiotics, anti-inflammatories, and/or chemotherapeutic agents as is appropriate for the indication being treated.

In one specific embodiment, the present invention is directed to the use of agonist or antagonist of the IL-17 receptor like polypeptide, and/or an IL-17 receptor like polypeptide itself in combination (pretreatment, post-treatment, or concurrent treatment) with secreted or soluble human fas antigen or recombinant versions thereof (WO 96/20206 and Mountz et al., *J. Immunology,* 155:4829–4837; and EP 510 691. WO 96/20206 discloses secreted human fas antigen (native and recombinant, including an Ig fusion protein), methods for isolating the genes responsible for coding the soluble recombinant human fas antigen, methods for cloning the gene in suitable vectors and cell types, and methods for expressing the gene to produce the inhibitors. EP 510 691 describes DNAs coding for human fas antigen, including soluble fas antigen, vectors expressing for said DNAs and transformants transfected with the vector. When administered parenterally, doses of a secreted or soluble fas antigen fusion protein each are generally from bout 1 micrograms/kg to about 100 micrograms/kg.

Treatment of the diseases and disorders recited herein, can include the use of first line drugs for control of pain and inflammation. These drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present invention is directed to the use of an agonist or antagonist of the IL-17 receptor like polypeptide, and/or an IL-17 receptor like polypeptide itself and any of one or more NSAIDs for the treatment of the diseases and disorders recited herein, including acute and chronic inflammation such as rheumatic diseases; and graft versus host disease. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine-1,1-dioxide-4-(N-phenyl)-carboxamide. Structurally related oxicams having similar analgesic and anti-inflammatory properties are also intended to be encompassed by this group.

In still another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which may be used comprise: difenamizole and epirizole. Structurally related pyrazoles having similar analgesic and anti-inflammatory properties are also intended to be encompassed by this group.

In an additional specific embodiment, the present invention is directed to the use of an agonist or antagonist of the IL-17 receptor like polypeptide, and/or an IL-17 receptor like polypeptide itself in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more of the following NSAIDs: ε-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, ELS08, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPASS10, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present invention is directed to the use of an agonist or antagonist of the IL-17 receptor like polypeptide, and/or an IL-17 receptor like polypeptide itself in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In still another specific embodiment, the present invention is directed to the use of an agonist or antagonist of the IL-17 receptor like polypeptide, and/or an IL-17 receptor like polypeptide itself in combination (pretreatment, post-treatment, or concurrent treatment) with any of one or more antimicrobials, prodrug esters or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

IL-17 Receptor Like Compositions and Administration

Therapeutic compositions are within the scope of the present invention. Such IL-17 receptor like pharmaceutical compositions may comprise a therapeutically effective amount of an IL-17 receptor like polypeptide or an IL-17 receptor like nucleic acid molecule in admixture with a pharmaceutically or physiologically acceptable formulation agent selected for suitability with the mode of administration. Other pharmaceutical compositions may comprise a therapeutically effective amount of one or more IL-17 receptor like selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine), antimicrobials, antioxidants (such as ascorbic acid, sodium sulfite or sodium hydrogen-sulfite), buffers (such as borate, bicarbonate, Tris-HCl, citrates, phosphates, other organic acids), bulking agents (such as mannitol or glycine), chelating agents (such as ethylenediamine tetraacetic acid (EDTA)), complexing agents (such as caffeine, polyvinylpyrrolidone, beta-cyclodextrin or hydroxypropyl-beta-cyclodextrin), fillers, monosaccharides, disaccharides, and other carbohydrates (such as glucose, mannose, or dextrins), proteins (such as serum albumin, gelatin or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid or hydrogen peroxide), solvents (such as glycerin, propylene glycol or polyethylene glycol), sugar alcohols (such as mannitol or sorbitol), suspending agents, surfactants or wetting agents (such as pluronics, PEG, sorbitan esters, polysorbates such as polysorbate 20, polysorbate 80, triton, tromethamine, lecithin, cholesterol, tyloxapal), stability enhancing agents (sucrose or sorbitol), tonicity enhancing agents (such as alkali metal halides (preferably sodium or potassium chloride), mannitol sorbitol), delivery vehicles, diluents, excipients and/or pharmaceutical adjuvants. See Remington's *Pharmaceutical Sciences*, 18$^{th}$ Ed., A. R. Gennaro, ed., Mack Publishing Company (1990).

The optimal pharmaceutical formulation will be determined by one skilled in the art depending upon, for example, the intended route of administration, delivery format, and desired dosage. See for example, *Remington's Pharmaceutical Sciences, supra*. Such compositions may influence the physical state, stability, rate of in vivo release, and rate of in vivo clearance of the IL-17 receptor like molecule.

The primary vehicle or carrier in a pharmaceutical composition may be either aqueous or non-aqueous in nature. For example, a suitable vehicle or carrier may be water for injection, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0–8.5, or acetate buffer of about pH 4.0–5.5, which may further include sorbitol or a suitable substitute therefor. In one embodiment of the present invention, IL-17 receptor like polypeptide compositions may be prepared for storage by mixing the selected composition having the desired degree of purity with optional formulation agents (*Remington's Pharmaceutical Sciences, supra*) in the form of a lyophilized cake or an aqueous solution. Further, the IL-17 receptor like polypeptide product may be formulated as a lyophilizate using appropriate excipients such as sucrose.

The IL-17 receptor like pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired IL-17 receptor like molecule in a pharmaceutically acceptable vehicle. A particularly suitable vehicle for parenteral injection is sterile distilled water in which a IL-17 receptor like molecule is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), or beads, or liposomes, that provides for the controlled or sustained release of the product which may then be delivered as a depot injection. Hyaluronic acid may also be used, and this may have the effect of promoting sustained duration in the circulation. Other suitable means for the introduction of the desired molecule include implantable drug delivery devices.

Pharmaceutical compositions such as (1) slow-release formulations, (2) inhalant mists, or (3) orally active formulations are also envisioned. The IL-17 receptor like molecule pharmaceutical composition generally is formulated for parenteral administration. Such parenterally administered therapeutic compositions are typically in the form of a pyrogen-free, parenterally acceptable aqueous solution comprising the desired IL-17 receptor like molecule in a pharmaceutically acceptable vehicle. The IL-17 receptor like molecule pharmaceutical compositions also may include particulate preparations of polymeric compounds such as polylactic acid, polyglycolic acid, etc. or the introduction of the molecule into liposomes. Hyaluronic acid may also be used, and this may have the effect of promoting sustained duration in the circulation In one embodiment, a pharmaceutical composition may be formulated for inhalation. For example, an IL-17 receptor like polypeptide may be formulated as a dry powder for inhalation. IL-17 receptor like polypeptide or IL-17 receptor like nucleic acid molecule inhalation solutions may also be formulated with a liquefied propellant for aerosol delivery. In yet another embodiment, solutions may be nebulized. Pulmonary administration is further described in PCT application no. PCT/US94/001875, which describes pulmonary delivery of chemically modified proteins.

It is also contemplated that certain formulations may be administered orally. In one embodiment of the present invention, IL-17 receptor like polypeptides which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the IL-17 receptor like molecule. Diluents, flavorings, low melting point waxes, vegetable oils, lubricants, suspending agents, tablet disintegrating agents, and binders may also be employed.

Another pharmaceutical composition may involve an effective quantity of IL-17 receptor like polypeptides in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional IL-17 receptor like pharmaceutical formulations will be evident to those skilled in the art, including formulations involving IL-17 receptor like polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 which describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., *Biopolymers*, 22:547–556 (1983)), poly (2-hydroxyethyl-methacrylate) (Langer et al., *J. Biomed. Mater. Res.*, 15:167–277 (1981) and Langer, *Chem. Tech.*, 12:98–105 (1982)), ethylene vinyl acetate (Langer et al., supra) or poly-D(−)-3-hydroxybutyric acid (EP 133,988). Sustained-release compositions also may include liposomes, which can be prepared by any of several methods known in the art. See e.g., Eppstein et al., *Proc. Natl. Acad. Sci. USA*, 82:3688–3692 (1985); EP 36,676; EP 88,046; EP 143,949.

The IL-17 receptor like pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of an IL-17 receptor like pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the IL-17 receptor like molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the IL-17 receptor like molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. oral, inhalation, injection or infusion by intravenous, intraperitoneal, intracerebral (intra-parenchymal), intracerebroventricular, intramuscular, intraocular, intraarterial, intraportal, or intralesional routes, or by sustained release systems or implantation device. Where desired, the compositions may be administered by continuosly by infusion, by bolus injection or continuously by infusion, or by implantation device.

Alternatively or additionally, the composition may be administered locally via implantation into the affected area of a membrane, sponge, or other appropriate material on to which the desired molecule has been absorbed or encapsulated. Where an implantation device is used, the device may be directly through the device implanted into any suitable tissue or organ, and delivery of the desired molecule may be via diffusion, time release bolus, or continuous administration, or via catheter continuous infusion.

It will further be appreciated that the IL-17 receptor like polypeptides, including fragments, variants, and derivatives, may be employed alone, together, or in combination with other polypeptides and pharmaceutical compositions. For example, the IL-17 receptor like polypeptides may be used in combination with cytokines, growth factors, antibiotics, anti-inflammatories, and/or chemotherapeutic agents as is appropriate for the indication being treated.

In some cases, it may be desirable to use IL-17 receptor like pharmaceutical compositions in an ex vivo manner. In such instances, cells, tissues, or organs that have been removed from the patient are exposed to IL-17 receptor like pharmaceutical compositions after which the cells, tissues and/or organs are subsequently implanted back into the patient.

In other cases, an IL-17 receptor like polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent IL-17 receptor like gene, or an under expressed gene, and thereby produce a cell which expresses therapeutically efficacious amounts of IL-17 receptor like polypeptides.

It is further envisioned that IL-17 receptor like polypeptides can be produced in vitro or in vivo by homologous recombination, or with recombinant production methods utilizing control elements introduced into cells already containing DNA encoding IL-17 receptor polypeptides. For example, homologous recombination is a technique originally developed for targeting genes to induce or correct mutations in transcriptionally active genes (Kucherlapati, *Prog. in Nucl. Acid Res. & Mol. Biol.*, 36:301, 1989). The basic technique was developed as a method for introducing specific mutations into specific regions of the mammalian genome (Thomas et al., *Cell,* 44:419–428, 1986; Thomas and Capecchi, *Cell,* 51:503–512, 1987; Doetschman et al., *Proc. Natl. Acad. Sci.,* 85:8583–8587, 1988) or to correct specific mutations within defective genes (Doetschman et al., *Nature,* 330:576–578, 1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a IL-17 receptor like polypeptide, e.g., flanking sequences. For example, a promoter/enhancer element, a suppresser, or an exogenous transcription modulatory element is inserted in the genome of the intended host cell in proximity and orientation sufficient to influence the transcription of DNA encoding the desired IL-17 receptor like polypeptide. The control element controls a portion of the DNA present in the host cell genome. Thus, the expression of the desired IL-17 receptor like polypeptide may be achieved not by transfection of DNA that encodes the IL-17 receptor like gene itself, but rather by the use of targeting DNA (containing regions of homology with the endogenous gene of interest) coupled with DNA regulatory segments that provide the endogenous gene sequence with recognizable signals for transcription of an IL-17 receptor like polypeptide.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, IL-17 receptor like polypeptide production from a cell's endogenous IL-17 receptor like gene involves first using homologous recombination to place a recombination sequence from a site-specific recombination system (e.g., Cre/loxP, FLP/FRT) (Sauer, *Current Opinion In Biotechnology,* 5:521–527, 1994; Sauer, *Methods In Enzymology,* 225:890–900, 1993) upstream (that is, 5' to) of the cell's endogenous genomic IL-17 receptor like polypeptide coding region. A plasmid containing a recombination site homologous to the site that was placed just upstream of the genomic IL-17 receptor like polypeptide coding region is introduced into the modified cell line along with the appropriate recombinase enzyme. This recombinase causes the plasmid to integrate, via the plasmid's recombination site, into the recombination site located just upstream of the genomic IL-17 receptor like polypeptide coding region in the cell line (Baubonis and Sauer, *Nucleic Acids Res.,* 21:2025–2029, 1993; O'Gorman et al., *Science,* 251: 1351–1355, 1991). Any flanking sequences known to increase transcription (e.g., enhancer/promoter, intron, translational enhancer), if properly positioned in this plasmid, would integrate in such a manner as to create a new or modified transcriptional unit resulting in de novo or increased IL-17 receptor like polypeptide production from the cell's endogenous IL-17 receptor like gene.

A further method to use the cell line in which the site specific recombination sequence had been placed just upstream of the cell's endogenous genomic IL-17 receptor like polypeptide coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer, *Current Opinion In Biotechnology, supra,* 1994; Sauer, *Methods In Enzymology, supra,* 1993) that would create a new or modified transcriptional unit resulting in de novo or increased IL-17 receptor like polypeptide production from the cell's endogenous IL-17 receptor like gene.

An additional approach for increasing, or causing, the expression of IL-17 receptor like polypeptide from a cell's endogenous IL-17 receptor like gene involves increasing, or causing, the expression of a gene or genes (e.g., transcription factors) and/or decreasing the expression of a gene or genes (e.g., transcriptional repressors) in a manner which results in de novo or increased IL-17 receptor like polypeptide production from the cell's endogenous IL-17 receptor like gene. This method includes the introduction of a non-naturally occurring polypeptide (e.g., a polypeptide comprising a site specific DNA binding domain fused to a transcriptional factor domain) into the cell such that de novo or increased IL-17 receptor like polypeptide production from the cell's endogenous IL-17 receptor like gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence encoding an IL-17 receptor like polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell and will hybridize to its homologous region within the genome. If this hybridization occurs during DNA replication, this piece of DNA, and any additional sequence attached thereto, will act as an Okazaki fragment and will be incorporated into the newly C synthesized daughter strand of DNA. The present invention, therefore, includes nucleotides encoding a IL-17 receptor like polypeptide, which nucleotides may be used as targeting sequences.

IL-17 receptor like polypeptide cell therapy, e.g., the implantation of cells producing IL-17 receptor like polypeptides, is also contemplated. This embodiment involves implanting cells capable of synthesizing and secreting a biologically active form of IL-17 receptor like polypeptide. Such IL-17 receptor like polypeptide-producing cells can be cells that are natural producers of IL-17 receptor like polypeptides or may be recombinant cells whose ability to produce IL-17 receptor like polypeptides has been augmented by transformation with a gene encoding the desired IL-17 receptor like polypeptide or with a gene augmenting the expression of IL-17 receptor like polypeptide. Such a modification may be accomplished by means of a vector suitable for delivering the gene as well as promoting its expression and secretion. In order to minimize a potential immunological reaction in patients being administered an IL-17 receptor like polypeptide, as may occur with the administration of a polypeptide of a foreign species, it is preferred that the natural cells producing IL-17 receptor like polypeptide be of human origin and produce human IL-17 receptor like polypeptide. Likewise, it is preferred that the recombinant cells producing IL-17 receptor like polypeptide be transformed with an expression vector containing a gene encoding a human IL-17 receptor like polypeptide.

Implanted cells may be encapsulated to avoid the infiltration of surrounding tissue. Human or non-human animal cells may be implanted in patients in biocompatible, semi-permeable polymeric enclosures or membranes that allow the release of IL-17 receptor like polypeptide, but that prevent the destruction of the cells by the patient's immune system or by other detrimental factors from the surrounding tissue. Alternatively, the patient's own cells, transformed to produce IL-17 receptor like polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO95/05452; PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538, 5,011,472, and 5,106,627. A system for encapsulating living cells is described in PCT Application no. PCT/US91/00157 of Aebischer et al. See also, PCT Application no. PCT/US91/00155 of Aebischer et al., Winn et al., *Exper. Neurol.*, 113:322–329 (1991), Aebischer et al., *Exper. Neurol.*, 111:269–275 (1991); and Tresco et al., *ASAIO*, 38:17–23 (1992).

In vivo and in vitro gene therapy delivery of IL-17 receptor like polypeptides is also envisioned. One example of a gene therapy technique is to use the IL-17 receptor like gene (either genomic DNA, cDNA, and/or synthetic DNA) encoding a IL-17 receptor like polypeptide which may be operably linked to a constitutive or inducible promoter to form a "gene therapy DNA construct". The promoter may be homologous or heterologous to the endogenous IL-17 receptor like gene, provided that it is active in the cell or tissue type into which the construct will be inserted. Other components of the gene therapy DNA construct may optionally include, DNA molecules designed for site-specific integration (e.g., endogenous sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the IL-17 receptor like gene in the target cell. Such elements are turned on in response to an appropriate effector. In this way, a therapeutic polypeptide can be expressed when desired. One conventional control means involves the use of small molecule dimerizers or rapalogs (as described in WO9641865 (PCT/US96/099486); WO9731898 (PCT/US97/03137) and WO9731899 (PCT/US95/03157) used to dimerize chimeric proteins which contain a small molecule-binding domain and a domain capable of initiating biological process, such as a DNA-binding protein or transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science* 287:816–817, and 826–830 (2000).

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand binding domain is modified to eliminate the ability of the receptor to bind to the natural ligand. The modified steroid hormone receptor system is further described in U.S. Pat. No. 5,364,791; WO9640911, and WO9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding an IL-17 receptor like polypeptide into cells via local injection of an IL-17 receptor like nucleic acid molecule or by other appropriate viral or non-viral delivery vectors. Hefti, *Neurobiology*, 25:1418–1435 (1994). For example, a nucleic acid molecule encoding an IL-17 receptor like polypeptide may be contained in an adeno-associated virus (AAV) vector for delivery to the targeted cells (e.g., Johnson, International Publication No. WO95/34670; International Application No. PCT/US95/07178). The recombinant AAV genome typically contains AAV inverted terminal repeats flanking a DNA sequence encoding an IL-17 receptor like polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that IL-17 receptor like gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous IL-17 receptor like polypeptide expression in a cell via gene therapy is to insert one or more enhancer elements into the IL-17 receptor like polypeptide promoter, where the enhancer element(s) can serve to increase transcriptional activity of the IL-17 receptor like gene. The enhancer element(s) used will be selected based on the tissue in which one desires to activate the gene(s); enhancer elements known to confer promoter activation in that tissue will be selected. For example, if a gene encoding a IL-17 receptor like polypeptide is to be "turned on" in T-cells, the lck promoter enhancer element may be used. Here, the functional portion of the transcriptional element to be added may be inserted into a fragment of DNA containing the IL-17 receptor like polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy also can be used to decrease IL-17 receptor like polypeptide expression by modifying the nucleotide sequence of the endogenous promoter(s). Such modification is typically accomplished via homologous recombination methods. For example, a DNA molecule containing all or a portion of the promoter of the IL-17 receptor like gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding IL-17 receptor like gene. The deletion of the TATA box or the transcription activator binding site in the promoter may be accomplished by generating a DNA construct comprising all or the relevant portion of the IL-17 receptor like polypeptide promoter(s) (from the same or a related species as the IL-17 receptor like gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Additional Uses of IL-17 Receptor Like Nucleic Acids and Polypeptides

Nucleic acid molecules of the present invention (including those that do not themselves encode biologically active polypeptides) may be used to map the locations of the IL-17 receptor like gene and related genes on chromosomes. Mapping may be done by techniques known in the art, such as PCR amplification and in situ hybridization.

IL-17 receptor like nucleic acid molecules (including those that do not themselves encode biologically active polypeptides), may be useful as hybridization probes in diagnostic assays to test, either qualitatively or quantitatively, for the presence of an IL-17 receptor like DNA or corresponding RNA in mammalian tissue or bodily fluid samples.

Other methods may also be employed where it is desirable to inhibit the activity of one or more IL-17 receptor like polypeptides. Such inhibition may be effected by nucleic acid molecules which are complementary to and hybridize to expression control sequences (triple helix formation) or to IL-17 receptor like mRNA. For example, antisense DNA or RNA molecules, which have a sequence that is complementary to at least a portion of the selected IL-17 receptor like gene(s) can be introduced into the cell. Antisense probes may be designed by available techniques using the sequence of IL-17 receptor like polypeptide disclosed herein. Typically, each such antisense molecule will be complementary to the start site (5' end) of each selected IL-17 receptor like gene. When the antisense molecule then hybridizes to the corresponding IL-17 receptor like mRNA, translation of this mRNA is prevented or reduced. Antisense inhibitors provide information relating to the decrease or absence of an IL-17 receptor like polypeptide in a cell or organism.

Alternatively, gene therapy may be employed to create a dominant-negative inhibitor of one or more IL-17 receptor like polypeptides. In this situation, the DNA encoding a mutant polypeptide of each selected IL-17 receptor like polypeptide can be prepared and introduced into the cells of a patient using either viral or non-viral methods as described herein. Each such mutant is typically designed to compete with endogenous polypeptide in its biological role.

In addition, an IL-17 receptor like polypeptide, whether biologically active or not, may be used as an immunogen, that is, the polypeptide contains at least one epitope to which antibodies may be raised. Selective binding agents that bind to an IL-17 receptor like polypeptide (as described herein) may be used for in vivo and in vitro diagnostic purposes, including, but not limited to, use in labeled form to detect the presence of IL-17 receptor like polypeptide in a body fluid or cell sample. The antibodies may also be used to prevent, treat, or diagnose a number of diseases and disorders, including those recited herein. The antibodies may bind to an IL-17 receptor like polypeptide so as to diminish or block at least one activity characteristic of an IL-17 receptor like polypeptide, or may bind to a polypeptide to increase at least one activity characteristic of an IL-17 receptor like polypeptide (including by increasing the pharmacokinetics of the IL-17 receptor like polypeptide).

EXAMPLE 1

Cloning of a First IL-17 Receptor Like Polypeptide

A 477 base pair EST sequence (termed "zhgb-aa287951"), was identified from the Amgenesis database. The 1392 bp full-length nucleotide sequence of zhgb-aa287951 was then determined. PCR was performed for screening a plurality of human cDNA libraries. The human cDNA libraries were prepared as follows: total RNA was extracted from various human tissues using standard RNA extraction procedures and poly-A$^+$ RNA was selected from this total RNA using standard procedures known to those skilled in the art. Random primed or oligo(dT) primed cDNA was synthesized from this poly-A$^+$ RNA using the procedure in the manual of the Superscript Plasmid System for cDNA Synthesis and Plasmid Cloning kit (Gibco-BRL, Inc., Rockville, Md.) or using other suitable procedures known to those skilled in the art. The resulting cDNA was digested with appropriate restriction enzymes to create sticky o assist in ligation to a cloning vector. This digested cDNA was ligated into the PSPORT 1 cloning vector, or another suitable cloning vector known to those skilled in the art, that had been pre-digested with appropriate restriction enzymes. The ligation products were transformed into *E. coli* using standard techniques known in the art, and transformants were selected on bacterial media plates containing either ampicillin, tetracycline, kanamycin or chloramphenicol, depending upon the specific cloning vector used. The cDNA library consisted of all, or a subset, of these transformants.

Both 5'- and 3'—end RACE was carried out using plasmid DNAs prepared from positive libraries as template using a touchdown protocol as follows. Briefly, the PCR conditions were as follows: 94° for 30 seconds; 5 cycles of 94° for 5 seconds and 72° for 2 minutes; 5 cycles of 94° for 5 seconds and 70° for 2 minutes; 25 cycles of 94° for 5 seconds and 68° for 2 minutes 30 seconds; followed by a final extension of 72° for 7 minutes and 4° hold. This reaction used 50 ng of each cDNA library, 10 pmol of each primer, 200 µM dNTP's (final concentration), and a 1× concentration of Clontech's Advantage-HF2 cDNA Polymerase Mix (Cat# K1914-1) in a 50 µl final volume. A nested PCR reaction was done on the primary RACE products. The final PCR products were then subcloned and their nucleotide sequences determined. The PCR-derived DNA fragments were used as probes for screening cDNA libraries and cloning of the cDNA for this gene. PCR was used for both 5' RACE and 3' RACE reactions on the seven positive libraries using a touchdown protocol. The 5' RACE primers used gene specific primer 2429-59 (5' GCA GAC ACT GAG AGC ATT GTA ATC-3'; SEQ ID NO: 8) and a library vector (PCMV-SPORT) primer 1916-83 (5'-GGC TCG TAT GTT GTG TGG AAT TGT GAG CG-3'; SEQ ID NO: 9). The 3' RACE primers used gene specific primer 2429-56 (5'-AGG ATC AAA ACT TTC TTT TCT AC-3': SEQ ID NO: 10) and a library vector primer 1918-80 (5'-TGC AAG GCG ATT AAG TTG GGT AAC GCC AG-3'; SEQ ID NO: 11).

The PCR conditions were the same as described above. A nested PCR reaction was done on the above sample using 5 µl of a 1:50 dilution of the first round PCR 5' and 3' RACE products, 10 pmol each of a nested gene specific primer and a nested vector primer. For 5'-nested RACE the gene specific and vector primers were 5'-GCC GAC GGG GAC GTG GAT GAA C-3' (SEQ ID NO: 12)and 5'-CAT GAT TAC GCC AAG CTC TAA TAC GAC TC-3' (SEQ ID NO: 13), respectively. For the 3'-nested RACE the primers were 5'-CTT CGC CGA GTG CCT GTG CAG-3' (SEQ ID NO: 14) and 5'-TCA CGA CGT TGT AAA ACG ACG GCC AGT G-3' (SEQ ID NO: 15), respectively). The remaining reagents and PCR reaction protocol were identical to those used for the primary RACE reactions.

Ten microliters of the final product from the nested RACE was run on a 1% TBE agarose gel at 5V/cm. Well defined single bands were isolated from the gel and purified using the Qiagen gel extraction kit (Cat#28704) and submitted for sequencing.

EXAMPLE 2

Cloning of Second and Third IL-17 Receptor Like Isoforms

For cloning of the second and the third isoforms of the IL-17 receptor like molecule, two new gene specific primers were used for further PCR reaction on the positive libraries. These primers were as follows: 2469-50 (5'-GCG ATG TCG CTC GTG CTG CTA AG-3'; SEQ ID NO: 16) and 2469-54 (5'-GCA GCC TGG TGA GGT GAA ATT CAC-3'; SEQ ID NO: 17). The PCR conditions used in these reactions were as follows: 94° for 2 minutes; 35 cycles of 94° for 30 seconds, 66° for 30 seconds and 72° for 45 seconds, followed by a final extension of 72° for 7 minutes and 4° hold. This reaction used 50 ng of each cDNA library, 10 pmol of each primer, 200 µM dNTP's (final concentration), and a 1× concentration of Clontech's Advantage-HF2 cDNA Polymerase Mix (Cat# K1914-1) in a 50 µl final volume.

Ten microliters of the product was run on a 1% TBE agarose gel at 5V/cm. Well defined single bands were isolated from the gel and purified using the Qiagen gel extraction kit (Cat#28704) and submitted for sequencing.

EXAMPLE 3

Presence and Distribution of mRNA in Different Tissues

PCR was used to screen a panel of 77 human tissue libraries prepared by using 2.5 pmol each of primers 2429-56 and 2429-59 and 50 ng library cDNA (Ready-to-go PCR Beads Amersham Pharmacia Biotech Cat#27-9553). PCR Conditions were 94° for 2 minutes; followed by 35 cycles of 94° for 30 seconds; 66° For 30 seconds; 72° for 45 seconds; final extension of 72° for 7 minutes and 4° hold. A 440 bp band was identified in 40 sources with varying signal intensity. The results were as follows:

| Tissue Source | Level of expression |
|---|---|
| Fetal pancrease | +++ |
| Fetal scalp | +++ |
| Fetal gall bladder | +++ |
| Cerebellum | +++ |
| Pons/medulla | +++ |
| (midbrain) LNV block 10 | +++ |
| lymphoma cell lines | +++ |
| Prostate tumor T1175 | +++ |
| Prostate tumor T1940 | +++ |
| Colon tumor T24 | +++ |
| Ovary tumor T22 | +++ |
| Colon tumor T25 | +++ |
| Fetal stomach | ++ |
| Fetal bladder | ++ |
| Fetal kidney | ++ |
| Fetal liver | ++ |

-continued

| Tissue Source | Level of expression |
|---|---|
| Fetal ovary | ++ |
| Fetal femur | ++ |
| Fetal calveria | ++ |
| Fetal mesentery | ++ |
| Fetal spleen | ++ |
| Fetal lung | ++ |
| Fetal heart | ++ |
| Forebrain | ++ |
| Testis | ++ |
| Trachea | ++ |
| Bone (limb) | ++ |
| Spinal column | ++ |
| Thalamus | ++ |
| (midbrain) LNV block 10 | ++ |
| Breast tumor T1485 | ++ |
| Breast tumor T1543 | ++ |
| Ovary tumor T23 | ++ |
| Lung tumor T27 | ++ |
| Adult T-cells | ++ |
| Cytoplasmic breast-Carcinoma cell lines | ++ |
| Fetal thymus | + |
| Placenta | + |
| Uterus | + |
| Normalized Fetal tissues | + |

EXAMPLE 4

Production of IL-17 Receptor Like Polypeptides

A. Bacterial Expression

PCR is used to amplify template DNA sequences encoding a IL-17 receptor like polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC No. 98113) containing the lux promoter and a gene encoding kanamycin resistance is digested with BamHI and NdeI for directional cloning of inserted DNA. The ligated mixture is transformed into an E. coli host strain by electroporation and transformants are selected for kanamycin resistance. Plasmid DNA from selected colonies is isolated and subjected to DNA sequencing to confirm the presence of the insert.

Transformed host cells are incubated in 2xYT medium containing 30 g/ml kanamycin at 30° C. prior to induction. Gene expression is induced by the addition of N-(3-oxohexanoyl)-dl-homoserine lactone to a final concentration of 30 ng/ml followed by incubation at either 30° C. or 37° C. for six hours. The expression of IL-17 receptor like polypeptide is evaluated by centrifugation of the culture, resuspension and lysis of the bacterial pellets, and analysis of host cell proteins by SDS-polyacrylamide gel electrophoresis.

Inclusion bodies containing IL-17 receptor like polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 ml of a Percoll solution (75% liquid Percoll. 0.15M NaCl) until uniformly suspended and then diluted and centrifuged at 21,600×g for 30 minutes.

Gradient fractions containing the inclusion bodies are recovered and pooled. The isolated inclusion bodies are analyzed by SDS-PAGE.

A single band on an SDS polyacrylamide gel corresponding to *E. coli* produced IL-17 receptor like polypeptide is excised from the gel, and the N-terminal amino acid sequence is determined essentially as described by Matsudaira et al., *J. Biol. Chem.*, 262:10–35 (1987).

B. Mammalian Cell Production

PCR is used to amplify template DNA sequences encoding a IL-17 receptor like polypeptide using primers corresponding to the 5' and 3' ends of the sequence. The primer sequences corresponding to the 5' and 3' ends are described above. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen, Carlsbad, Calif.), which contains an Epstein-Barr virus origin of replication, may be used for the expression of IL-17 receptor like in 293-EBNA-1 (Epstein-Barr virus nuclear antigen) cells. Amplified and gel purified PCR products are ligated into pCEP4 vector and lipofected into 293-EBNA cells. The transfected cells are selected in 100 g/ml hygromycin and the resulting drug-resistant cultures are grown to confluence. The cells are then cultured in serum-free media for 72 hours. The conditioned media is removed and, IL-17 receptor like polypeptide expression is analyzed by SDS-PAGE.

IL-17 receptor like polypeptide expression may be detected by silver staining. Alternatively, IL-17 receptor like polypeptide is produced as a fusion protein with an epitope tag, such as an IgG constant domain or a FLAG epitope, which may be detected by Western blot analysis using antibodies to the tag peptide.

IL-17 receptor like polypeptides may be excised from an SDS-polyacrylamide gel, or IL-17 receptor like fusion proteins are purified by affinity chromatography to the epitope tag, and subjected to N-terminal amino acid sequence analysis as described herein.

EXAMPLE 5

Production of Anti-IL-17 Receptor Like Polypeptide Antibodies

Antibodies to IL-17 receptor like polypeptides may be obtained by immunization with purified protein or with IL-17 receptor like peptides produced by biological or chemical synthesis. Suitable procedures for generating antibodies include those described in Hudson and Hay, Practical Immunology, 2nd Edition, Blackwell Scientific Publications (1980).

In one procedure for the production of antibodies, animals (typically mice or rabbits) are injected with a IL-17 receptor like antigen (such as a IL-17 receptor like polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells; ATCC no. CRL-1581), allowed to incubate in DMEM with 200 U/ml penicillin, 200 g/ml streptomycin sulfate, and 4 mM glutamine, then incubated in HAT selection medium (Hypoxanthine; Aminopterin; Thymidine). After selection, the tissue culture supernatants are taken from each well containing a hybridoma and tested for anti-IL-17 receptor like antibody production by ELISA.

Alternative procedures for obtaining anti-IL-17 receptor like antibodies may also be employed, such as the immunization of transgenic mice harboring human Ig loci for the production of human antibodies, and the screening of synthetic antibody libraries, such as those generated by mutagenesis of an antibody variable domain.

EXAMPLE 6

Recombinant Human IL-17 Receptor Like-Fc Fusion Protein

To prepare IL-17 receptor like-Fc fusion proteins, the extra-cellular domain of the human IL-17 receptor like polypeptide (amino acid #1-292 for IL-17RB-2, amino acid #1-350 for IL-17RB-3, SEQ ID NOS: 2 and 5 respectively) was fused to the human IgG1 heavy chain constant region (Fc). The DNA fragment encoding the human Fc (amino acid sequence set out in SEQ ID NO: 21) with a NotI restriction site at its 5' end and XhoI restriction site at its 31 end were directionally ligated into pCEP4 vector using NotI and XhoI sites. The resulting vector containing the Fc coding sequence in pCEP4 is referred to as pCEP4-Fc vector. DNA fragments encoding the extra-cellular domain of the human IL-17RB-2 or IL-17RB-3 (SEQ ID NOS: 2 and 5 respectively), with an Hind III restriction site and kozak sequence (CCACC) at their 5' end and a NotI restriction site at their 3' end, were generated by PCR. These DNA fragments were directionally ligated into the pCEP4-Fc expression vector using the Hind III and NotI restriction sites and were denoted as pCEP4-huIL-17RB-2 like-Fc or pCEP4-huIL-17RB-3 like-Fc. The integrity of the DNA and the junction sites were confirmed by DNA sequencing using standard methods known in the art.

The pCEP4-huIL-17RB-2 like-Fc plasmid or pCEP4-huIL-17RB-3 like-Fc plasmid (also denoted HIL-17RB-2-Fc and HIL 17RB-3-Fc, respectively, and deposited on Mar. 14, 2001 with the American Type Culture Collection, 10801 University Blvd., Manassas, Va. 20110, U.S.A. under Accession Nos. PTA-3174 and PTA-3178, respectively) were transiently transfected into human 293/EBNA cells using Superfect (Qiagen) according to the manufacturer's instructions. The serum-free conditioned media was harvested from the cells 72 hours after transfection. The recombinant human IL-17RB like-Fc fusion proteins, predicted to have the amino acid sequence APS located at the amino-terminus of the mature protein, were isolated by affinity chromatography using a HiTrap Protein G column (Amersham Pharmacia). The amino acid sequences of the resulting fusion proteins are set out in FIG. 22 (IL-17RB-2-Fc fusion protein; SEQ ID NO: 24) and FIG. 23 (IL-17RB-3Fc fusion protein; SEQ ID NO: 25).

The recombinant human IL-17RB like-Fc fusion proteins were dialyzed against PBS buffer for 72 hours at 4° C. using Spectra/Pore Membrane MWCO 10,000 (Spectrum Laboratories). Subsequently, the recombinant human IL-17RB like-Fc fusion proteins were electrophoresed on a 10' acrylamide gel (Novex) and stained with Coomassie-Blue. The stained gel was scanned with a denstitometer to determine the percent representation of the protein band of interest. Modified Lowry Protein Assay Reagent (Pierce) was used to determine the total protein concentration according to the manufacturer's instructions. Then, the amount of human IL-17 receptor like-Fc fusion protein were calculated by multiplying the percentage of IL-17RB like-Fc fusion proteins by the total protein concentration.

The IL-17RB fusion proteins can also be generated with an Epogen signal peptide (MGVHECPAWL-WLLLSLLSLPLGLPVLG (SEQ ID NO: 20) fused in frame into the predicted mature protein instead of fusing to the native extra-cellular domain as described above.

EXAMPLE 7

Recombinant Human IL-17E-Fc Fusion Protein

IL-17E was cloned as described in Example 1 of co-owned, concurrently filed U.S. patent application Ser. No. 09/810,384 entitled "IL-17 like Molecules and Uses Thereof", hereby incorporated by reference in its entirety. An Epogen signal peptide (EpoSP) fused in frame to the predicted mature protein of the human IL-17E (SEQ ID NO: 23) that was fused in frame to the IgG1 heavy chain constant region (Fc) was engineered as follows to make recombinant mature human IL-17E-Fc fusion protein. The EpoSP DNA encoding for the amino acid sequence MGVHECPAWL-WLLLSLLSLPLGLPVLG (SEQ ID NO: 20) was inserted into the pCEP4 expression vector (Invitrogen) in between a consensus Kozak sequence (CCACC) at its 5' end and an AscI site at its 3' end. In addition, the Fc DNA fragment encoding for the amino acid sequence set out in SEQ ID NO: 12 and a NotI restriction site at the 5' end of the sequence was inserted at the 3' end of the EpoSP (SEQ ID NO: 20). A thymidine was inserted immediately after the NotI restriction site in order to keep the coding frame the same. The resulting vector containing the EpoSP and the Fc in pCEP4 is referred to as pCEP4EpoSP-Fc vector.

A DNA fragment, containing an AscI restriction site at the 5' end and a NotI restriction site at the 3' end, coding for the mature human IL-17E protein (SEQ ID NO: 23) without the stop codon was generated by PCR. The mature human IL-17E protein starts at amino acid number 17 (aa17) with the starting methionine as amino acid number one. The AscI site, which contains a thymidine, was inserted immediately before the codon containing aa17 in order to keep the coding frame the same. The human IL-17E fragment was directionally ligated into the pCEP4-EpoSP-Fc expression vector using the AscI and NotI restriction sites and was denoted as pCEP4-EpoSP-huIL-17E -Fc. The integrity of the DNA and the junction sites were confirmed by DNA sequencing using standard methods known in the art.

The pCEP4-EpoSP-IL-17E-Fc plasmid was transiently transfected into human 293/EBNA cells using Superfect (Qiagen) according to the manufacturer's instructions. The serum-free conditioned media was harvested from the cells 72 hours after transfection. The recombinant human IL-17E-Fc fusion protein, predicted to have the amino acid sequence APS located at the amino-terminus of the mature protein, was isolated by affinity chromatography using a HiTrap Protein G column (Amersham Pharmacia). The recombinant human IL-17E-Fc fusion protein was then dialyzed against PBS buffer for 72 hours at 4° C. using Spectra/Pore Membrane MWCO 10,000 (Spectrum Laboratories). Subsequently, the recombinant human IL-17E-Fc fusion protein was electrophoresed on a 10% acrylamide gel (Novex) and stained with Coomassie-Blue. The stained gel was scanned with a densitometer to determine the percent representation of the protein band of interest. Modified Lowry Protein Assay Reagent (Pierce) was used to determine the total protein concentration according to the manufacturer's instructions. Then, the amount of human IL-17E-Fc fusion protein was calculated by multiplying the percentage of IL-17E -Fc fusion protein by the total protein concentration.

EXAMPLE 8

IL-17E Polypeptide Binds to the IL-17 Receptor Like Polypeptides

To determine if IL-17E polypeptide (SEQ ID NO: 23) is a ligand for the IL-17 receptor like polypeptides (SEQ ID NO: 2 and/or 5; IL-17RB-2 and/or IL-17RB-3 respectively), competitive binding assays were performed with the human B-lymphoblast cell line GM3104A which has been shown to express IL-17 receptor like polypeptide by Northern Blot and RT-PCR analyses. The conditioned media from 293E cells transfected to express IL-17E-Fc fusion protein (SEQ ID NO: 23), prepared as described in Example 7 above, was collected, concentrated and used for the binding assay. Specificity of ligand binding was determined by competition with soluble blocking receptors, either IL-17RB-2-Fc or IL-17RB-3-Fc fusion proteins (SEQ ID NOS: 22 or 23, respectively). IL-17R-Fc fusion protein (consisting of the extracellular domain of SEQ ID NO: 3) was purified from conditioned media collected from transfected 293E cells and used as a control. Conditioned media from 293E cells transfected with IL-17RB-2-Fc or IL-17-RB-3-Fc (deposited with the ATCC on Mar. 14, 2001 under Accession Nos. PTA-3174 and PTA-3178 respectively), as described in Example 6 above, was concentrated (5×) with an Amicon 3 Kd cut-off Centracon (#4203) and used for blocking.

Prior to the binding assay, 0.5 ml of IL-17E-Fc fusion protein containing (1×) conditioned media was added into vials each containing 0.5 ml 5× conditioned media of IL-17RB-2-Fc, IL-17RB-3-Fc, or 0.5 ml of 5 µg/ml IL-17R-Fc protein in RPMI 1640. Each vial was incubated on ice for 2 hours.

Subsequently, GM3104A cells ($1 \times 10^6$ cells per sample) were incubated with 1 ml of 8% FBS/PBS, at 4° C. for 1 hour. The cells were then washed with 0.5% BSA/PBS and incubated with 1 ml of untransfected 293E cell conditioned media, conditioned media containing IL-17E-Fc or conditioned media containing IL-17E-Fc pre-incubated with blocking receptor (IL-17RB-2 or IL-17RB-3) for 2 hours at 4° C. with gentle shaking. After the incubation, the cells were washed 3 times with 1 ml of ice-cold 0.5% BSA/PBS.

Each cell sample was stained with 2 µg/100 µl goat anti human IgG-Fc-FITC (Chemicon, AP113F)diluted in 0.5% BSA/PBS. The cells were incubated on ice for 1 hour and washed 3 times with 1 ml of ice-cold 0.5% BSA/PBS. Subsequently, ligand binding was detected with fluorescence-activated cell sorter analysis using FACScan (Becton Dickinson). This analysis indicated that IL-17E-FC fusion protein bound to GM3104A cells. This binding was inhibited by IL-17RB-2 and IL-17RB-3 (isoforms of the present invention) but not IL-17 R.

EXAMPLE 10

IL-17E Polypeptide Induces Expression of Proinflammatory Cytokines

Since IL-17E polypeptide has been shown to bind to the IL-17 receptors of the present invention (SEQ ID NO: 2 and 5), effects of IL-17E polypeptide on the expression of pro-inflammatory cytokines can be correlated with activation of the IL-17 receptors of the present invention.

The conditioned media from 293E cells expressing either IL-17E-Fc fusion protein, IL-17B-Fc, IL-17C-Fc or IL-17D-Fc, was collected to use as ligand in the assay. Conditioned media containing IL-17B-Fc, IL-17C-Fc, IL-17D-Fc, and IL-17E-Fc were then concentrated (15×) using a 3 Kd cut-off Centracon(Amicon, #4032), and reconstituted to 1× medium by adding fresh 20% FBS/1640 media.

Human B-lymphoblast cells (GM3104A, 1×10$^6$ cell/sample) were cultured in reconstituted concentrated condition media which contained each IL-17 ligand (IL-17E-Fc polypeptide, IL-17B-Fc, IL-17C-Fc, IL-17D-Fc and human Fc). After incubation for 18 hours at 37° C. and 5% $CO_2$, the media were collected and the amount of IL-1α, IL-1β, IL-6, IFN-γ, G-CSF, and TNF-α released into the media was measured with the appropriate Quantikine Immunoassay kit (R&D Systems) following the manufacturer's instructions. The results are summarized in table III. IL-17E-FC fusion protein induced the release of TNF-α, IL-1α, and IL-6 to a much greater extent than the other IL-17 ligands tested. Induction of IL-1β, IFN-γ, and G-CSF was not detected for any of the ligands.

TABLE III

| Ligand | TNF-α (pg/ml) | IL-1α (pg/ml) | IL-6 (pg/ml) |
| --- | --- | --- | --- |
| Mock CM | 190 | 6 | 157.6 |
| Human Fc | 210 | 8 | 199 |
| IL-17B | 180 | 11 | 138 |
| IL-17C | 170 | 8 | 152 |
| IL-17D | 180 | 22 | 155 |
| IL-17 like | 460 | 25 | 362 |

EXAMPLE 9

IL-17E Overexpressing Transgenic Mice

As described in Example 7, IL-17E polypeptide is a ligand for the IL-17 like receptors of the present invention. The following examples describe transgenic mice which are overexpressing IL-17E polypeptide. The information from these mice is useful in determining the biological effects of activation and/or overexpression of the IL-17 receptors of the present invention.

A. Transgene Preparation.

The coding region of human IL-17E cDNA (SEQ ID NO: 22) with an altered Kozak sequence, CCACC, immediately upstream of the initiating ATG, was ligated into a liver-specific expression vector. The expression vector consisted of a 774-bp DNA fragment containing the hepatocyte control region (HCR) from the human apolipoprotein (apo) C—I/C—I' intergenic region on chromosome 19 (Simonet et al., *J. Biol. Chem.*, 268:8221–8229, 1993). The vector also contained a 1450-bp continuous piece of DNA which consisted of the human apoE gene 5'-flanking sequence, the first exon, the first intron and a portion of the second exon of the apoE gene (Simonet et al., *J. Clin. Invest.*, 94:1310–1319, 1994). An SV40 polyadenylation signal was located downstream of the cDNA insert sites. The integrity of the cDNA was verified by sequencing using standard methods known in the art.

B. Preparation and Analysis of IL-17E Overexpressing Transgenic Mice.

The resulting plasmid (denoted herein as ApoE-hIL-17) was purified and the transgene insert was isolated for microinjection. Single-cell embryos from BDF1×BDF1-bred mice were injected essentially as described in Brinster et al. (*Proc. Natl. Acad. Sci. USA*, 82:4438–4442, 1985). Embryos were cultured overnight in a 37° C. and 5% $CO_2$ incubator. Subsequently, 15 to 20 2-cell embryos were transferred to the oviducts of thirteen pseudopregnant CD1 female mice. Transgenic offsprings were identified by PCR screening with primers that amplify a 368-bp fragment of the human apoE first intron from DNA prepared from ear biopsies as described in Simonet et al. (*J. Clin. Invest.*, 94:1310–1319, 1994).

EXAMPLE 11

Necropsy Analysis of IL-17E Overexpressing Transgenic Mice

At 8–10 weeks of age, 10 IL-17E overexpressing transgenic mice and five non-transgenic littermates were necropsied. Liver samples from the mice were flash frozen in liquid nitrogen at the time of necropsy. RNAs were isolated from each sample using the Perfect RNA Kit (Eppendorf)according to the manufacturer's instructions and analyzed by Northern blot analysis.

The Northern blot was generated by running 10 µg of RNA diluted in 1×RNA Loading Dye (Sigma) on a 1% formaldehyde-agarose gel. The gel was denatured in 50 mM NaOH and 150 and 55 mM NaCl. Subsequently, the gel was neutralized in 0.1 M Tris-HCl (pH 7.0) and 150 mM NaCl and blotted onto a Duralon membrane according to the manufacturer's instructions (Stratagene). The Northern blot was probed with a $^{32}$P-labeled human IL-17E cDNA generated by the Rediprime System (Amersham). Hybridization was carried out in Express Hyb Solution and then washed according to the manufacturer's instructions. The hybridized blot was exposed to X-ray film (Kodak) for 72 hours at −80° C. and then developed.

The Northern blot analysis indicated that the transgenic founder mice had increased expression of the IL-17E RNA as compared with the non-transgenic littermates. Of the 10 mice tested, those denoted as nos. 29, 52, 55, 61 and 66 had the highest level of IL-17E RNA expression. (See FIG. 8)

B. Expression Analysis on the Remaining Founders

Livers from the remaining transgenic founder mice along with control mice, were obtained by partial hepatectomy. The mice were anesthesized by isoflourane and a small transverse incision below the xyphoid process on the sternum was made to expose the liver. A suture was placed around the lobe of liver selected for excision at the point of attachment. The lobe of liver was ligated and removed by cutting below the ligature and flash frozen in liquid nitrogen. The mouse was then checked for bleeding and the skin incision was closed with 1–2 autoclips (skin staples). RNA was isolation from the liver and Northern blot analysis was carried out as described above. The hybridized blot was exposed to X-ray film (Kodak) for 24 hours at −80° C. and then developed.

Northern blot analysis on the remaining founders indicated that these mice expressed higher levels of IL-17E RNA in the liver as compared with non-transgenic littermates.

Figure 9:
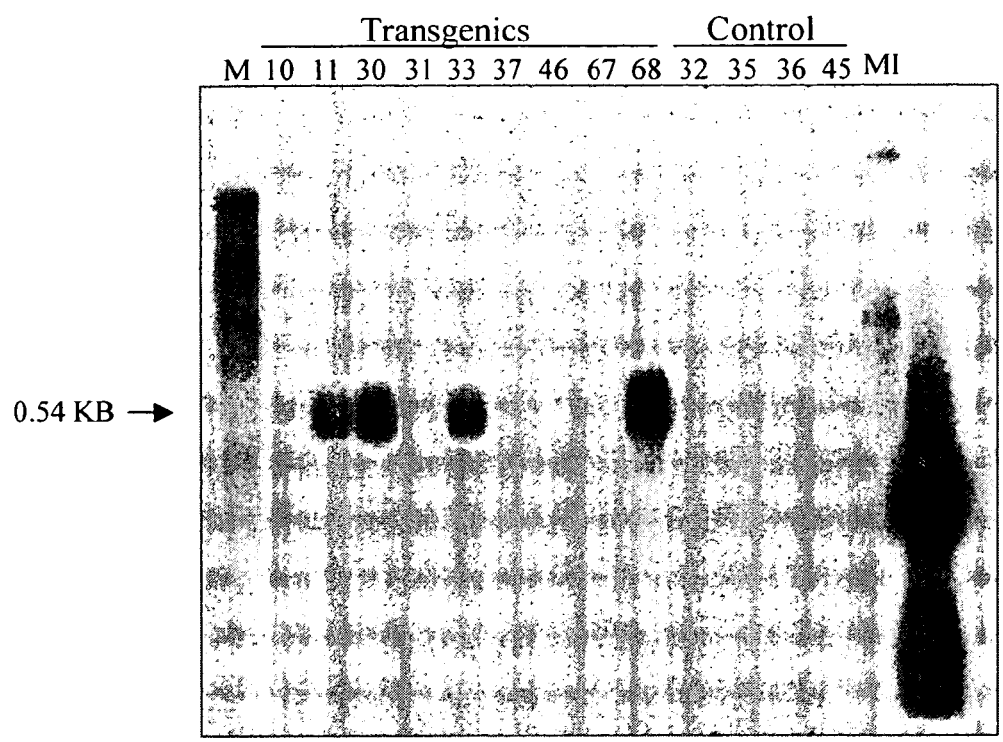
FIG. 9 depicts a Northern blot detecting expression of the IL-17 like overexpressing transgene in hepatectomized transgenic founder mice (nos. 10, 11, 30, 31, 33, 37, 46, 67, and 68). The control mice (nos. 32, 35, 36 and 45) are non-transgenic littermates. The lane marked "MI" represents the microinjection fragment which was loaded as a positive control. The presence of a 0.54 kb band is indicative of transgene expression.

The mice denoted as nos. 11, 30, 33, 46 and 68 expressed the highest levels of IL-17 RNA. (See FIG. 9).

EXAMPLE 12

Pathological Analysis of IL-17E Overexpressing Transgenic Mice

A. Necropsy

In this study, seven, 6–8 week old, IL-17E overexpressing mice as well as five, 6–8 week old, non-transgenic littermates (two males and three females) were pathologically analyzed for a potential IL-17E phenotype. Mice nos. 29, 52, 61 and 66 were strongly positive for hepatic expression of IL-17E mRNA, while mice nos. 1, 16 and 55 were weakly positive. The five non-trangenic control mice (nos. 2, 17, 28, 53 and 65) were negative. At necropsy, mice were weighed, blood was drawn for hematology and serum chemistries, and liver, spleen, kidney, heart, and thymus were weighed. Sections of liver, spleen, lung, brain, heart, kidney, adrenal, stomach, small intestine, pancreas, cecum, colon, mesenteric lymph node, skin, mammary gland, trachea, esophagus, thyroid, parathyroid, salivary gland, urinary bladder, ovary or testis, uterus or seminal vesicle, skeletal muscle, bone, and bone marrow were harvested for histologic analysis.

B. Histology

Sections of liver, spleen, lung, brain, heart, kidney, adrenal, stomach, small intestine, pancreas, cecum, colon, mesenteric lymph node, skin, mammary gland, trachea, esophagus, thyroid, parathyroid, salivary gland, urinary bladder, ovary or testis, uterus or seminal vesicle, skeletal muscle, bone, and bone marrow from the IL-17E transgenic and non-transgenic mice were fixed overnight in 10% neutral buffered zinc formalin (Anatech, Battle Creek, Mich.), paraffin embedded, sectioned at 3 μm, and stained with hematoxylin and eosin (H&E) for routine histologic examination.

C. Immunohistochemistry

Immunohistochemical staining was performed on 4 μm thick paraffin embedded sections using an automated DPC Mark 5 Histochemical Staining System (Diagnostic Products Corp, Randolph, N.J.). Deparaffinized tissue sections were blocked with CAS BLOCK (Zymed Laboratories, San Francisco, Calif.), incubated with a rat anti-mouse monoclonal antibody directed against macrophages (F4/80, Serotec Inc., Raleigh, N.C.) or a rat anti-mouse CD45R/B220 monoclonal antibody directed against all types of B cells (PharMingen, San Diego, Calif.). The primary antibody was detected using a biotinylated rabbit anti-rat immunoglobulin secondary antibody (Vector Laboratories, Burlingame, Calif.). Sections were then quenched with 3% hydrogen peroxide and reacted with an avidin-biotin complex tertiary (Vector Laboratories). The staining reaction was visualized with diaminobenzidine (DAB, Dako Carpinteria, Calif.) and sections were counterstained with hematoxylin.

D. Gross Pathology Findings

Mesenteric lymph nodes from the four high expressing IL-17E transgenic mice (nos. 29, 52, 61 and 66) plus one of the low expressing mice (no. 55) were markedly increased in size. Similarly, the spleens from these five IL-17E transgenic mice were enlarged and exhibited a significant increase in weight (1.08±0.27 SD % of body weight vs. 0.37±0.12 SD % of body weight in non-transgenic control mice, p=0.0007). Mesenteric lymph nodes and spleens from two other low expressing transgenic mice (nos. 1 and 16) appeared normal. The raw organ weight data is shown in Table IV and significant differences are summarized in Table VI.

TABLE IV

Raw Organ Weights for IL-17E Transgenic Mice vs. Non-Transgenic Mice

| Group | Sex | TBW | Liver | % BW | Spln | % BW | Heart | % BW | Kidneys | % BW | Thymus | % BW |
|---|---|---|---|---|---|---|---|---|---|---|---|---|
| Non-Transgenic | | | | | | | | | | | | |
| 2 | F | 21.8 | 0.923 | 4.23 | 0.070 | 0.32 | 0.121 | 0.56 | 0.351 | 1.61 | 0.061 | 0.28 |
| 17 | F | 20.5 | 0.912 | 4.45 | 0.089 | 0.43 | 0.112 | 0.55 | 0.273 | 1.33 | 0.048 | 0.23 |
| 28 | F | 22.5 | 1.125 | 5 | 0.123 | 0.55 | 0.127 | 0.56 | 0.398 | 1.77 | 0.058 | 0.26 |
| 53 | M | 25.8 | 1.315 | 5.1 | 0.076 | 0.29 | 0.140 | 0.54 | 0.423 | 1.64 | 0.031 | 0.12 |
| 65 | M | 29 | 1.45 | 5 | 0.082 | 0.28 | 0.169 | 0.58 | 0.523 | 1.8 | 0.055 | 0.19 |
| Mean | | | | 4.76 | | 0.37 | | 0.56 | | 1.63 | | 0.22 |
| St. Dev. | | | | 0.39 | | 0.12 | | 0.01 | | 0.19 | | 0.06 |
| IL-17E Transgenic | | | | | | | | | | | | |
| 1 | F | 31.9 | 1.406 | 4.41 | 0.118 | 0.37 | 0.151 | 0.47 | 0.433 | 1.36 | 0.071 | 0.22 |
| 16 | F | 22.5 | 1.121 | 4.98 | 0.085 | 0.38 | 0.115 | 0.51 | 0.350 | 1.56 | 0.061 | 0.27 |
| 29 | F | 24.4 | 1.439 | 5.90 | 0.333 | 1.36 | 0.123 | 0.5 | 0.861 | 3.53 | 0.061 | 0.25 |
| 52 | M | 25.6 | 1.583 | 6.18 | 0.223 | 0.87 | 0.129 | 0.5 | 0.356 | 1.39 | 0.074 | 0.29 |
| 55 | F | 19.1 | 1.181 | 6.18 | 0.196 | 1.03 | 0.122 | 0.64 | 0.388 | 2.03 | 0.04 | 0.21 |
| 61 | F | 24.5 | 1.401 | 5.72 | 0.190 | 0.78 | 0.118 | 0.48 | 0.372 | 1.52 | 0.059 | 0.24 |
| 66 | M | 25 | 1.47 | 5.88 | 0.338 | 1.35 | 0.162 | 0.65 | 0.433 | 1.73 | 0.026 | 0.1 |
| Mean | | | | 5.61 | | 0.88 | | 0.54 | | 1.87 | | 0.23 |
| St. Dev. | | | | 0.67 | | 0.41 | | 0.08 | | 0.76 | | 0.06 |

E. Hematology Findings

Four of the five IL-17E transgenic mice with enlarged mesenteric lymph nodes and spleens (the blood from mice nos. 29, 52, 55, 61 and 66 clotted and could not be evaluated) had moderate to marked increases in total leukocytes, neutrophils, lymphocytes, eosinophils, and large unstained cells (possibly large granular lymphocytes). The mean total leukocyte count for these four IL-17E transgenic mice was $11.93 \times 10^3$ ($4.47 \times 10^3$ SD) while non-transgenic control mice had a mean total leukocyte count of $3.09 \times 10^3$ ($\pm 0.79 \times 10^3$ SD, p=0.003). The mean neutrophil count in these four IL-17E transgenic mice was $2.29 \times 10^3$ ($\pm 0.67 \times 10^3$ SD) vs. $0.92 \times 10^3$ ($\pm 0.53 \times 10^3$ SD) in non-transgenic control mice, p=0.032. These four IL-17E transgenic mice had a mean lymphocyte count of $6.76 \times 10^3$ ($\pm 2.32 \times 10^3$) vs. $1.99 \times 10^3$ ($\pm 0.38 \times 10^3$ SD) in non-transgenic control mice, p=0.0025, a mean eosinophil count of $1.35 \times 10^3$ ($\pm 0.96 \times 10^3$ SD) vs.

$0.03 \times 10^3$ ($\pm 0.01 \times 10^3$ SD) in non-transgenic control mice, p=0.017, and a mean large unstained cell count of $1.41 \times 10^3$ ($\pm 1.11 \times 10^3$ SD) vs. $0.10 \times 10^3$ ($\pm 0.05 \times 0$ SD) in non-transgenic control mice, p=0.031. Two of the IL-17E transgenic mice (nos. 55 and 66) also had a mild anemia characterized by a slight decrease in red blood cell number, hemoglobin, and hematocrit as well as slightly elevated platelet counts. The raw hematology data is shown in Table 2 and significant differences are summarized in Table 3.

TABLE V

Raw Hematology Data for IL-17E Transgenic Mice vs. Non-Transgenic Mice

| Group | WBC | RBC | HGB | HCT | PLT | MPV | Neut | Lymph | Mono | Eos | Baso | LUC |
|---|---|---|---|---|---|---|---|---|---|---|---|---|
| Non-Transgenic | | | | | | | | | | | | |
| 2 | 2.52 | 9.39 | 13.9 | 48.9 | 1179 | 5.0 | 0.69 | 1.64 | 0.02 | 0.03 | 0.01 | 0.13 |
| 17 | 3.48 | 10.12 | 15.1 | 50.9 | 938 | 5.1 | 0.72 | 2.63 | 0.02 | 0.04 | 0.01 | 0.06 |
| 28 | 2.45 | 9.51 | 14.8 | 49.5 | 1013 | 5.7 | 0.37 | 2.00 | 0.02 | 0.01 | 0.01 | 0.05 |
| 53 | 2.70 | 10.67 | 16.1 | 55.9 | 1353 | 5.0 | 0.61 | 1.88 | 0.04 | 0.04 | 0.01 | 0.11 |
| 65 | 4.30 | 11.55 | 17.8 | 61.4 | 1362 | 4.5 | 2.20 | 1.81 | 0.11 | 0.02 | 0.01 | 0.16 |
| Mean | 3.09 | 10.25 | 15.5 | 53.3 | 1169 | 5.1 | 0.92 | 1.99 | 0.04 | 0.03 | 0.01 | 0.10 |
| St. Dev. | 0.79 | 0.89 | 1.5 | 5.3 | 193 | 0.4 | 0.73 | 0.38 | 0.04 | 0.01 | 0.00 | 0.05 |
| IL-17E Transgenic | | | | | | | | | | | | |
| 1 | 2.80 | 10.80 | 16.3 | 56.8 | 1113 | 5.2 | 0.69 | 1.91 | 0.03 | 0.02 | 0.01 | 0.14 |
| 16 | 3.49 | 10.29 | 15.8 | 54.7 | 1134 | 4.8 | 1.30 | 2.01 | 0.05 | 0.04 | 0.01 | 0.07 |
| 29 | No Sample | | | | | | | | | | | |
| 52 | 13.32 | 8.81 | 12.5 | 45.8 | 977 | 6.3 | 3.25 | 6.61 | 0.17 | 2.12 | 0.04 | 1.13 |
| 55 | 16.89 | 7.89 | 12.0 | 36.6 | 2758 | 5.4 | 1.84 | 9.80 | 0.09 | 2.14 | 0.04 | 2.99 |
| 61 | 11.32 | 9.18 | 14.1 | 50.0 | 1102 | 5.2 | 2.66 | 6.47 | 0.08 | 0.96 | 0.03 | 1.12 |
| 66 | 6.19 | 6.24 | 7.8 | 31.7 | 2195 | 4.4 | 1.42 | 4.16 | 0.05 | 0.16 | 0.01 | 0.40 |
| Mean | 9.00 | 8.87 | 13.1 | 45.9 | 1547 | 5.2 | 1.86 | 5.16 | 0.08 | 0.91 | 0.02 | 0.98 |
| SD | 5.71 | 1.66 | 3.1 | 10.0 | 744 | 0.6 | 0.94 | 3.06 | 0.05 | 1.01 | 0.02 | 1.09 |

Table VI Summary Data for Significant Differences in Organ Weights and CBC Values between IL-17E Transgenic Mice and Non-Transgenic mice

| | HEAGP Transgenic Mice (n = 4 or 5)* | Non-Transgenic Mice (n = 5) | p value (t Test) |
|---|---|---|---|
| Spleen Weight as % Body Weight | 1.08 ± 0.27 SD* | 0.37 ± 0.12 SD | 0.0007 |
| Total Leukocytes (WBCs) | $11.93 \times 10^3 \pm 4.47 \times 10^3$ SD | $3.09 \times 10^3 \pm 0.79 \times 10^3$ SD | 0.003 |
| Neutrophils | $2.29 \times 10^3 \pm 0.67 \times 10^3$ SD | $0.92 \times 10^3 \pm 0.53 \times 10^3$ SD | 0.032 |
| Lymphocytes | $6.76 \times 10^3 \pm 2.32 \times 10^3$ vs SD | $1.99 \times 10^3 \pm 0.38 \times 10^3$ SD | 0.0025 |
| Eosinophils | $1.99 \times 10^3 \pm 0.38 \times 10^3$ SD | $0.03 \times 10^3 \pm 0.01 \times 10^3$ SD | 0.017 |
| Large Unstained Cells (LUC - Possibly Large Granular Lymphocytes) | $1.41 \times 10^3 \pm 1.11 \times 10^3$ SD | $0.10 \times 10^3 \pm 0.05 \times 10^3$ SD | 0.031 |

F. Histopathologic Findings

Figure 10:
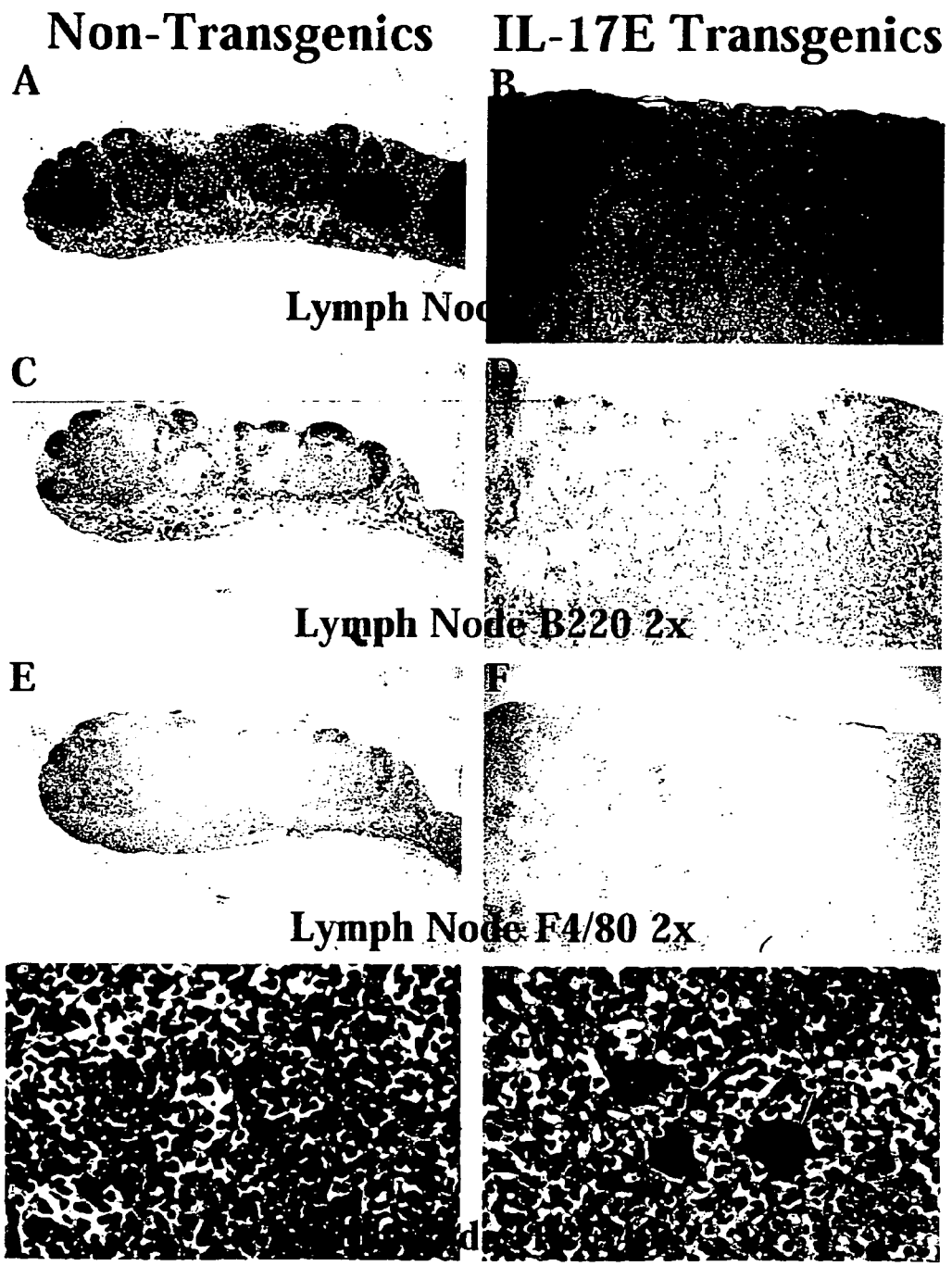
FIG. 10 depicts hematoxylin and eosin (A,B, G–J), 3220 (C,D) and F4/80 (E,F) stained sections of lymph node (A–H) or bone marrow (I,J) from IL-17 like transgenic mice (B,D,F,H) or non-transgenic control mice (A,C,E,G). Panels A–F illustrate that the IL-17 like transgenic lymph node was markedly enlarged with its normal architecture disrupted due to a marked cellular infiltrate (asterisk in panel B) that contained large numbers of 3220 positive B lymphocytes cells (panel D) and some F4/80 staining macrophages. Panel H illustrates that this cellular infiltrate also contained numerous eosinophils (arrowheads) as well as multinucleated inflammatory giant cells (arrows).

Hematoxylin and eosin stained sections of liver, spleen, lung, brain, heart, kidney, adrenal, stomach, small intestine, pancreas, cecum, colon, mesenteric lymph node, skin, mammary gland, trachea, esophagus, thyroid, parathyroid, salivary gland, urinary bladder, ovary or testis, uterus or seminal vesicle, skeletal muscle, bone, and bone marrow were examined from seven IL-17E transgenic mice and five non-transgenic control littermates. B220 (specific for all B cells) and F4/80 (specific for macrophages) immunostained sections of lymph node and spleen were also examined from all mice. Five of the IL-17E transgenic mice (nos. 29, 52, 55, 61 and 66) had similar histologic findings characterized by marked mesenteric lymphadenopathy, splenic lymphoid hyperplasia and red pulp eosinophilic myeloid hyperplasia, and bone marrow eosinophilic hyperplasia. The most striking histologic finding was the mesenteric lymphadenopathy, which was characterized by massive nodal enlargement with loss of normal nodal architecture and medullary expansion by a mixed population of inflammatory cells containing a large number of eosinophils, reactive B cells (stained with B220) and plasma cells, macrophages (stained with F4/80) and multinucleated inflammatory giant cells (See FIG. 10). These five IL-17E transgenic mice also exhibited marked bone marrow eosinophilic myeloid hyperplasia (FIG. 11B) as well as moderate to marked splenic B cell lymphoid hyperplasia and red pulp eosinophilic myeloid hyperplasia (FIG. 11F). In addition, one of the IL-17E transgenic mice (no.29) also exhibited marked, chronic eosinophilic and suppurative pyelonephritis with renal pelvic dilation in one kidney and moderate chronic eosinophilic and suppurative pyelitis in the other kidney (FIG. 11J), while another IL-17E transgenic mouse (no. 55) exhibited severe, chronic eosinophilic and suppurative urinary cystitis with mild bilateral chronic eosinophilic and suppurative pyelitis. Lastly, four of the IL-17E transgenic mice (nos. 29, 55, 61 and 66) exhibited minimal to mild eosinophilic and lymphoplasmacytic colitis and/or ileitis.

G. Summary of Phenotypic Findings in Transgenic Mice Overexpressing Human IL-17E Polypeptide Five of the IL-17E overexpressing transgenic mice (nos. 29, 52, 55, 61 and 66) had a similar phenotype, characterized by a leukocytosis with marked elevations in eosinophils, lymphocytes, and large unstained cells which may be large granular lymphocytes, a marked lymphadenopathy with a marked eosinophilic component, bone marrow eosinophilic myeloid hyperplasia, and splenic B cell lymphoid hyperplasia and eosinophilic myeloid hyperplasia. Two of the IL-17E transgenic mice (nos. 55 and 66) also exhibited mild anemia and thrombocytosis. In addition, IL-17E transgenic mice nos. 55 and 29, exhibited eosinophilic and superlative inflammation of their kidneys and/or urinary bladder. Lastly, four of the IL-17E ovewrexpressing transgenic mice (nos. 29, 55, 61 and 66) had minimal to mild eosinophilic and lymphoplasmacytic colitis and/or ileitis. All of these findings suggest that the IL-17E polypeptide plays a role in inflammation and myelopoiesis, particularly in the development, stimulation, and/or recruitment of eosinophils and B lymphocytes, and that the IL-17 receptor like polypeptides of the present invention, which bind to IL-17E, mediate this inflammation and myelopoiesis.

EXAMPLE 13

Transgenic Phenotype of IL-17E Overexpressing Mice

Phenotype analysis was performed on 10 transgenic mice and 5 non-transgenic littermates. A femur, peripheral blood (obtained by cardiac puncture) and a longitudinal half section of spleen were obtained from each transgenic mouse and their littermate control. Five of the trangenic mice analyzed (nos. 29, 52,55,61 and 66) exhibited phenotypic changes.

To analyze the phenotype of the transgenic mice, the major hematopoietic populations including activated T cells were quantitated. In addition, the tissue and lineage specific expression of IL-17 receptor like polypeptides of the present invention (IL-17RB), was quantitated as described in Antonysomy et al. (*J. Immunol.*, 162: 577–584, 1999) and as also described in Example 7 herein.

The following antibody panel was designed to make the above-identified measurements with fluorescent activated cell sorting (FACS). Helper T cells were detected with the antibody CD4-PE and were compared to an early activation marker detected by the antibody CD69-FITC. A pan T cell marker detected with antibody CD3-FITC was compared to killer T cells detected with the antibody CD8-PE Monocyte lineage cells detected with the antibody CD14-FITC was compared to B lineage cells (preB to mature surface immunoglobulin positive B cell) marker detected with the antibody CD19-PE. Granulocytes detected with the antibody GR-1-FITC were compared to natural killer cells detected with the antibody NK1.1-PE. The expression pattern of the IL-17 receptor like polypeptides (IL17RB), detected by binding of recombinant IL-17E-Fc fusion protein, was compared to B cells detected with the antibody CD45R-PE, to Helper T cells detected with the antibody CD4-PE, and to dendritic cells detected with the antibody CD11C-PE.

The transgenic mice and non-transgenic littermates were sacrificed and the femurs and spleens were dissected. Cell suspension from the femoral bone marrow and the spleen were made, washed twice and resuspended in PBS/0.5% BSA. The cell number of each cell suspension was quantitated with a Coulter Z1 Coulter Counter using a 100 μm aperture and a lower threshold setting of 4 μm. A 10 μl alloquot of each cell suspension was added to 10 ml of Isoton buffer containing 3 drops of Zapoglobin (to lyse the red blood cells) and counted. The cell suspensions were incubated with Fc-block (CD 16/32) for 15 minutes at 4° C.

Subsequently, $1 \times 10^6$ cells (suspended in PBS/0.5% BSA) were added to each antibody-containing well on a 96 well plate.

In addition, peripheral blood samples from the transgenic mice and non-transgenic littermates were obtained by cardiac puncture and CBC analysis was performed. Subsequently, the remaining blood was divided equally among 8 wells containing the antibodies on a 96 well plate.

The cell suspensions and blood samples were incubated in the presence of the antibodies for 30 minutes at room temperature. Subsequently, the cells were washed twice and lysed with FACS lysing buffer (200 μl/well; Becton Dickinson) for 15 minutes at room temperature in order to eliminate the red blood cells. After lysing, the cells were washed and resuspended in 400 μl of FACS buffer and analyzed by flow cytometry.

Figure 12:
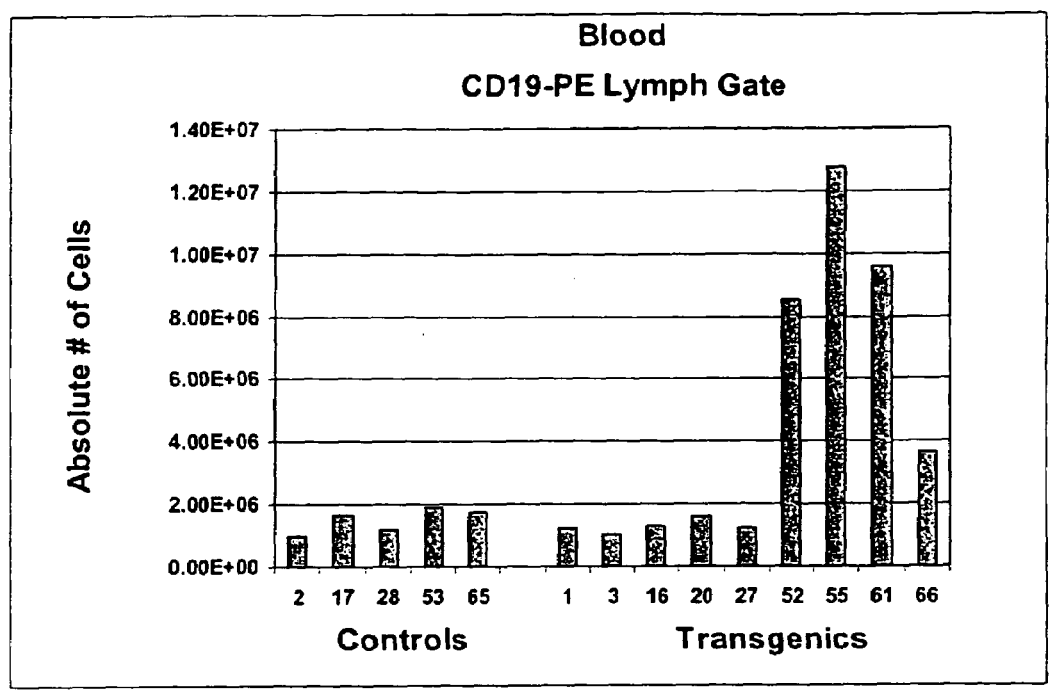
FIG. 12 depicts a bar chart histogram showing a significant increase in absolute numbers of CD19+ B lymphocytes in the peripheral blood of 4 out of 9 IL-17 like transgenic mice as compared to the non-trangenic littermate controls.
Figure 13:
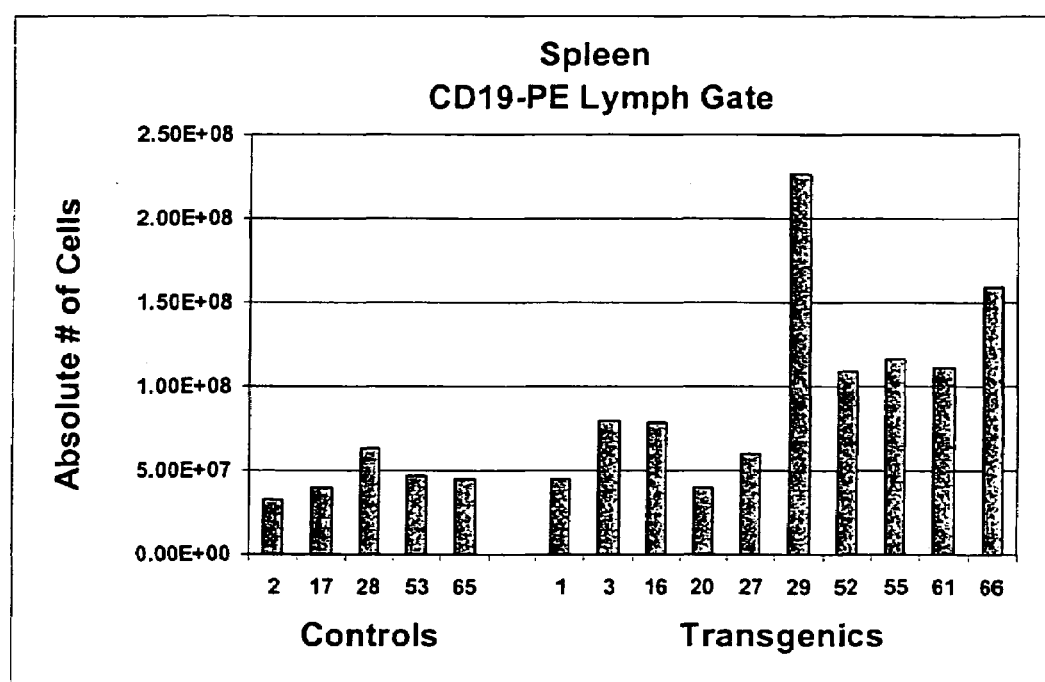
FIG. 13 depicts a bar chart histogram showing an increase in absolute numbers of CD19+ B lymphocytes in the spleens of 5 out of 10 IL-17 like transgenic mice as compared to the non-transgenic littermate controls.
Figure 14:
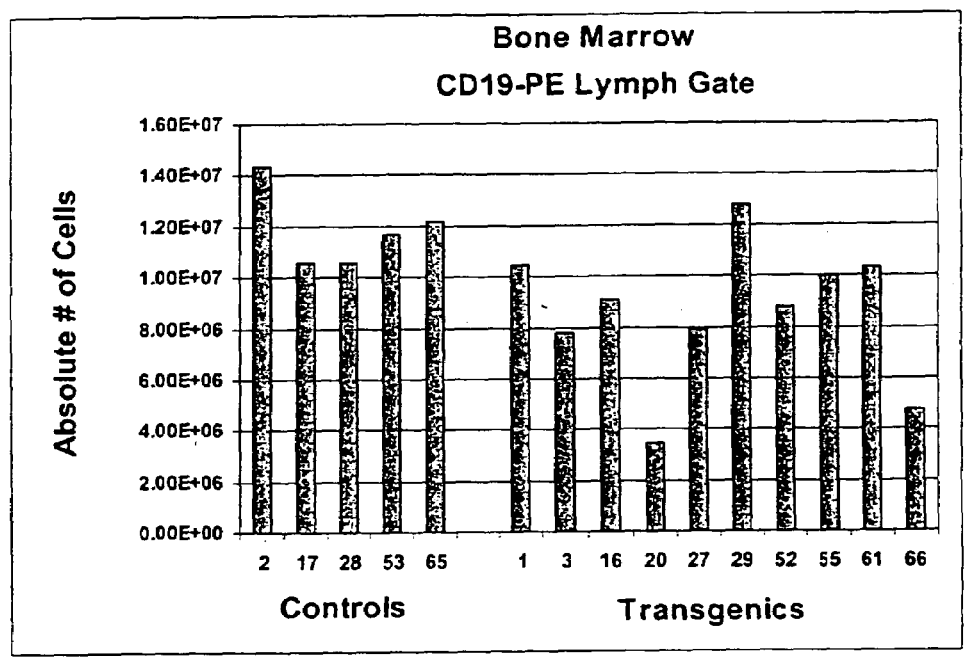
FIG. 14 depicts a bar chart histogram showing a slight decrease in absolute numbers of CD19+ B lymphocytes in the bone marrow of IL-17 like transgenic mice as compared to the non-transgenic littermate controls.
Figure 15:
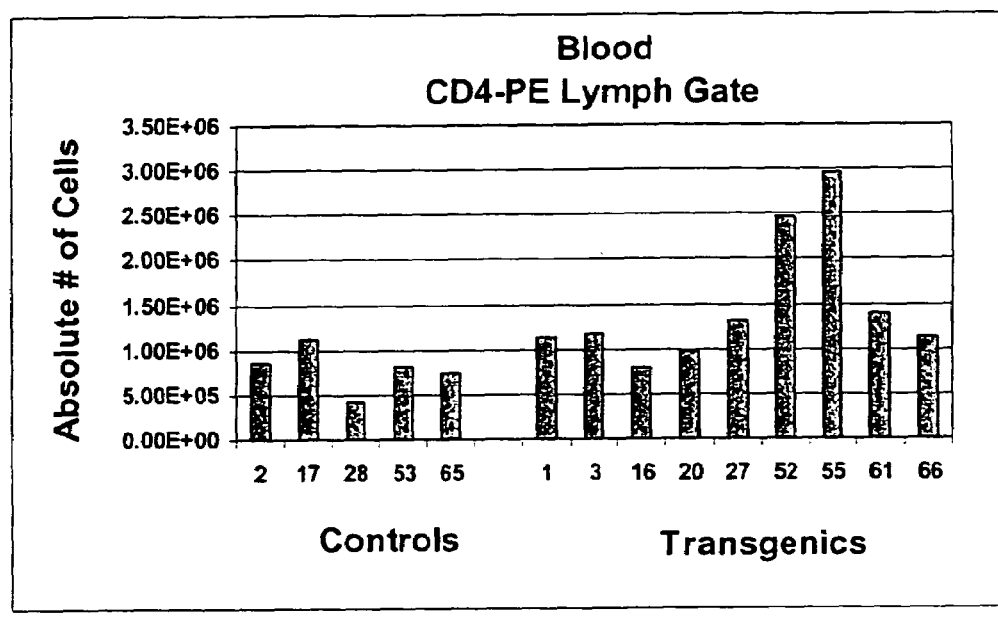
FIG. 15 depicts a bar chart histogram showing an increase in absolute numbers of CD4+ T lymphocytes in the peripheral blood of 4 out 9 IL-17 like transgenic mice as compared to the non-transgenic littermate controls.
Figure 16:
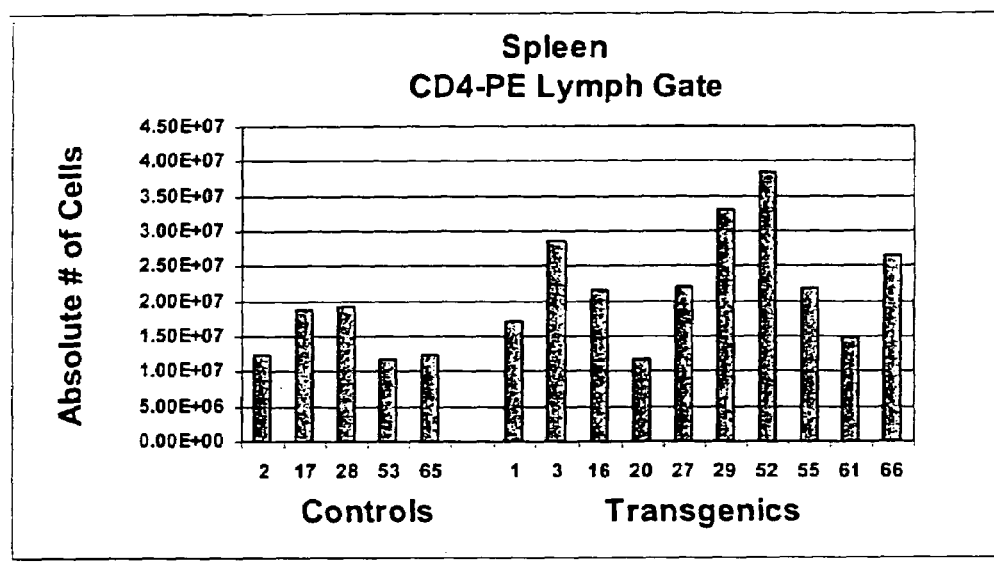
FIG. 16 depicts a bar chart histogram showing an increase in absolute numbers of CD4+ T lymphocytes in the spleens of IL-17 like transgenic mice as compared to the non-transgenic littermate controls.

In the 5 transgenic mice which exhibited a phenotype (nos. 29, 52, 55, 61 and 66), there was a striking increase in CD19+ cells (B cells) in the peripheral blood. As shown in FIG. 12, the absolute number of CD19+ cells was increased up to 5 fold compared to controls. In addition, there was a 2-4 fold increase in absolute number of CD19+ cells in the spleen as shown in FIG. 13. In the femoral bone marrow, there was a slight decrease in CD19+ cells (FIG. 14). Staining for CD45r followed a similar trend. The peripheral blood and spleens isolated from the transgenic mice also exhibited a 2-3 fold increase in the absolute number of helper T cells (CD4+ T lymphocytes). (See FIGS. 15 and 16; respectively)

Figure 17:
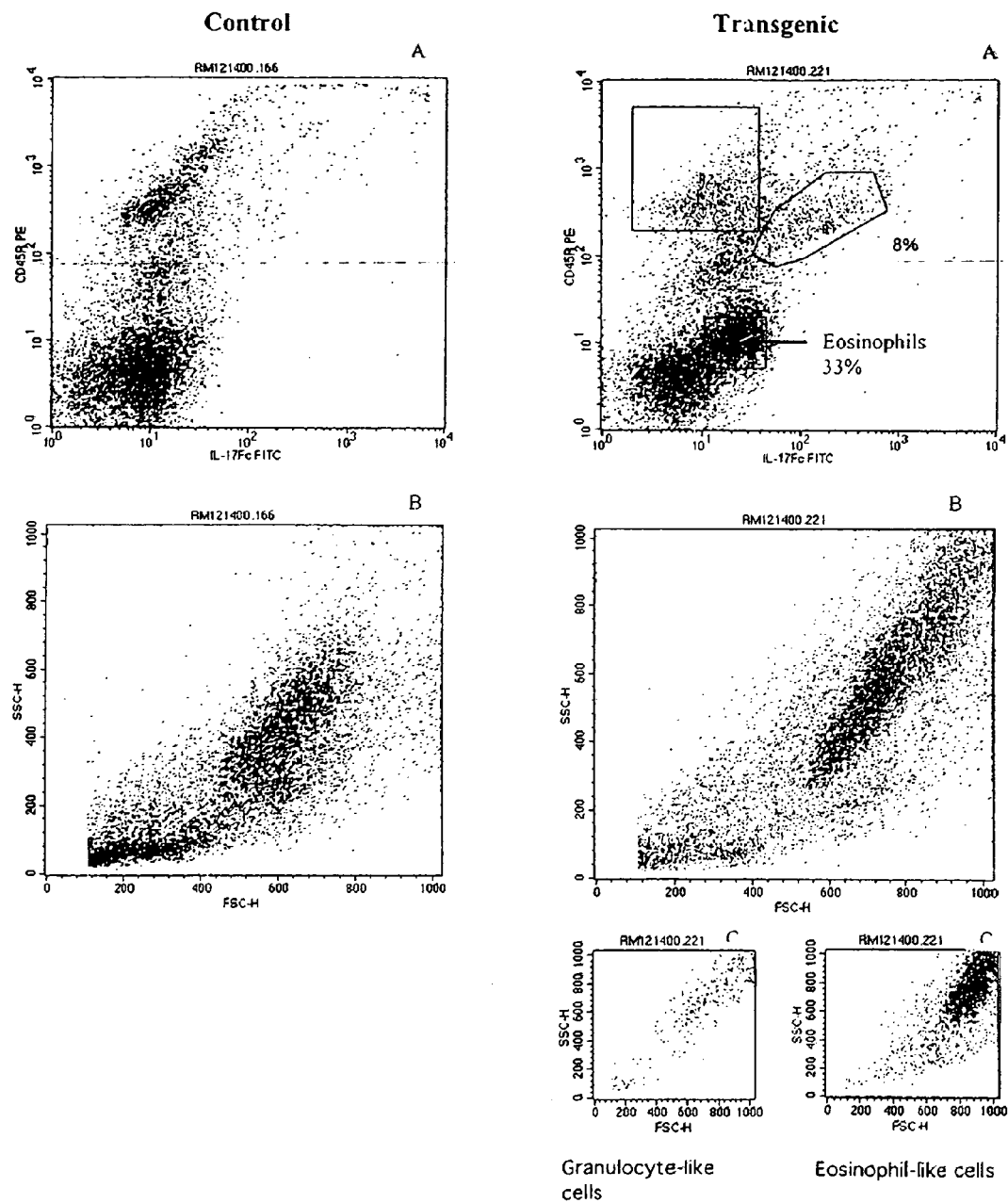
FIG. 17 depicts scatter plots representative of the changes occurring in the IL-17 like transgenic mice vs. their non-transgenic littermate controls. The two top plots labeled "A" are 2-color flow cytometric dot plots where CD45R+ and IL-17 like-Fc labeling are being depicted on their respective axes. Control plot "A" shows an absence of CD45R+/IL-17 like-Fc+ cells in the region R1 whereas in the transgenic plot "A", this population was present in region R1 and represented 8% of the total granulocyte population. In the corresponding Forward vs. Side scatter plot ("B" and "C") these cells are depicted as pink colored dots. This population was absent in the control plot "B".
Figure 18:
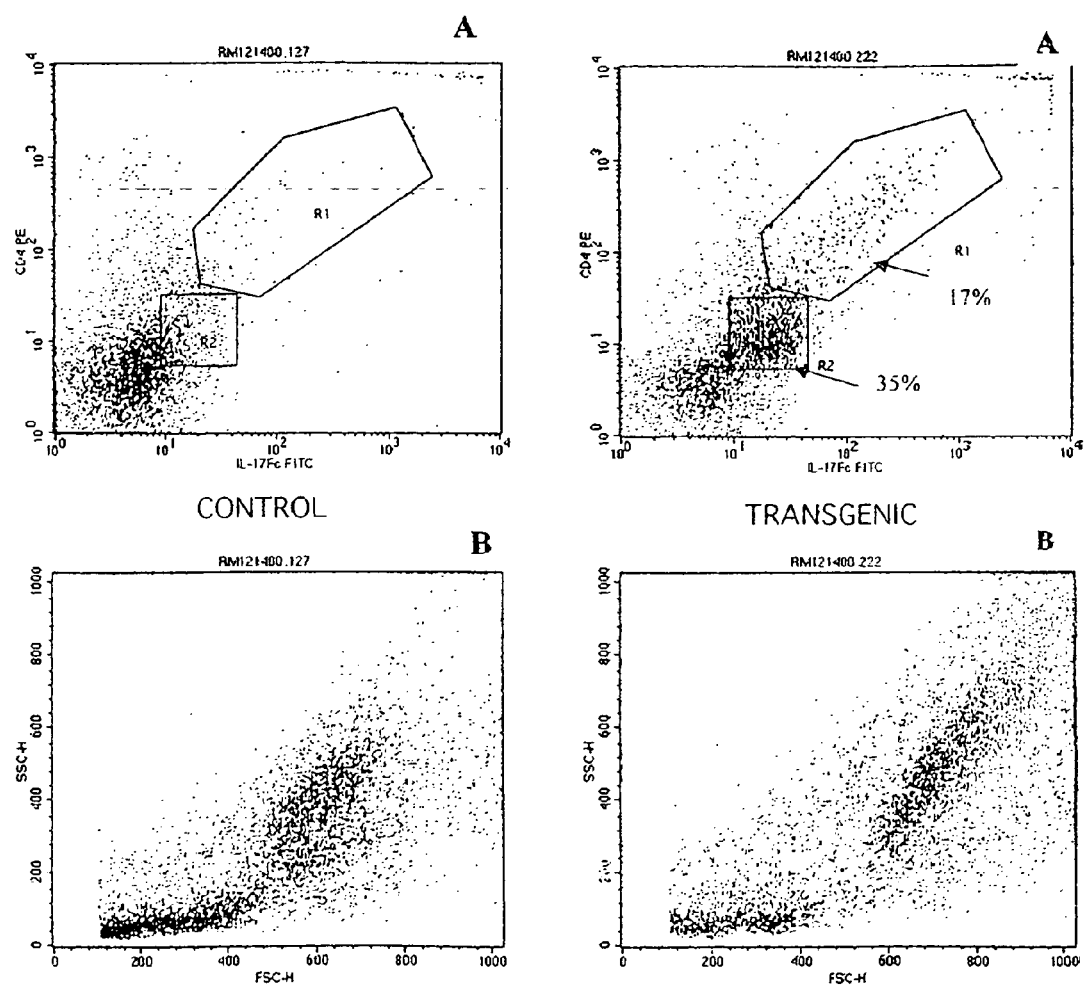
FIG. 18 depicts scatter plots representative of the changes occurring in the IL-17 like transgenic mice vs. their non-transgenic littermate controls. The two top plots labeled "A" are 2-color flow cytometric dot plots where CD4 and IL-17 like-Fc labeling are being depicted on their respective axis. Control plot "A" shows an absence of CD4+/IL-17 like-Fc+ cells in the region R1, whereas in the transgenic plot "A", this population was present in region R1 and represented 14% of the total granulocyte population. In the corresponding Forward vs. Side scatter plots (size vs. granularity), the IL-17 like transgenic mice (B) these cells are located just above the region where granulocytes are typically found (red colored dots). These cells are absent in the control plot "B". Furthermore, for the transgenic mice (A), there is an emergence of a population of cells that was neither CD4+ nor IL-17 like-Fc+ (region R2) but that has the scatter properties of eosinophils, localizing to the left of the granulocytes in the Forward vs. Side scatter plot "B" (green colored dots). This population was absent in the control plot "B".
Figure 19:
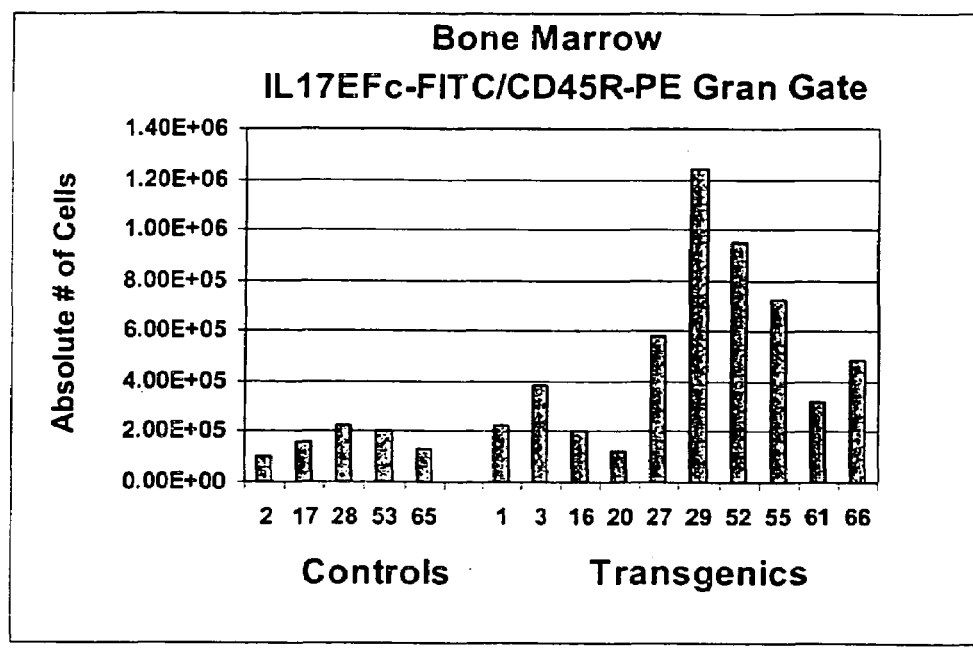
FIG. 19 depicts a bar chart histogram showing an increase in absolute numbers of rhIL-17 like-Fc+/CD45R+ granulocyte-like cells in the bone marrow of 5 out of 10 IL-17 like transgenic mice as compared to the non-transgenic littermate controls.
Figure 20:
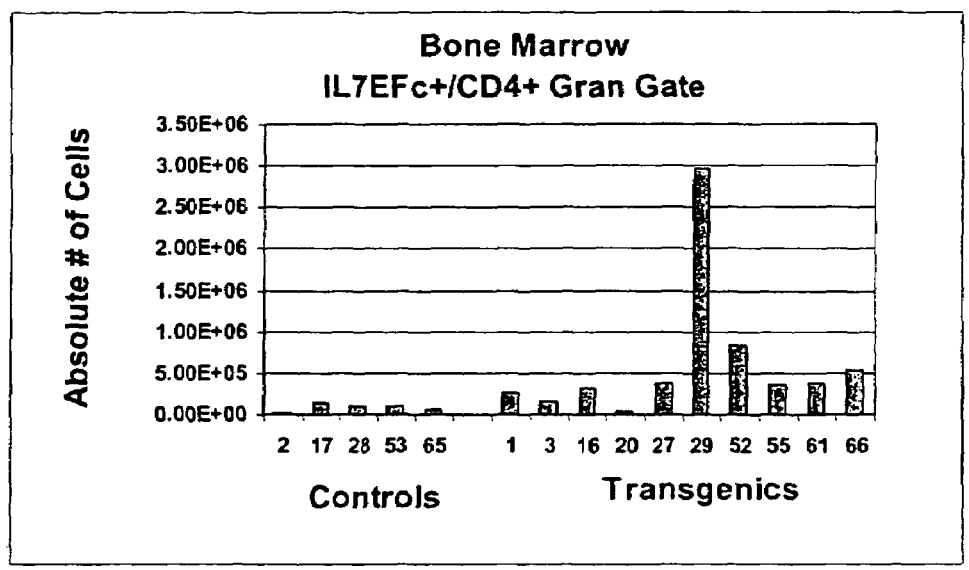
FIG. 20 depicts a bar chart histogram showing an increase in absolute numbers of rhIL-17 like-Fc+/CD4+ granulocyte-like cells in the bone marrow of IL-17 like transgenic mice as compared to the non-transgenic littermate controls.

The transgenic mice had a consistent appearance of a large population of cells (e.g., 33% granulocytes) bearing light scatter properties similar to those of eosinophils (FIGS. 17 and 18). In addition, the cells do not express the granulocytic marker. There was also a consistant appearance of a smaller but distinct population of granulocyte like cells (e.g., 8–17% of granulocytes) that express the IL-17 receptor like polypeptides in blood and bone marrow. (See FIGS. 19 and 20). Based on correlations with scatter plots, the transgenic mice seem to have the following multi-lineage phenotype: CD4+, CD45R+, CD11c+, and are large and granular.

Figure 21:
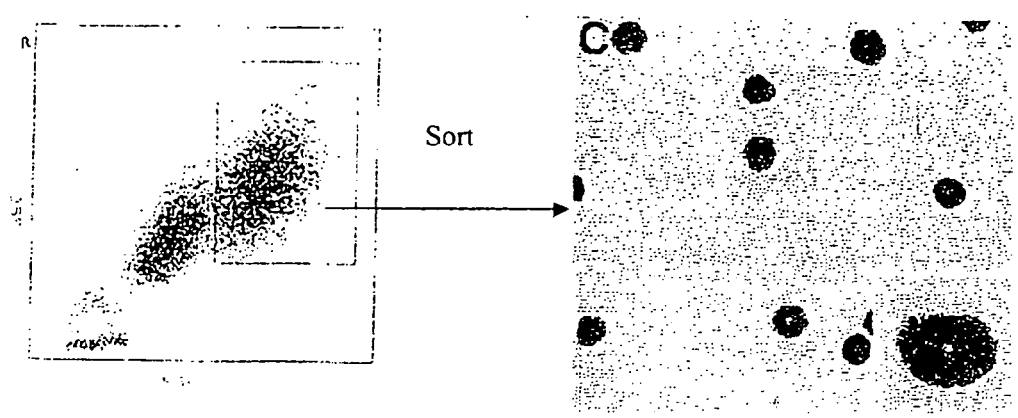
FIG. 21 depicts an example of a typical Forward vs. Side scatter plot (size vs. granularity). Cells in the gate can be sorted to give a purified population.

This analysis indicated that within the transgenic mice there was a clear emergence of an eosinophil-like population in the femoral bone marrow and peripheral blood. As shown in FIG. 21, the scatter profile of these cells closely resembles a "text-book" example of the forward vs. side scatter (size vs. granularity) properties of eosinophils.

There was also an important increase in the absolute number (and compartmental percentage) of circulating and splenic CD19+ B cells. Although the CD19+ lymphocytes were not positive for the activation marker CD69+, their increase in absolute number in the periphery and slight decrease in the bone marrow is suggestive of migration to peripheral tissues where proliferation is taking place.

The appearance of a multi-lineage phenotype in blood and bone marrow is suggestive of a lymphoma like phenotype. Furthermore, since the IL-17 receptor like polypeptides (SEQ ID NOS: 2 and 5) seems to be upregulated on these cells, it is suggestive that this population may be reactive to the omnipresence of IL-17 like protein. Together with the fact that there is clear eosinophilia in these mice, the multi-lineage phenotype closely fits the description of an acute myelomonocytic leukemia (M4 AML) (Campena & Behm, *J. Immunol. Meth.* 234,:59–75, 2000).

EXAMPLE 14

Northern Blot Analysis of IL-17 Receptor Like RNA

Northern blot analysis was carried out to determine which cell lines expressed the IL-17 receptor like RNA. Total RNA was isolated form 17 cell lines using the RNeasy Mini Kit (cat. No. 74104, Qiagen, Valencia, Calif.). The probe was generated by PCR using the following primers(primer 2445-34: CATTTTCCTACATCGGCTTCCCTG; SEQ ID NO: 26; and primer 2429-61 TGAATCTGGCT-TCTTTCACTGC; SEQ ID NO: 27). The probe was labeled with $^{32}$P-dCTP (cat. No. AA0005; Amersham Pharmacia Biotech) using Rediprime II Kit (cat. No. RPN 1633; Amersham Pharmacia Biotech). The Northern Blot analysis was performed with the Northern Max-Gly Kit (cat no. 1946, Ambion).

The following human, mouse and rabbit cell lines were tested and the level of expression of IL-17 receptor like RNA is indicated.

| Human Cell Lines: | Level of Expression |
|---|---|
| GM3104A (B-lymphoblast cell) | +++ |
| CCRF-SB (B-lymphoblast cell) | +++ |
| CESS (Lymphoma) | + |
| THP-1 (Acute monocytic leukemia) | +/− |
| DAMI (Megakaryocytes) | +/− |
| H-9 (T-cell lymphoma) | − |
| CCRF CEM (T-lymphoblast cell) | − |
| MOLT 4 (T-cell lymphocytes) | − |
| Hs 67 (Thymus, normal) | − |
| Jurkat E6-1 (T-cell leukemia) | − |
| J 45.01 (T-cell leukemia) | − |
| BW5147.3 (T-cell lymphoma) | − |
| CCRF HSB2 (T-lymphoblast cell) | − |
| AML 193(s) (Acute monocytic leukemia) | − |
| Animal cell lines: | |
| HIG-82 (Rabbit synoviocyte) | − |
| C 1498 (Mouse lymphoma) | − |
| A 20 (Mouse B cell lymphoma) | − |

What is claimed is:

1. An isolated nucleic acid molecule comprising a nucleotide sequence selected from the group consisting of:
   (a) the nucleotide sequence comprising nucleotides 50 through 1729 of SEQ ID NO: 4;
   (b) the nucleotide sequence comprising nucleotides 50 through 1099 of SEQ ID NO: 4;
   (c) the nucleotide sequence comprising nucleotides 89 through 1099 of SEQ ID NO: 4;
   (d) the nucleotide sequence encoding the polypeptide comprising amino acids 1 through 560 of SEQ ID NO: 5;
   (e) the nucleotide sequence encoding the polypeptide comprising amino acids 1 through 350 of SEQ ID NO: 5;
   (f) the nucleotide sequence encoding the polypeptide comprising amino acids 14 through 350 of SEQ ID NO: 5;
   (g) the nucleotide sequence encoding the polypeptide having an amino acid sequence that is at least 90 percent identical to amino acids 14 through 350 of SEQ ID NO: 5, wherein the polypeptide binds IL-17; and
   (h) the nucleotide sequence fully complementary to any of (a)–(g).

2. A vector comprising the nucleic acid molecule of claim 1.

3. An isolated host cell comprising the nucleic acid molecule of claim 1.

4. An isolated host cell comprising the nucleic acid molecule of claim 1 operatively linked to regulatory sequence other than the promoter for a native IL-17 receptor like polypeptide.

5. The host cell of claim 3 that is a eukaryotic cell.

6. The host cell of claim 3 that is a prokaryotic cell.

7. A process of producing an IL-17 receptor like polypeptide comprising culturing the host cell of claim 3 under suitable conditions to express the polypeptide, and optionally isolating the polypeptide from the culture.

8. A process of producing an IL-17 receptor like polypeptide comprising culturing the host cell of claim 4 under suitable conditions to express the polypeptide, and optionally isolating the polypeptide from the culture.

9. A composition comprising the nucleic acid molecule of claim 1 and a pharmaceutically acceptable formulation agent.

10. The composition the of claim 9, wherein said nucleic acid molecule is contained in a viral vector.

11. A viral vector comprising the nucleic acid molecules of claim 1.

12. The isolated nucleic acid molecule of claim 1 wherein the nucleic acid molecule encodes a polypeptide that induces inflammation.

13. The isolated nucleic acid molecule of claim 1 wherein the nucleic acid molecule encodes a polypeptide that induces myelopiesis.

14. An isolated host cell modified by transformation or transfection with a regulatory nucleic acid, wherein said regulatory nucleic acid is operatively linked to the nucleic acid comprising the nucleotide of SEQ ID NO:4.

15. The host cell of claim 14 wherein the regulatory nucleic acid sequence is a promoter.

16. The host cell of claim 14 wherein the regulatory nucleic acid is a transcription factor.

17. A process of producing an IL-17 receptor like polypeptide comprising culturing the host cell of claim 14 under suitable conditions to express the polypeptide, and optionally isolating the polypeptide from the culture.

18. The process of any one of claims 7, 8 and 17 wherein the nucleic acid molecule comprises promoter DNA other than the promoter DNA for the native IL-17 receptor like polypeptide operatively linked to the DNA encoding the IL-17 receptor like polypeptide.

19. A diagnostic reagent comprising a detectably labeled polynucleotide, wherein the polynucleotide encodes a polypeptide comprising the amino acid sequence selected from the group consisting of:

(a) amino acids 1 through 560 of SEQ ID NO: 5, (b) amino acids 1 through 350 of SEQ ID NO: 5, and (c) amino acids 14 through 350 of SEQ ID NO: 5.

20. The diagnostic reagent of claim 19, wherein said labeled polynucleotide is a first-strand cDNA.

21. An isolated nucleic acid molecule comprising the nucleotide sequence of the cDNA clone contained in ATCC deposit number PTA-3176.

22. An isolated nucleic acid molecule comprising a nucleotide sequence, wherein the nucleotide sequence encodes a polypeptide comprising the extracellular domain of the amino acid sequence encoded by the cDNA clone contained in ATCC deposit number PTA-3177.

23. An isolated nucleic acid molecule comprising the nucleotide sequence of the cDNA clone contained in ATCC deposit number PTA-3178.

24. An isolated nucleic acid molecule comprising a nucleotide sequence encoding a polypeptide having an amino acid sequence that is at least 90 percent identical to amino acids 14 through 350 of SEQ ID NO: 5, wherein the polypeptide binds IL-17.

25. The isolated nucleic acid molecule comprising a nucleotide sequence encoding the polypeptide comprising amino acids 14 through 350 of SEQ ID NO: 5.

26. An isolated nucleic acid molecule comprising the nucleotide sequence comprising nucleotides 89 through 1099 of SEQ ID NO: 4.

* * * * *

UNITED STATES PATENT AND TRADEMARK OFFICE
CERTIFICATE OF CORRECTION

PATENT NO.        : 7,094,566 B2                                              Page 1 of 1
APPLICATION NO.   : 09/810927
DATED             : August 22, 2006
INVENTOR(S)       : Eugene Medlock et al.

It is certified that error appears in the above-identified patent and that said Letters Patent is hereby corrected as shown below:

At Column 123, line 20, "composition the of" should be -- composition of --.

At Column 123, line 22, "molecules" should be -- molecule --.

At Column 123, line 29, "myelopiesis" should be -- myelopoiesis --.

Signed and Sealed this

Twenty-fifth Day of December, 2007

JON W. DUDAS
*Director of the United States Patent and Trademark Office*

SEQUENCE LISTING

```
<160> NUMBER OF SEQ ID NOS: 27

<210> SEQ ID NO 1
<211> LENGTH: 1841
<212> TYPE: DNA
<213> ORGANISM: Homo sapiens
<220> FEATURE:
<221> NAME/KEY: CDS
<222> LOCATION: (50)..(1555)

<400> SEQUENCE: 1
ataaaagcgc agcgtgcggg tggcctggat cccgcgcagt ggcccggcg atg tcg ctc      58
                                                     Met Ser Leu
                                                       1 gtg ctg cta agc ctg gcc gcg ctg tgc agg agc gcc gta ccc cga gag     106
Val Leu Leu Ser Leu Ala Ala Leu Cys Arg Ser Ala Val Pro Arg Glu
        5                  10                  15 ccg acc gtt caa tgt ggc tct gaa act ggg cca tct cca gag tgg atg     154
Pro Thr Val Gln Cys Gly Ser Glu Thr Gly Pro Ser Pro Glu Trp Met
 20                  25                  30                  35 cta caa cat gat cta atc ccc gga gac ttg agg gac ctc cga gta gaa     202
Leu Gln His Asp Leu Ile Pro Gly Asp Leu Arg Asp Leu Arg Val Glu
                40                  45                  50 cct gtt aca act agt gtt gca aca ggg gac tat tca att ttg atg aat     250
Pro Val Thr Thr Ser Val Ala Thr Gly Asp Tyr Ser Ile Leu Met Asn
            55                  60                  65 gta agc tgg gta ctc cgg gca gat gcc agc atc cgc ttg ttg aag gcc     298
Val Ser Trp Val Leu Arg Ala Asp Ala Ser Ile Arg Leu Leu Lys Ala
        70                  75                  80
```

-continued

| | |
|---|---|
| acc aag att tgt gtg acg ggc aaa agc aac ttc cag tcc tac agc tgt<br>Thr Lys Ile Cys Val Thr Gly Lys Ser Asn Phe Gln Ser Tyr Ser Cys<br>85                       90                       95 | 346 |
| gtg agg tgc aat tac aca gag gcc ttc cag act cag acc aga ccc tct<br>Val Arg Cys Asn Tyr Thr Glu Ala Phe Gln Thr Gln Thr Arg Pro Ser<br>100                   105                   110              115 | 394 |
| ggt ggt aaa tgg aca ttt tcc tac atc ggc ttc cct gta gag ctg aac<br>Gly Gly Lys Trp Thr Phe Ser Tyr Ile Gly Phe Pro Val Glu Leu Asn<br>                120                   125                  130 | 442 |
| aca gtc tat ttc att ggg gcc cat aat att cct aat gca aat atg aat<br>Thr Val Tyr Phe Ile Gly Ala His Asn Ile Pro Asn Ala Asn Met Asn<br>           135                   140                 145 | 490 |
| gaa gat ggc cct tcc atg tct gtg aat ttc acc tca cca ggc tgc cta<br>Glu Asp Gly Pro Ser Met Ser Val Asn Phe Thr Ser Pro Gly Cys Leu<br>              150                   155               160 | 538 |
| gac cac ata atg aaa tat aaa aaa aag tgt gtc aag gcc gga agc ctg<br>Asp His Ile Met Lys Tyr Lys Lys Lys Cys Val Lys Ala Gly Ser Leu<br>165                       170                   175 | 586 |
| tgg gat ccg aac atc act gct tgt aag aag aat gag gag aca gta gaa<br>Trp Asp Pro Asn Ile Thr Ala Cys Lys Lys Asn Glu Glu Thr Val Glu<br>180                       185                   190             195 | 634 |
| gtg aac ttc aca acc act ccc ctg gga aac aga tac atg gct ctt atc<br>Val Asn Phe Thr Thr Thr Pro Leu Gly Asn Arg Tyr Met Ala Leu Ile<br>                    200                   205                  210 | 682 |
| caa cac agc act atc atc ggg ttt tct cag gtg ttt gag cca cac cag<br>Gln His Ser Thr Ile Ile Gly Phe Ser Gln Val Phe Glu Pro His Gln<br>           215                   220                 225 | 730 |
| aag aaa caa acg cga gct tca gtg gtg att cca gtg act ggg gat agt<br>Lys Lys Gln Thr Arg Ala Ser Val Val Ile Pro Val Thr Gly Asp Ser<br>                230                   235                 240 | 778 |
| gaa ggt gct acg gtg cag ctg act cca tat ttt cct act tgt ggc agc<br>Glu Gly Ala Thr Val Gln Leu Thr Pro Tyr Phe Pro Thr Cys Gly Ser<br>245                       250                   255 | 826 |
| gac tgc atc cga cat aaa gga aca gtt gtg ctc tgc cca caa aca ggc<br>Asp Cys Ile Arg His Lys Gly Thr Val Val Leu Cys Pro Gln Thr Gly<br>260                       265                   270             275 | 874 |
| gtc cct ttc cct ctg gat aac aac aaa agc aag ccg gga ggc tgg ctg<br>Val Pro Phe Pro Leu Asp Asn Asn Lys Ser Lys Pro Gly Gly Trp Leu<br>                    280                   285                  290 | 922 |
| cct ctc ctc ctg ctg tct ctg ctg gtg gcc aca tgg gtg ctg gtg gca<br>Pro Leu Leu Leu Leu Ser Leu Leu Val Ala Thr Trp Val Leu Val Ala<br>           295                   300                 305 | 970 |
| ggg atc tat cta atg tgg agg cac gaa agg atc aag aag act tcc ttt<br>Gly Ile Tyr Leu Met Trp Arg His Glu Arg Ile Lys Lys Thr Ser Phe<br>           310                   315                 320 | 1018 |
| tct acc acc aca cta ctg ccc ccc att aag gtt ctt gtg gtt tac cca<br>Ser Thr Thr Thr Leu Leu Pro Pro Ile Lys Val Leu Val Val Tyr Pro<br>325                       330                   335 | 1066 |
| tct gaa ata tgt ttc cat cac aca att tgt tac ttc act gaa ttt ctt<br>Ser Glu Ile Cys Phe His His Thr Ile Cys Tyr Phe Thr Glu Phe Leu<br>340                       345                   350             355 | 1114 |
| caa aac cat tgc aga agt gag gtc atc ctc gaa aag tgg cag aaa aag<br>Gln Asn His Cys Arg Ser Glu Val Ile Leu Glu Lys Trp Gln Lys Lys<br>                    360                   365                  370 | 1162 |
| aaa ata gca gag atg ggt cca gtg cag tgg ctt gcc act caa aag aag<br>Lys Ile Ala Glu Met Gly Pro Val Gln Trp Leu Ala Thr Gln Lys Lys<br>           375                   380                 385 | 1210 |
| gca gca gac aaa gtc gtc ttc ctt ctt tcc aat gac gtc aac agt gtg<br>Ala Ala Asp Lys Val Val Phe Leu Leu Ser Asn Asp Val Asn Ser Val | 1258 |

-continued

```
                390                 395                 400
tgc gat ggt acc tgt ggc aag agc gag ggc agt ccc agt gag aac tct     1306
Cys Asp Gly Thr Cys Gly Lys Ser Glu Gly Ser Pro Ser Glu Asn Ser
        405                 410                 415 caa gac ctc ttc ccc ctt gcc ttt aac ctt ttc tgc agt gat cta aga     1354
Gln Asp Leu Phe Pro Leu Ala Phe Asn Leu Phe Cys Ser Asp Leu Arg
420                 425                 430                 435 agc cag att cat ctg cac aaa tac gtg gtg gtc tac ttt aga gag att     1402
Ser Gln Ile His Leu His Lys Tyr Val Val Val Tyr Phe Arg Glu Ile
                440                 445                 450 gat aca aaa gac gat tac aat gct ctc agt gtc tgc ccc aag tac cac     1450
Asp Thr Lys Asp Asp Tyr Asn Ala Leu Ser Val Cys Pro Lys Tyr His
            455                 460                 465 ctc atg aag gat gcc act gct ttc tgt gca gaa ctt ctc cat gtc aag     1498
Leu Met Lys Asp Ala Thr Ala Phe Cys Ala Glu Leu Leu His Val Lys
        470                 475                 480 cag cag gtg tca gca gga aaa aga tca caa gcc tgc cac gat ggc tgc     1546
Gln Gln Val Ser Ala Gly Lys Arg Ser Gln Ala Cys His Asp Gly Cys
    485                 490                 495 tgc tcc ttg tagcccaccc atgagaagca agagacctta aaggcttcct             1595
Cys Ser Leu
500 atcccaccaa ttacagggaa aaaacgtgtg atgatcctga agcttactat gcagcctaca   1655 aacagcctta gtaattaaaa cattttatac caataaaatt ttcaaatatt gctaactaat   1715 gtagcattaa ctaacgattg gaaactacat ttacaacttc aaagctgttt tatacataga   1775 aatcaattac agctttaatt gaaaactgta accattttga taatgcaaca ataaagcatc   1835 ttcagc                                                              1841
```

<210> SEQ ID NO 2
<211> LENGTH: 502
<212> TYPE: PRT
<213> ORGANISM: Homo sapiens

<400> SEQUENCE: 2

```
Met Ser Leu Val Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Lys Cys Val Lys Ala
```

```
                    165                 170                 175
Gly Ser Leu Trp Asp Pro Asn Ile Thr Ala Cys Lys Lys Asn Glu Glu
                180                 185                 190

Thr Val Glu Val Asn Phe Thr Thr Thr Pro Leu Gly Asn Arg Tyr Met
            195                 200                 205

Ala Leu Ile Gln His Ser Thr Ile Ile Gly Phe Ser Gln Val Phe Glu
        210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
                260                 265                 270

Gln Thr Gly Val Pro Phe Pro Leu Asp Asn Asn Lys Ser Lys Pro Gly
            275                 280                 285

Gly Trp Leu Pro Leu Leu Leu Ser Leu Leu Val Ala Thr Trp Val
        290                 295                 300

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
                325                 330                 335

Val Tyr Pro Ser Glu Ile Cys Phe His His Thr Ile Cys Tyr Phe Thr
                340                 345                 350

Glu Phe Leu Gln Asn His Cys Arg Ser Glu Val Ile Leu Glu Lys Trp
            355                 360                 365

Gln Lys Lys Lys Ile Ala Glu Met Gly Pro Val Gln Trp Leu Ala Thr
        370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
                405                 410                 415

Glu Asn Ser Gln Asp Leu Phe Pro Leu Ala Phe Asn Leu Phe Cys Ser
                420                 425                 430

Asp Leu Arg Ser Gln Ile His Leu His Lys Tyr Val Val Tyr Phe
            435                 440                 445

Arg Glu Ile Asp Thr Lys Asp Tyr Asn Ala Leu Ser Val Cys Pro
        450                 455                 460

Lys Tyr His Leu Met Lys Asp Ala Thr Ala Phe Cys Ala Glu Leu Leu
465                 470                 475                 480

His Val Lys Gln Gln Val Ser Ala Gly Lys Arg Ser Gln Ala Cys His
                485                 490                 495

Asp Gly Cys Cys Ser Leu
                500

<210> SEQ ID NO 3
<211> LENGTH: 539
<212> TYPE: PRT
<213> ORGANISM: Homo sapiens

<400> SEQUENCE: 3

Met Gly Ala Ala Arg Ser Pro Pro Ser Ala Val Pro Gly Pro Leu Leu
  1               5                  10                  15

Gly Leu Leu Leu Leu Leu Leu Gly Val Leu Ala Pro Gly Gly Ala Ser
             20                  25                  30
```

-continued

Leu Arg Leu Leu Asp His Arg Ala Leu Val Cys Ser Gln Pro Gly Leu
         35                  40                  45

Asn Cys Thr Val Lys Asn Ser Thr Cys Leu Asp Asp Ser Trp Ile His
 50                  55                  60

Pro Arg Asn Leu Thr Pro Ser Ser Pro Lys Asp Leu Gln Ile Gln Leu
 65                  70                  75                  80

His Phe Ala His Thr Gln Gln Gly Asp Leu Phe Pro Val Ala His Ile
                 85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Thr
        130                 135                 140

Pro Cys Met Ser Ser Gly Ser Leu Trp Asp Pro Asn Ile Thr Val Glu
145                 150                 155                 160

Thr Leu Glu Ala His Gln Leu Arg Val Ser Phe Thr Leu Trp Asn Glu
                165                 170                 175

Ser Thr His Tyr Gln Ile Leu Leu Thr Ser Phe Pro His Met Glu Asn
            180                 185                 190

His Ser Cys Phe Glu His Met His His Ile Pro Ala Pro Arg Pro Glu
        195                 200                 205

Glu Phe His Gln Arg Ser Asn Val Thr Leu Thr Leu Arg Asn Leu Lys
    210                 215                 220

Gly Cys Cys Arg His Gln Val Gln Ile Gln Pro Phe Phe Ser Ser Cys
225                 230                 235                 240

Leu Asn Asp Cys Leu Arg His Ser Ala Thr Val Ser Cys Pro Glu Met
                245                 250                 255

Pro Asp Thr Pro Glu Pro Ile Pro Asp Tyr Met Pro Leu Trp Val Tyr
                260                 265                 270

Trp Phe Ile Thr Gly Ile Ser Ile Leu Leu Val Gly Ser Val Ile Leu
        275                 280                 285

Leu Ile Val Cys Met Thr Trp Arg Leu Ala Gly Pro Gly Ser Glu Lys
    290                 295                 300

Tyr Ser Asp Asp Thr Lys Tyr Thr Asp Gly Leu Pro Ala Ala Asp Leu
305                 310                 315                 320

Ile Pro Pro Pro Leu Lys Pro Arg Lys Val Trp Ile Ile Tyr Ser Ala
                325                 330                 335

Asp His Pro Leu Tyr Val Asp Val Val Leu Lys Phe Ala Gln Phe Leu
                340                 345                 350

Leu Thr Ala Cys Gly Thr Glu Val Ala Leu Asp Leu Leu Glu Glu Gln
        355                 360                 365

Ala Ile Ser Glu Ala Gly Val Met Thr Trp Val Gly Arg Gln Lys Gln
    370                 375                 380

Glu Met Val Glu Ser Asn Ser Lys Ile Ile Val Leu Cys Ser Arg Gly
385                 390                 395                 400

Thr Arg Ala Lys Trp Gln Ala Leu Leu Gly Arg Gly Ala Pro Val Arg
                405                 410                 415

Leu Arg Cys Asp His Gly Lys Pro Val Gly Asp Leu Phe Thr Ala Ala
                420                 425                 430

Met Asn Met Ile Leu Pro Asp Phe Lys Arg Pro Ala Cys Phe Gly Thr
        435                 440                 445

Tyr Val Val Cys Tyr Phe Ser Glu Val Ser Cys Asp Gly Asp Val Pro

```
        450              455              460
Asp Leu Phe Gly Ala Ala Pro Arg Tyr Pro Leu Met Asp Arg Phe Glu
465              470              475              480

Glu Val Tyr Phe Arg Ile Gln Asp Leu Glu Met Phe Gln Pro Gly Arg
            485              490              495

Met His Arg Val Gly Glu Leu Ser Gly Asp Asn Tyr Leu Arg Ser Pro
        500              505              510

Gly Gly Arg Gln Leu Arg Ala Ala Leu Asp Arg Phe Arg Asp Trp Gln
            515              520              525

Val Arg Cys Pro Asp Trp Phe Glu Cys Glu Asn
        530              535

<210> SEQ ID NO 4
<211> LENGTH: 2015
<212> TYPE: DNA
<213> ORGANISM: Homo sapiens
<220> FEATURE:
<221> NAME/KEY: CDS
<222> LOCATION: (50)..(1729)

<400> SEQUENCE: 4
ataaaagcgc agcgtgcggg tggcctggat cccgcgcagt ggcccggcg atg tcg ctc      58
                                                     Met Ser Leu
                                                       1 gtg ctg cta agc ctg gcc gcg ctg tgc agg agc gcc gta ccc cga gag     106
Val Leu Leu Ser Leu Ala Ala Leu Cys Arg Ser Ala Val Pro Arg Glu
     5                  10                  15 ccg acc gtt caa tgt ggc tct gaa act ggg cca tct cca gag tgg atg     154
Pro Thr Val Gln Cys Gly Ser Glu Thr Gly Pro Ser Pro Glu Trp Met
 20                  25                  30                  35 cta caa cat gat cta atc ccc gga gac ttg agg gac ctc cga gta gaa     202
Leu Gln His Asp Leu Ile Pro Gly Asp Leu Arg Asp Leu Arg Val Glu
                 40                  45                  50 cct gtt aca act agt gtt gca aca ggg gac tat tca att ttg atg aat     250
Pro Val Thr Thr Ser Val Ala Thr Gly Asp Tyr Ser Ile Leu Met Asn
             55                  60                  65 gta agc tgg gta ctc cgg gca gat gcc agc atc cgc ttg ttg aag gcc     298
Val Ser Trp Val Leu Arg Ala Asp Ala Ser Ile Arg Leu Leu Lys Ala
         70                  75                  80 acc aag att tgt gtg acg ggc aaa agc aac ttc cag tcc tac agc tgt     346
Thr Lys Ile Cys Val Thr Gly Lys Ser Asn Phe Gln Ser Tyr Ser Cys
     85                  90                  95 gtg agg ctg gag tgc agt ggt gcg atc atg gct cgc tgc gac ctc aat     394
Val Arg Leu Glu Cys Ser Gly Ala Ile Met Ala Arg Cys Asp Leu Asn
100                 105                 110                 115 ctt ctg ggc tca agc gat cgt tct gct tca gcc tcc cga gcg gct ggg     442
Leu Leu Gly Ser Ser Asp Arg Ser Ala Ser Ala Ser Arg Ala Ala Gly
                 120                 125                 130 act gca ggc gtg ggc cac cag acc tgg cta att ttt gta gtt ttt gta     490
Thr Ala Gly Val Gly His Gln Thr Trp Leu Ile Phe Val Val Phe Val
             135                 140                 145 gag ggg ggt ttc acc gtg ttg ctg gtc ttg aat tcc agt gct cag gcg     538
Glu Gly Gly Phe Thr Val Leu Leu Val Leu Asn Ser Ser Ala Gln Ala
         150                 155                 160 atc tgc ctg cct cgg ctt ccc aaa gtg ctg gga tta cag tgg aca ttt     586
Ile Cys Leu Pro Arg Leu Pro Lys Val Leu Gly Leu Gln Trp Thr Phe
     165                 170                 175 tcc tac atc ggc ttc cct gta gag ctg aac aca gtc tat ttc att ggg     634
Ser Tyr Ile Gly Phe Pro Val Glu Leu Asn Thr Val Tyr Phe Ile Gly
180                 185                 190                 195
```

-continued

| | |
|---|---|
| gcc cat aat att cct aat gca aat atg aat gaa gat ggc cct tcc atg<br>Ala His Asn Ile Pro Asn Ala Asn Met Asn Glu Asp Gly Pro Ser Met<br>                   200                          205                      210 | 682 |
| tct gtg aat ttc acc tca cca ggc tgc cta gac cac ata atg aaa tat<br>Ser Val Asn Phe Thr Ser Pro Gly Cys Leu Asp His Ile Met Lys Tyr<br>             215                          220                         225 | 730 |
| aaa aaa aag tgt gtc aag gcc gga agc ctg tgg gat ccg aac atc act<br>Lys Lys Lys Cys Val Lys Ala Gly Ser Leu Trp Asp Pro Asn Ile Thr<br>230                          235                         240 | 778 |
| gct tgt aag aag aat gag gag aca gta gaa gtg aac ttc aca acc act<br>Ala Cys Lys Lys Asn Glu Glu Thr Val Glu Val Asn Phe Thr Thr Thr<br>             245                          250                        255 | 826 |
| ccc ctg gga aac aga tac atg gct ctt atc caa cac agc act atc atc<br>Pro Leu Gly Asn Arg Tyr Met Ala Leu Ile Gln His Ser Thr Ile Ile<br>260                       265                       270                   275 | 874 |
| ggg ttt tct cag gtg ttt gag cca cac cag aag aaa caa acg cga gct<br>Gly Phe Ser Gln Val Phe Glu Pro His Gln Lys Lys Gln Thr Arg Ala<br>                   280                       285                      290 | 922 |
| tca gtg gtg att cca gtg act ggg gat agt gaa ggt gct acg gtg cag<br>Ser Val Val Ile Pro Val Thr Gly Asp Ser Glu Gly Ala Thr Val Gln<br>             295                          300                        305 | 970 |
| ctg act cca tat ttt cct act tgt ggc agc gac tgc atc cga cat aaa<br>Leu Thr Pro Tyr Phe Pro Thr Cys Gly Ser Asp Cys Ile Arg His Lys<br>                   310                       315                      320 | 1018 |
| gga aca gtt gtg ctc tgc cca caa aca ggc gtc cct ttc cct ctg gat<br>Gly Thr Val Val Leu Cys Pro Gln Thr Gly Val Pro Phe Pro Leu Asp<br>325                       330                       335 | 1066 |
| aac aac aaa agc aag ccg gga ggc tgg ctg cct ctc ctc ctg tct<br>Asn Asn Lys Ser Lys Pro Gly Gly Trp Leu Pro Leu Leu Leu Leu Ser<br>340                       345                       350                   355 | 1114 |
| ctg ctg gtg gcc aca tgg gtg ctg gtg gca ggg atc tat cta atg tgg<br>Leu Leu Val Ala Thr Trp Val Leu Val Ala Gly Ile Tyr Leu Met Trp<br>                   360                       365                      370 | 1162 |
| agg cac gaa agg atc aag aag act tcc ttt tct acc acc aca cta ctg<br>Arg His Glu Arg Ile Lys Lys Thr Ser Phe Ser Thr Thr Thr Leu Leu<br>             375                          380                        385 | 1210 |
| ccc ccc att aag gtt ctt gtg gtt tac cca tct gaa ata tgt ttc cat<br>Pro Pro Ile Lys Val Leu Val Val Tyr Pro Ser Glu Ile Cys Phe His<br>                   390                       395                      400 | 1258 |
| cac aca att tgt tac ttc act gaa ttt ctt caa aac cat tgc aga agt<br>His Thr Ile Cys Tyr Phe Thr Glu Phe Leu Gln Asn His Cys Arg Ser<br>405                       410                       415 | 1306 |
| gag gtc atc ctc gaa aag tgg cag aaa aag aaa ata gca gag atg ggt<br>Glu Val Ile Leu Glu Lys Trp Gln Lys Lys Lys Ile Ala Glu Met Gly<br>420                       425                       430                   435 | 1354 |
| cca gtg cag tgg ctt gcc act caa aag aag gca gca gac aaa gtc gtc<br>Pro Val Gln Trp Leu Ala Thr Gln Lys Lys Ala Ala Asp Lys Val Val<br>                   440                       445                      450 | 1402 |
| ttc ctt ctt tcc aat gac gtc aac agt gtg tgc gat ggt acc tgt ggc<br>Phe Leu Leu Ser Asn Asp Val Asn Ser Val Cys Asp Gly Thr Cys Gly<br>             455                          460                        465 | 1450 |
| aag agc gag ggc agt ccc agt gag aac tct caa gac ctc ttc ccc ctt<br>Lys Ser Glu Gly Ser Pro Ser Glu Asn Ser Gln Asp Leu Phe Pro Leu<br>                   470                       475                      480 | 1498 |
| gcc ttt aac ctt ttc tgc agt gat cta aga agc cag att cat ctg cac<br>Ala Phe Asn Leu Phe Cys Ser Asp Leu Arg Ser Gln Ile His Leu His<br>485                       490                       495 | 1546 |
| aaa tac gtg gtg gtc tac ttt aga gag att gat aca aaa gac gat tac<br>Lys Tyr Val Val Val Tyr Phe Arg Glu Ile Asp Thr Lys Asp Asp Tyr | 1594 |

```
                                             500                    505                   510                    515
aat gct ctc agt gtc tgc ccc aag tac cac ctc atg aag gat gcc act         1642
Asn Ala Leu Ser Val Cys Pro Lys Tyr His Leu Met Lys Asp Ala Thr
                520                     525                     530 gct ttc tgt gca gaa ctt ctc cat gtc aag cag cag gtg tca gca gga         1690
Ala Phe Cys Ala Glu Leu Leu His Val Lys Gln Gln Val Ser Ala Gly
                535                     540                     545 aaa aga tca caa gcc tgc cac gat ggc tgc tgc tcc ttg tagcccaccc          1739
Lys Arg Ser Gln Ala Cys His Asp Gly Cys Cys Ser Leu
                550                     555                 560 atgagaagca agagacctta aaggcttcct atcccaccaa ttacagggaa aaaacgtgtg       1799
atgatcctga agcttactat gcagcctaca aacagcctta gtaattaaaa cattttatac       1859
caataaaatt ttcaaatatt gctaactaat gtagcattaa ctaacgattg gaaactacat       1919
ttacaacttc aaagctgttt tatacataga aatcaattac agctttaatt gaaaactgta       1979
accattttga taatgcaaca ataaagcatc ttcagc                                 2015

<210> SEQ ID NO 5
<211> LENGTH: 560
<212> TYPE: PRT
<213> ORGANISM: Homo sapiens

<400> SEQUENCE: 5

Met Ser Leu Val Leu Leu Ser Leu Ala Ala Leu Cys Arg Ser Ala Val
  1               5                  10                  15

Pro Arg Glu Pro Thr Val Gln Cys Gly Ser Glu Thr Gly Pro Ser Pro
                 20                  25                  30

Glu Trp Met Leu Gln His Asp Leu Ile Pro Gly Asp Leu Arg Asp Leu
             35                  40                  45

Arg Val Glu Pro Val Thr Thr Ser Val Ala Thr Gly Asp Tyr Ser Ile
         50                  55                  60

Leu Met Asn Val Ser Trp Val Leu Arg Ala Asp Ala Ser Ile Arg Leu
 65                  70                  75                  80

Leu Lys Ala Thr Lys Ile Cys Val Thr Gly Lys Ser Asn Phe Gln Ser
                 85                  90                  95

Tyr Ser Cys Val Arg Leu Glu Cys Ser Gly Ala Ile Met Ala Arg Cys
                100                 105                 110

Asp Leu Asn Leu Leu Gly Ser Ser Asp Arg Ser Ala Ser Ala Ser Arg
            115                 120                 125

Ala Ala Gly Thr Ala Gly Val Gly His Gln Thr Trp Leu Ile Phe Val
        130                 135                 140

Val Phe Val Glu Gly Gly Phe Thr Val Leu Leu Val Leu Asn Ser Ser
145                 150                 155                 160

Ala Gln Ala Ile Cys Leu Pro Arg Leu Pro Lys Val Leu Gly Leu Gln
                165                 170                 175

Trp Thr Phe Ser Tyr Ile Gly Phe Pro Val Glu Leu Asn Thr Val Tyr
                180                 185                 190

Phe Ile Gly Ala His Asn Ile Pro Asn Ala Asn Met Asn Glu Asp Gly
            195                 200                 205

Pro Ser Met Ser Val Asn Phe Thr Ser Pro Gly Cys Leu Asp His Ile
        210                 215                 220

Met Lys Tyr Lys Lys Cys Val Lys Ala Gly Ser Leu Trp Asp Pro
225                 230                 235                 240

Asn Ile Thr Ala Cys Lys Lys Asn Glu Glu Thr Val Glu Val Asn Phe
                245                 250                 255
```

-continued

```
Thr Thr Thr Pro Leu Gly Asn Arg Tyr Met Ala Leu Ile Gln His Ser
            260                 265                 270
Thr Ile Ile Gly Phe Ser Gln Val Phe Glu Pro His Gln Lys Lys Gln
            275                 280                 285
Thr Arg Ala Ser Val Val Ile Pro Val Thr Gly Asp Ser Glu Gly Ala
            290                 295                 300
Thr Val Gln Leu Thr Pro Tyr Phe Pro Thr Cys Gly Ser Asp Cys Ile
305                 310                 315                 320
Arg His Lys Gly Thr Val Val Leu Cys Pro Gln Thr Gly Val Pro Phe
                325                 330                 335
Pro Leu Asp Asn Asn Lys Ser Lys Pro Gly Gly Trp Leu Pro Leu Leu
            340                 345                 350
Leu Leu Ser Leu Leu Val Ala Thr Trp Val Leu Val Ala Gly Ile Tyr
            355                 360                 365
Leu Met Trp Arg His Glu Arg Ile Lys Lys Thr Ser Phe Ser Thr Thr
            370                 375                 380
Thr Leu Leu Pro Pro Ile Lys Val Leu Val Val Tyr Pro Ser Glu Ile
385                 390                 395                 400
Cys Phe His His Thr Ile Cys Tyr Phe Thr Glu Phe Leu Gln Asn His
                405                 410                 415
Cys Arg Ser Glu Val Ile Leu Glu Lys Trp Gln Lys Lys Lys Ile Ala
            420                 425                 430
Glu Met Gly Pro Val Gln Trp Leu Ala Thr Gln Lys Lys Ala Ala Asp
            435                 440                 445
Lys Val Val Phe Leu Leu Ser Asn Asp Val Asn Ser Val Cys Asp Gly
450                 455                 460
Thr Cys Gly Lys Ser Glu Gly Ser Pro Ser Glu Asn Ser Gln Asp Leu
465                 470                 475                 480
Phe Pro Leu Ala Phe Asn Leu Phe Cys Ser Asp Leu Arg Ser Gln Ile
                485                 490                 495
His Leu His Lys Tyr Val Val Tyr Phe Arg Glu Ile Asp Thr Lys
            500                 505                 510
Asp Asp Tyr Asn Ala Leu Ser Val Cys Pro Lys Tyr His Leu Met Lys
            515                 520                 525
Asp Ala Thr Ala Phe Cys Ala Glu Leu Leu His Val Lys Gln Gln Val
            530                 535                 540
Ser Ala Gly Lys Arg Ser Gln Ala Cys His Asp Gly Cys Cys Ser Leu
545                 550                 555                 560
```

<210> SEQ ID NO 6
<211> LENGTH: 1713
<212> TYPE: DNA
<213> ORGANISM: Homo sapiens
<220> FEATURE:
<221> NAME/KEY: CDS
<222> LOCATION: (273)..(1427)

<400> SEQUENCE: 6

```
ataaaagcgc agcgtgcggg tggcctggat cccgcgcagt ggcccggcga tgtcgctcgt     60
gctgctaagc ctggccgcgc tgtgcaggag cgccgtaccc cgagagccga ccgttcaatg    120
tggctctgaa actgggccat ctccagagtg gatgctacaa catgatctaa tcccgggaga    180
cttgagggac ctccgagtag aacctgttac aactagtgtt gcaacagggg actattcaat    240
tttgatgaat gtaagctggg tactccgggc ag atg tgg aca ttt tcc tac atc     293
                                    Met Trp Thr Phe Ser Tyr Ile
```

-continued

|  |  |  |  | 1 |  |  |  | 5 |  |  |  |  |  |  |  |
|---|---|---|---|---|---|---|---|---|---|---|---|---|---|---|---|
| ggc | ttc | cct | gta | gag | ctg | aac | aca | gtc | tat | ttc | att | ggg | gcc | cat | aat | 341 |
| Gly | Phe | Pro | Val | Glu | Leu | Asn | Thr | Val | Tyr | Phe | Ile | Gly | Ala | His | Asn |
|  |  | 10 |  |  |  | 15 |  |  |  | 20 |

| att | cct | aat | gca | aat | atg | aat | gaa | gat | ggc | cct | tcc | atg | tct | gtg | aat | 389 |
| Ile | Pro | Asn | Ala | Asn | Met | Asn | Glu | Asp | Gly | Pro | Ser | Met | Ser | Val | Asn |
|  | 25 |  |  |  | 30 |  |  |  | 35 |

| ttc | acc | tca | cca | ggc | tgc | cta | gac | cac | ata | atg | aaa | tat | aaa | aaa | aag | 437 |
| Phe | Thr | Ser | Pro | Gly | Cys | Leu | Asp | His | Ile | Met | Lys | Tyr | Lys | Lys | Lys |
| 40 |  |  |  | 45 |  |  |  | 50 |  |  |  | 55 |

| tgt | gtc | aag | gcc | gga | agc | ctg | tgg | gat | ccg | aac | atc | act | gct | tgt | aag | 485 |
| Cys | Val | Lys | Ala | Gly | Ser | Leu | Trp | Asp | Pro | Asn | Ile | Thr | Ala | Cys | Lys |
|  |  |  | 60 |  |  |  | 65 |  |  |  | 70 |

| aag | aat | gag | gag | aca | gta | gaa | gtg | aac | ttc | aca | acc | act | ccc | ctg | gga | 533 |
| Lys | Asn | Glu | Glu | Thr | Val | Glu | Val | Asn | Phe | Thr | Thr | Thr | Pro | Leu | Gly |
|  |  | 75 |  |  |  | 80 |  |  |  | 85 |

| aac | aga | tac | atg | gct | ctt | atc | caa | cac | agc | act | atc | atc | ggg | ttt | tct | 581 |
| Asn | Arg | Tyr | Met | Ala | Leu | Ile | Gln | His | Ser | Thr | Ile | Ile | Gly | Phe | Ser |
|  |  | 90 |  |  |  | 95 |  |  |  | 100 |

| cag | gtg | ttt | gag | cca | cac | cag | aag | aaa | caa | acg | cga | gct | tca | gtg | gtg | 629 |
| Gln | Val | Phe | Glu | Pro | His | Gln | Lys | Lys | Gln | Thr | Arg | Ala | Ser | Val | Val |
|  | 105 |  |  |  | 110 |  |  |  | 115 |

| att | cca | gtg | act | ggg | gat | agt | gaa | ggt | gct | acg | gtg | cag | ctg | act | cca | 677 |
| Ile | Pro | Val | Thr | Gly | Asp | Ser | Glu | Gly | Ala | Thr | Val | Gln | Leu | Thr | Pro |
| 120 |  |  |  | 125 |  |  |  | 130 |  |  |  | 135 |

| tat | ttt | cct | act | tgt | ggc | agc | gac | tgc | atc | cga | cat | aaa | gga | aca | gtt | 725 |
| Tyr | Phe | Pro | Thr | Cys | Gly | Ser | Asp | Cys | Ile | Arg | His | Lys | Gly | Thr | Val |
|  |  |  | 140 |  |  |  | 145 |  |  |  | 150 |

| gtg | ctc | tgc | cca | caa | aca | ggc | gtc | cct | ttc | cct | ctg | gat | aac | aac | aaa | 773 |
| Val | Leu | Cys | Pro | Gln | Thr | Gly | Val | Pro | Phe | Pro | Leu | Asp | Asn | Asn | Lys |
|  |  | 155 |  |  |  | 160 |  |  |  | 165 |

| agc | aag | ccg | gga | ggc | tgg | ctg | cct | ctc | ctc | ctg | tct | ctg | ctg | gtg | 821 |
| Ser | Lys | Pro | Gly | Gly | Trp | Leu | Pro | Leu | Leu | Leu | Ser | Leu | Leu | Val |
|  |  | 170 |  |  |  | 175 |  |  |  | 180 |

| gcc | aca | tgg | gtg | ctg | gtg | gca | ggg | atc | tat | cta | atg | tgg | agg | cac | gaa | 869 |
| Ala | Thr | Trp | Val | Leu | Val | Ala | Gly | Ile | Tyr | Leu | Met | Trp | Arg | His | Glu |
|  | 185 |  |  |  | 190 |  |  |  | 195 |

| agg | atc | aag | aag | act | tcc | ttt | tct | acc | acc | aca | cta | ctg | ccc | ccc | att | 917 |
| Arg | Ile | Lys | Lys | Thr | Ser | Phe | Ser | Thr | Thr | Thr | Leu | Leu | Pro | Pro | Ile |
| 200 |  |  |  | 205 |  |  |  | 210 |  |  |  | 215 |

| aag | gtt | ctt | gtg | gtt | tac | cca | tct | gaa | ata | tgt | ttc | cat | cac | aca | att | 965 |
| Lys | Val | Leu | Val | Val | Tyr | Pro | Ser | Glu | Ile | Cys | Phe | His | His | Thr | Ile |
|  |  |  | 220 |  |  |  | 225 |  |  |  | 230 |

| tgt | tac | ttc | act | gaa | ttt | ctt | caa | aac | cat | tgc | aga | agt | gag | gtc | atc | 1013 |
| Cys | Tyr | Phe | Thr | Glu | Phe | Leu | Gln | Asn | His | Cys | Arg | Ser | Glu | Val | Ile |
|  |  | 235 |  |  |  | 240 |  |  |  | 245 |

| ctc | gaa | aag | tgg | cag | aaa | aag | aaa | ata | gca | gag | atg | ggt | cca | gtg | cag | 1061 |
| Leu | Glu | Lys | Trp | Gln | Lys | Lys | Lys | Ile | Ala | Glu | Met | Gly | Pro | Val | Gln |
|  | 250 |  |  |  | 255 |  |  |  | 260 |

| tgg | ctt | gcc | act | caa | aag | aag | gca | gca | gac | aaa | gtc | gtc | ttc | ctt | ctt | 1109 |
| Trp | Leu | Ala | Thr | Gln | Lys | Lys | Ala | Ala | Asp | Lys | Val | Val | Phe | Leu | Leu |
| 265 |  |  |  | 270 |  |  |  | 275 |

| tcc | aat | gac | gtc | aac | agt | gtg | tgc | gat | ggt | acc | tgt | ggc | aag | agc | gag | 1157 |
| Ser | Asn | Asp | Val | Asn | Ser | Val | Cys | Asp | Gly | Thr | Cys | Gly | Lys | Ser | Glu |
| 280 |  |  |  | 285 |  |  |  | 290 |  |  |  | 295 |

| ggc | agt | ccc | agt | gag | aac | tct | caa | gac | ctc | ttc | ccc | ctt | gcc | ttt | aac | 1205 |
| Gly | Ser | Pro | Ser | Glu | Asn | Ser | Gln | Asp | Leu | Phe | Pro | Leu | Ala | Phe | Asn |
|  |  |  | 300 |  |  |  | 305 |  |  |  | 310 |

| ctt | ttc | tgc | agt | gat | cta | aga | agc | cag | att | cat | ctg | cac | aaa | tac | gtg | 1253 |

```
Leu Phe Cys Ser Asp Leu Arg Ser Gln Ile His Leu His Lys Tyr Val
            315                 320                 325 gtg gtc tac ttt aga gag att gat aca aaa gac gat tac aat gct ctc      1301
Val Val Tyr Phe Arg Glu Ile Asp Thr Lys Asp Asp Tyr Asn Ala Leu
            330                 335                 340 agt gtc tgc ccc aag tac cac ctc atg aag gat gcc act gct ttc tgt      1349
Ser Val Cys Pro Lys Tyr His Leu Met Lys Asp Ala Thr Ala Phe Cys
345                 350                 355 gca gaa ctt ctc cat gtc aag cag cag gtg tca gca gga aaa aga tca      1397
Ala Glu Leu Leu His Val Lys Gln Gln Val Ser Ala Gly Lys Arg Ser
360                 365                 370                 375 caa gcc tgc cac gat ggc tgc tgc tcc ttg tagcccaccc atgagaagca        1447
Gln Ala Cys His Asp Gly Cys Cys Ser Leu
            380                 385 agagacctta aaggcttcct atcccaccaa ttacagggaa aaacgtgtgt gatgatcctga    1507 agcttactat gcagcctaca acagcctta gtaattaaaa cattttatac caataaaatt     1567
ttcaaatatt gctaactaat gtagcattaa ctaacgattg gaaactacat ttacaacttc    1627
aaagctgttt tatacataga aatcaattac agctttaatt gaaaactgta accattttga    1687
taatgcaaca ataaagcatc ttcagc                                          1713

<210> SEQ ID NO 7
<211> LENGTH: 385
<212> TYPE: PRT
<213> ORGANISM: Homo sapiens

<400> SEQUENCE: 7

Met Trp Thr Phe Ser Tyr Ile Gly Phe Pro Val Glu Leu Asn Thr Val
1               5                   10                  15

Tyr Phe Ile Gly Ala His Asn Ile Pro Asn Ala Asn Met Asn Glu Asp
            20                  25                  30

Gly Pro Ser Met Ser Val Asn Phe Thr Ser Pro Gly Cys Leu Asp His
        35                  40                  45

Ile Met Lys Tyr Lys Lys Lys Cys Val Lys Ala Gly Ser Leu Trp Asp
    50                  55                  60

Pro Asn Ile Thr Ala Cys Lys Lys Asn Glu Glu Thr Val Glu Val Asn
65                  70                  75                  80

Phe Thr Thr Thr Pro Leu Gly Asn Arg Tyr Met Ala Leu Ile Gln His
                85                  90                  95

Ser Thr Ile Ile Gly Phe Ser Gln Val Phe Glu Pro His Gln Lys Lys
            100                 105                 110

Gln Thr Arg Ala Ser Val Val Ile Pro Val Thr Gly Asp Ser Glu Gly
        115                 120                 125

Ala Thr Val Gln Leu Thr Pro Tyr Phe Pro Thr Cys Gly Ser Asp Cys
    130                 135                 140

Ile Arg His Lys Gly Thr Val Leu Cys Pro Gln Thr Gly Val Pro
145                 150                 155                 160

Phe Pro Leu Asp Asn Asn Lys Ser Lys Pro Gly Gly Trp Leu Pro Leu
                165                 170                 175

Leu Leu Leu Ser Leu Leu Val Ala Thr Trp Val Leu Val Ala Gly Ile
            180                 185                 190

Tyr Leu Met Trp Arg His Glu Arg Ile Lys Lys Thr Ser Phe Ser Thr
        195                 200                 205

Thr Thr Leu Leu Pro Pro Ile Lys Val Leu Val Val Tyr Pro Ser Glu
    210                 215                 220
```

-continued

```
Ile Cys Phe His His Thr Ile Cys Tyr Phe Thr Glu Phe Leu Gln Asn
225                 230                 235                 240

His Cys Arg Ser Glu Val Ile Leu Glu Lys Trp Gln Lys Lys Lys Ile
            245                 250                 255

Ala Glu Met Gly Pro Val Gln Trp Leu Ala Thr Gln Lys Lys Ala Ala
        260                 265                 270

Asp Lys Val Val Phe Leu Leu Ser Asn Asp Val Asn Ser Val Cys Asp
    275                 280                 285

Gly Thr Cys Gly Lys Ser Glu Gly Ser Pro Ser Glu Asn Ser Gln Asp
290                 295                 300

Leu Phe Pro Leu Ala Phe Asn Leu Phe Cys Ser Asp Leu Arg Ser Gln
305                 310                 315                 320

Ile His Leu His Lys Tyr Val Val Tyr Phe Arg Glu Ile Asp Thr
                325                 330                 335

Lys Asp Asp Tyr Asn Ala Leu Ser Val Cys Pro Lys Tyr His Leu Met
            340                 345                 350

Lys Asp Ala Thr Ala Phe Cys Ala Glu Leu Leu His Val Lys Gln Gln
        355                 360                 365

Val Ser Ala Gly Lys Arg Ser Gln Ala Cys His Asp Gly Cys Cys Ser
    370                 375                 380

Leu
385

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: PCR Primer
      2429-59

<400> SEQUENCE: 8
gcagacactg agagcattgt aatcg                                              25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: PCR Primer
      1916-83

<400> SEQUENCE: 9
ggctcgtatg ttgtgtggaa ttgtgag                                            27

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR Primer
      2429-56

<400> SEQUENCE: 10
atcaagaaga cttccttttc tac                                                23

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer
```

-continued 1916-80

<400> SEQUENCE: 11
tgcaaggcga ttaagttggg taacgccag                                29

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Nested PCR
      Primer

<400> SEQUENCE: 12
gccgacgggg acgtggatga ac                                       22

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Nested PCR
      Primer

<400> SEQUENCE: 13
catgattacg ccaagctcta atacgactc                                29

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Nested PCR
      Primer

<400> SEQUENCE: 14
cttcgccgag tgcctgtgca g                                        21

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Nest PCR
      Primer

<400> SEQUENCE: 15
tcacgacgtt gtaaaacgac ggccagtg                                 28

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: PCR PRimer
      2469-50

<400> SEQUENCE: 16
gcgatgtcgc tcgtgctgct aag                                      23

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: PCR Primer
      2469-54

<400> SEQUENCE: 17
gcagcctggt gaggtgaaat tcac                                              24

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Peptide

<400> SEQUENCE: 18

Tyr Gly Arg Lys Lys Arg Arg Gln Arg Arg Arg
 1               5                  10

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Peptide

<400> SEQUENCE: 19

Phe Ile Thr Cys Gly Gly Gly Tyr Gly Arg Lys Lys Arg Arg Gln Arg
 1               5                  10                  15

Arg Arg

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Epogen
      signal peptide

<400> SEQUENCE: 20

Met Gly Val His Glu Cys Pro Ala Trp Leu Trp Leu Leu Leu Ser Leu
 1               5                  10                  15

Leu Ser Leu Pro Leu Gly Leu Pro Val Leu Gly
                20                  25

<210> SEQ ID NO 21
<211> LENGTH: 233
<212> TYPE: PRT
<213> ORGANISM: Artificial Sequence
<220> FEATURE:
<223> OTHER INFORMATION: Description of Artificial Sequence: peptide of
      Fc fragment

<400> SEQUENCE: 21

Glu Pro Lys Ser Ala Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 22
<211> LENGTH: 644
<212> TYPE: DNA
<213> ORGANISM: Homo sapiens
<220> FEATURE:
<221> NAME/KEY: CDS
<222> LOCATION: (159)..(641)

<400> SEQUENCE: 22

```
ctcaagtcac tccctaaaaa gacagtggaa ataaatttga ataaacaaaa caggcttgct      60
gaaaataaaa tcaggactcc taacctgctc cagtcagcct gcttccacga ggcctgtcag     120
tcagtgcccc acttgtgact gagtgtgcag tgcccagc atg tac cag gtg gtt gca    176
                                          Met Tyr Gln Val Val Ala
                                            1               5 ttc ttg gca atg gtc atg gga acc cac acc tac agc cac tgg ccc agc      224
Phe Leu Ala Met Val Met Gly Thr His Thr Tyr Ser His Trp Pro Ser
             10                  15                  20 tgc tgc ccc agc aaa ggg cag gac acc tct gag gag ctg ctg agg tgg      272
Cys Cys Pro Ser Lys Gly Gln Asp Thr Ser Glu Glu Leu Leu Arg Trp
         25                  30                  35 agc act gtg cct gtg cct ccc cta gag cct gct agg ccc aac cgc cac      320
Ser Thr Val Pro Val Pro Pro Leu Glu Pro Ala Arg Pro Asn Arg His
     40                  45                  50 cca gag tcc tgt agg gcc agt gaa gat gga ccc ctc aac agc agg gcc      368
Pro Glu Ser Cys Arg Ala Ser Glu Asp Gly Pro Leu Asn Ser Arg Ala
 55                  60                  65                  70 atc tcc ccc tgg aga tat gag ttg gac aga gac ttg aac cgg ctc ccc      416
Ile Ser Pro Trp Arg Tyr Glu Leu Asp Arg Asp Leu Asn Arg Leu Pro
                 75                  80                  85 cag gac ctg tac cac gcc cgt tgc ctg tgc ccg cac tgc gtc agc cta      464
Gln Asp Leu Tyr His Ala Arg Cys Leu Cys Pro His Cys Val Ser Leu
             90                  95                 100 cag aca ggc tcc cac atg gac ccc cgg ggc aac tcg gag ctg ctc tac      512
Gln Thr Gly Ser His Met Asp Pro Arg Gly Asn Ser Glu Leu Leu Tyr
        105                 110                 115 cac aac cag act gtc ttc tac cgg cgg cca tgc cat ggc gag aag ggc      560
His Asn Gln Thr Val Phe Tyr Arg Arg Pro Cys His Gly Glu Lys Gly
    120                 125                 130 acc cac aag ggc tac tgc ctg gag cgc agg ctg tac cgt gtt tcc tta      608
```

```
Thr His Lys Gly Tyr Cys Leu Glu Arg Arg Leu Tyr Arg Val Ser Leu
135                 140                 145                 150 gct tgt gtg tgt gtg cgg ccc cgt gtg atg ggc tag                           644
Ala Cys Val Cys Val Arg Pro Arg Val Met Gly
                    155                 160
```

<210> SEQ ID NO 23
<211> LENGTH: 161
<212> TYPE: PRT
<213> ORGANISM: Homo sapiens

<400> SEQUENCE: 23

```
Met Tyr Gln Val Val Ala Phe Leu Ala Met Val Gly Thr His Thr
 1               5                  10                  15

Tyr Ser His Trp Pro Ser Cys Cys Pro Ser Lys Gly Gln Asp Thr Ser
                 20                  25                  30

Glu Glu Leu Leu Arg Trp Ser Thr Val Pro Val Pro Pro Leu Glu Pro
             35                  40                  45

Ala Arg Pro Asn Arg His Pro Glu Ser Cys Arg Ala Ser Glu Asp Gly
         50                  55                  60

Pro Leu Asn Ser Arg Ala Ile Ser Pro Trp Arg Tyr Glu Leu Asp Arg
 65                  70                  75                  80

Asp Leu Asn Arg Leu Pro Gln Asp Leu Tyr His Ala Arg Cys Leu Cys
                 85                  90                  95

Pro His Cys Val Ser Leu Gln Thr Gly Ser His Met Asp Pro Arg Gly
             100                 105                 110

Asn Ser Glu Leu Leu Tyr His Asn Gln Thr Val Phe Tyr Arg Arg Pro
         115                 120                 125

Cys His Gly Glu Lys Gly Thr His Lys Gly Tyr Cys Leu Glu Arg Arg
     130                 135                 140

Leu Tyr Arg Val Ser Leu Ala Cys Val Cys Val Arg Pro Arg Val Met
145                 150                 155                 160

Gly
```

<210> SEQ ID NO 24
<211> LENGTH: 521
<212> TYPE: PRT
<213> ORGANISM: Homo sapiens

<400> SEQUENCE: 24

```
Met Ser Leu Val Leu Leu Ser Leu Ala Ala Leu Cys Arg Ser Ala Val
 1               5                  10                  15

Pro Arg Glu Pro Thr Val Gln Cys Gly Ser Glu Thr Gly Pro Ser Pro
                 20                  25                  30

Glu Trp Met Leu Gln His Asp Leu Ile Pro Gly Asp Leu Arg Asp Leu
             35                  40                  45

Arg Val Glu Pro Val Thr Thr Ser Val Ala Thr Gly Asp Tyr Ser Ile
         50                  55                  60

Leu Met Asn Val Ser Trp Val Leu Arg Ala Asp Ala Ser Ile Arg Leu
 65                  70                  75                  80

Leu Lys Ala Thr Lys Ile Cys Val Thr Gly Lys Ser Asn Phe Gln Ser
                 85                  90                  95

Tyr Ser Cys Val Arg Cys Asn Tyr Thr Glu Ala Phe Gln Thr Gln Ser
             100                 105                 110

Gly Gly Lys Trp Thr Phe Ser Tyr Ile Gly Phe Pro Val Glu Leu Asn
         115                 120                 125
```

```
Thr Val Tyr Phe Ile Gly Ala His Asn Ile Pro Asn Ala Asn Met Asn
130                 135                 140

Glu Asp Gly Pro Ser Met Ser Val Asn Phe Thr Ser Pro Gly Cys Leu
145                 150                 155                 160

Asp His Ile Met Lys Tyr Lys Lys Cys Val Lys Ala Gly Ser Leu
            165                 170                 175

Trp Asp Pro Asn Ile Thr Ala Cys Lys Lys Asn Glu Glu Thr Val Glu
            180                 185                 190

Val Asn Phe Thr Thr Thr Pro Leu Gly Asn Arg Tyr Met Ala Leu Ile
            195                 200                 205

Gln His Ser Thr Ile Ile Gly Phe Ser Gln Val Phe Glu Pro His Gln
210                 215                 220

Lys Lys Gln Thr Arg Ala Ser Val Val Ile Pro Val Thr Gly Asp Ser
225                 230                 235                 240

Glu Gly Ala Thr Val Gln Leu Thr Pro Tyr Phe Pro Thr Cys Gly Ser
            245                 250                 255

Asp Cys Ile Arg His Lys Gly Thr Val Val Leu Cys Pro Gln Thr Gly
            260                 265                 270

Val Pro Phe Pro Leu Asp Asn Asn Lys Ser Lys Pro Gly Gly Trp Leu
            275                 280                 285

Pro Ala Ala Glu Pro Lys Ser Cys Asp Lys Thr His Thr Cys Pro
290                 295                 300

Pro Cys Pro Ala Pro Glu Leu Leu Gly Gly Pro Ser Val Phe Leu Phe
305                 310                 315                 320

Pro Pro Lys Pro Lys Asp Thr Leu Met Ile Ser Arg Thr Pro Glu Val
            325                 330                 335

Thr Cys Val Val Val Asp Val Ser His Glu Asp Pro Glu Val Lys Phe
            340                 345                 350

Asn Trp Tyr Val Asp Gly Val Glu Val His Asn Ala Lys Thr Lys Pro
            355                 360                 365

Arg Glu Glu Gln Tyr Asn Ser Thr Tyr Arg Val Val Ser Val Leu Thr
370                 375                 380

Val Leu His Gln Asp Trp Leu Asn Gly Lys Glu Tyr Lys Cys Lys Val
385                 390                 395                 400

Ser Asn Lys Ala Leu Pro Ala Pro Ile Glu Lys Thr Ile Ser Lys Ala
            405                 410                 415

Lys Gly Gln Pro Arg Glu Pro Gln Val Tyr Thr Leu Pro Pro Ser Arg
            420                 425                 430

Asp Glu Leu Thr Lys Asn Gln Val Ser Leu Thr Cys Leu Val Lys Gly
            435                 440                 445

Phe Tyr Pro Ser Asp Ile Ala Val Glu Trp Glu Ser Asn Gly Gln Pro
            450                 455                 460

Glu Asn Asn Tyr Lys Thr Thr Pro Pro Val Leu Asp Ser Asp Gly Ser
465                 470                 475                 480

Phe Phe Lys Leu Thr Val Asp Lys Ser Arg Trp Gln Gln Gly Asn Val
            485                 490                 495

Phe Ser Cys Ser Val Met His Glu Ala Leu His Asn His Tyr Thr Gln
            500                 505                 510

Lys Ser Leu Ser Leu Ser Pro Gly Lys
            515                 520

<210> SEQ ID NO 25
<211> LENGTH: 585
<212> TYPE: PRT
```

<213> ORGANISM: Homo sapiens

<400> SEQUENCE: 25

```
Met Ser Leu Val Leu Leu Ser Leu Ala Ala Leu Cys Arg Ser Ala Val
  1               5                  10                  15
Pro Arg Glu Pro Thr Val Gln Cys Gly Ser Glu Thr Gly Pro Ser Pro
                 20                  25                  30
Glu Trp Met Leu Gln His Asp Leu Ile Pro Gly Asp Leu Arg Asp Leu
             35                  40                  45
Arg Val Glu Pro Val Thr Thr Ser Val Ala Thr Gly Asp Tyr Ser Ile
         50                  55                  60
Leu Met Asn Val Ser Trp Val Leu Arg Ala Asp Ala Ser Ile Arg Leu
 65                  70                  75                  80
Leu Lys Ala Thr Lys Ile Cys Val Thr Gly Lys Ser Asn Phe Gln Ser
                 85                  90                  95
Tyr Ser Cys Val Arg Leu Glu Cys Ser Gly Ala Ile Met Ala Arg Cys
            100                 105                 110
Asp Leu Asn Leu Leu Gly Ser Ser Asp Arg Ser Ala Ser Ala Ser Arg
        115                 120                 125
Ala Ala Gly Thr Ala Gly Val Gly His Gln Thr Trp Leu Ile Phe Val
    130                 135                 140
Val Phe Val Glu Gly Gly Phe Thr Val Leu Leu Val Leu Asn Ser Ser
145                 150                 155                 160
Ala Gln Ala Ile Cys Leu Pro Arg Leu Pro Lys Val Leu Gly Leu Gln
                165                 170                 175
Trp Thr Phe Ser Tyr Ile Gly Phe Pro Val Glu Leu Asn Thr Val Tyr
            180                 185                 190
Phe Ile Gly Ala His Asn Ile Pro Asn Ala Asn Met Asn Glu Asp Gly
        195                 200                 205
Pro Ser Met Ser Val Asn Phe Thr Ser Pro Gly Cys Leu Asp His Ile
    210                 215                 220
Met Lys Tyr Lys Lys Cys Val Lys Ala Gly Ser Leu Trp Asp Pro
225                 230                 235                 240
Asn Ile Thr Ala Cys Lys Lys Asn Glu Glu Thr Val Glu Val Asn Phe
                245                 250                 255
Thr Thr Thr Pro Leu Gly Asn Arg Tyr Met Ala Leu Ile Gln His Ser
            260                 265                 270
Thr Ile Ile Gly Phe Ser Gln Val Phe Glu Pro His Gln Lys Lys Gln
        275                 280                 285
Thr Arg Ala Ser Val Val Ile Pro Val Thr Gly Asp Ser Glu Gly Ala
    290                 295                 300
Thr Val Gln Leu Thr Pro Tyr Phe Pro Thr Cys Gly Ser Asp Cys Ile
305                 310                 315                 320
Arg His Lys Gly Thr Val Val Leu Cys Pro Gln Thr Gly Val Pro Phe
                325                 330                 335
Pro Leu Asp Asn Asn Lys Ser Lys Pro Gly Gly Trp Leu Pro Ala Ala
            340                 345                 350
Ala Glu Pro Lys Ser Cys Asp Lys Thr His Thr Cys Pro Pro Cys Pro
        355                 360                 365
Ala Pro Glu Leu Leu Gly Gly Pro Ser Val Phe Leu Phe Pro Pro Lys
    370                 375                 380
Pro Lys Asp Thr Leu Met Ile Ser Arg Thr Pro Glu Val Thr Cys Val
385                 390                 395                 400
```

```
-continued

Val Val Asp Val Ser His Glu Asp Pro Glu Val Lys Phe Asn Trp Tyr
            405                 410                 415

Val Asp Gly Val Glu Val His Asn Ala Lys Thr Lys Pro Arg Glu Glu
            420                 425                 430

Gln Tyr Asn Ser Thr Tyr Arg Val Val Ser Val Leu Thr Val Leu His
            435                 440                 445

Gln Asp Trp Leu Asn Gly Lys Glu Tyr Lys Cys Lys Val Ser Asn Lys
        450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
            485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
            530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
            565                 570                 575

Lys Ser Leu Ser Leu Ser Pro Gly Lys
            580                 585

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 26
cattttccta catcggcttc cctg                                      24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 27
tgaatctggc ttctttcact gc                                        22
```